US010736692B2

(12) United States Patent
Pilcher et al.

(10) Patent No.: US 10,736,692 B2
(45) Date of Patent: Aug. 11, 2020

(54) NEUROMODULATION AND ASSOCIATED SYSTEMS AND METHODS FOR THE TREATMENT OF CANCER

(71) Applicant: Medtronic Ardian Luxembourg S.a.r.l., Luxembourg (LU)

(72) Inventors: Garrett Pilcher, Windsor, CA (US); Robert Melder, Santa Rosa, CA (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 714 days.

(21) Appl. No.: 15/194,303

(22) Filed: Jun. 27, 2016

(65) Prior Publication Data

US 2017/0312021 A1 Nov. 2, 2017

Related U.S. Application Data

(60) Provisional application No. 62/329,017, filed on Apr. 28, 2016.

(51) Int. Cl.
*A61B 18/14* (2006.01)
*A61N 7/02* (2006.01)
(Continued)

(52) U.S. Cl.
CPC .......... *A61B 18/1492* (2013.01); *A61B 5/40* (2013.01); *A61N 1/00* (2013.01); *A61N 1/0551* (2013.01);
(Continued)

(58) Field of Classification Search
CPC . A61B 18/02; A61B 18/1492; A61B 18/1815; A61B 18/24; A61B 2018/00434;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

EP 3054881 8/2016
EP 3226759 10/2017
(Continued)

OTHER PUBLICATIONS

Palm, Daniel, et al. "The Norepinephrine-Driven Metastasis Development of PC-3 Human Prostate Cancer Cells in BALB/c Nude Mice is Inhibited by β-Blockers." The Canadian Journal of Chemical Engineering, Wiley-Blackwell, Dec. 27, 2005, onlinelibrary. wiley.com/doi/full/10.1002/ijc.21723. (Year: 2005).*
(Continued)

*Primary Examiner* — Thomas A Giuliani
*Assistant Examiner* — Christine A Dedoulis

(57) ABSTRACT

Methods for treating a human patient diagnosed with cancer with therapeutic neuromodulation and associated systems are disclosed herein. Sympathetic nerve activity can contribute to several cellular and physiological processes associated with the progression of cancer. One aspect of the present technology is directed to methods that attenuate neural traffic along target sympathetic nerves innervating tissue proximate a primary malignant tumor. Other aspects are directed to methods that at least partially inhibit sympathetic neural activity in a renal nerve of a patient diagnosed with cancer or who has a high risk of developing cancer. Targeted sympathetic nerve activity can be attenuated to improve a measurable physiological parameter corresponding to the progression of cancer in the patient. The attenuation can be achieved, for example, using an intravascularly positioned catheter carrying a therapeutic assembly, e.g., a therapeutic assembly configured to use electri-
(Continued)

cally-induced, thermally-induced, and/or chemically-induced approaches to modulate the target sympathetic nerve.

27 Claims, 21 Drawing Sheets

(51) Int. Cl.
| | |
|---|---|
| A61N 1/00 | (2006.01) |
| A61N 1/36 | (2006.01) |
| A61B 5/00 | (2006.01) |
| A61N 1/05 | (2006.01) |
| A61N 7/00 | (2006.01) |
| A61B 18/00 | (2006.01) |
| A61B 90/00 | (2016.01) |
| A61B 18/02 | (2006.01) |
| A61B 18/18 | (2006.01) |
| A61B 18/24 | (2006.01) |

(52) U.S. Cl.
CPC ............ *A61N 1/36002* (2017.08); *A61N 7/00* (2013.01); *A61N 7/02* (2013.01); *A61N 7/022* (2013.01); *A61B 5/4035* (2013.01); *A61B 18/02* (2013.01); *A61B 18/1815* (2013.01); *A61B 18/24* (2013.01); *A61B 2018/00434* (2013.01); *A61B 2018/00511* (2013.01); *A61B 2018/00547* (2013.01); *A61B 2018/00559* (2013.01); *A61B 2018/00577* (2013.01); *A61B 2018/00642* (2013.01); *A61B 2018/0212* (2013.01); *A61B 2018/1861* (2013.01); *A61B 2090/374* (2016.02); *A61B 2090/376* (2016.02); *A61B 2090/378* (2016.02); *A61N 2007/0043* (2013.01)

(58) Field of Classification Search
CPC ........... A61B 2018/00511; A61B 2018/00547; A61B 2018/00559; A61B 2018/00577; A61B 2018/00642; A61B 2018/0212; A61B 2018/1861; A61B 2090/374; A61B 2090/376; A61B 2090/378; A61B 5/40; A61B 5/4035; A61B 18/04; A61N 1/00; A61N 1/0551; A61N 1/36002; A61N 2007/0043; A61N 2007/00; A61N 7/02; A61N 7/022
USPC ......................................................... 606/41
See application file for complete search history.

(56) References Cited

U.S. PATENT DOCUMENTS

| | | | |
|---|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster, Jr. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0181897 A1 | 9/2003 | Thomas et al. |
| 2003/0195507 A1 | 10/2003 | Stewart et al. |
| 2003/0199863 A1 | 10/2003 | Swanson et al. |

(56) References Cited

U.S. PATENT DOCUMENTS

| | | |
|---|---|---|
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2004/0249416 A1 | 12/2004 | Yun et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085046 A1 | 4/2006 | Rezai et al. |
| 2006/0085054 A1 | 4/2006 | Zikorus et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0207758 A1* | 8/2011 | Sobotka ............. A61B 18/1492 514/272 |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2013/0204068 A1* | 8/2013 | Gnanashanmugam ...................... A61N 5/1002 600/1 |
| 2015/0088111 A1* | 3/2015 | Brennan ............ A61N 1/36057 606/21 |
| 2016/0029960 A1* | 2/2016 | Toth ................... A61B 18/1492 600/301 |
| 2016/0082179 A1 | 3/2016 | Toth et al. |
| 2016/0213313 A1* | 7/2016 | Toth ................... A61B 18/1492 |

FOREIGN PATENT DOCUMENTS

| | | |
|---|---|---|
| EP | 3226792 | 10/2017 |
| WO | WO-199407446 A1 | 4/1994 |
| WO | WO-1995025472 A1 | 9/1995 |
| WO | WO-9531142 A1 | 11/1995 |
| WO | WO-1997036548 A1 | 10/1997 |
| WO | WO-1998042403 | 10/1998 |
| WO | WO-9900060 A1 | 1/1999 |
| WO | WO-2001022897 A1 | 4/2001 |
| WO | WO-2001070114 A1 | 9/2001 |
| WO | WO-2003022167 | 3/2003 |
| WO | WO-2003/082080 | 10/2003 |
| WO | WO-2005030072 A1 | 4/2005 |
| WO | WO--2005041748 A2 | 5/2005 |
| WO | WO-2005/110528 A1 | 11/2005 |
| WO | WO-2006041881 A2 | 4/2006 |
| WO | WO-2006105121 A2 | 10/2006 |
| WO | WO-2007008954 A2 | 1/2007 |
| WO | WO-2007078997 A2 | 7/2007 |
| WO | WO-2008049084 A2 | 4/2008 |

OTHER PUBLICATIONS

Lang, Kerstin, et al. "Induction of a Metastatogenic Tumor Cell Type by Neurotransmitters and Its Pharmacological Inhibition by Established Drugs." The Canadian Journal of Chemical Engineering, Wiley-Blackwell, Jun. 10, 2004, onlinelibrary.wiley.com/doi/10.1002/ijc.20410. (Year: 2004).*

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter," Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

Oz, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Pieper et al., "Design and Implementation of a New Computerized System for Intraoperative Cardiac Mapping." Journal of Applied Physiology, 1991, vol. 71, No. 4, pp. 1529-1539.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

U.S. Appl. No. 60/852,787, filed Oct. 18, 2006, 112 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

"Combination of Drugs for Diabetes and Hypertension may Offer an Effective New Way to Combat Cancer", 2017, http://www.newsgram.com/combination-of-drugs-for-diabetes-and-hypertension-may-offer-an-effective-new-way-to-combat-cancer/.

(56) References Cited

OTHER PUBLICATIONS

Schlaich, et al. "Effects of Renal Denervation on Sympathetic Activation, Blood Pressure, and Glucose Metabolism in Patients with Resistant Hypertension", Font. Physiol., 2012 vol. 3 (10), pp. 1-7.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pages.
U.S. Appl. No. 11/363,867, filed Feb. 27, 2006, 70 pages.
U.S. Appl. No. 60/813,589, filed Dec. 29, 2005, 62 pgs.
Ureter, https://en.wikipedia.org/wiki/Ureter, Jun. 2016, 6 pgs.
Cole, Steven W. et al., Molecular "Pathways:Beta-adrenergic signaling in cancer", Clin. Cancer Res., Mar. 1, 2012; 18(5):1201-1206, 10 pages.
Gao, Dingcheng et al., "Endothelial Progenitor Cells Control the Angiogenic Switch in Mouse Lung Metastasis", Science, vol. 319, Issue 5860, Jan. 11, 2008, Abstract, 16 pages.
Guo, Kun et al., "Interaction of the Sympatic Nerce with Pancreatic Cancer Cells Promotes Perineural Invasion through the Activation of STAT3 Signaling." Molecular Cancer Therapeutics, vol. 12, Mar. 2013, 1 page.
Zhao, Chun-Mei et al., "Denervation supporesses gastric tumorigenesis." Science Translation Medicine, Aug. 20, 2014, vol. 6, Issue 250, 25 pages.
Spill, Fabian et al., "Impact of The Physical Microenvironment on Tumor Progression and Metastasis." Tissue, Cell & Pathway Engrineering, Aug. 2016, Abstract, 3 pages.
Al-Wadei, Hussein A.N. et al., "Social Stress Promotes and Aminobutyric Acid Inhibits Tumor Growth in Mouse Models of Non-Small Cell Lung Cancer." American Association for Cancer Research, Mar. 23, 2016, 9 pages.
Kirchmair, Rudolf et al., "The Neuropeptide Secretoneurin Acts as a Direct Angiogenic Cytokine In Vitro and In Vivo." Circulation, Feb. 17, 2004, 8 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Szpunar, MJ et al., "Sympathetic innervation, norepinephrine content, and norepinephrine turnover in orthotopic and spontaneous models of breast cancer." Brain Behav Immun, Dec. 21, 2015, Abstract, 1 page.
Brown, Edward, "Sympathetic Nervous System Activation, Angiogenesis and Tumor Growth" University of Rochester Medical Center, accessed Mar. 9, 2017, 2 pages, https://www.urmc.rochester.edu/labs/brown-lab/projects/.
Yokota, Jun et al., "Tumor Progression and Metastasis." Carcinogenesis, vol. 21, No. 3, 2000, 497-503.
Madden, Kelley S et al.., "Early Impact of Social Isolation and Breast Tumor Progression in Mice." Brain Behav Immun, Mar. 2013; 15 pages.
Magnon, Claire et al., "Autonomic Nerve Development Contributes to Prostate Cancer Progression." Science, vol. 341, Jul. 12, 2013, 11 pages.
Pimentel, Matthew A., "Sympathetic Nervous System Regulation of Metastasis." Madame Curie Bioscience Database—NCBI Bookshelf, 2013, 13 pages.
Pattabiraman, Diwakar R. et al., "Box 3: What Constitutes the Tumour Microenvironment?" Nature Reviews Drug Discovery, vol. 13, 2014, 3 pages.
Thaker, Premal H. et al., "Chronic Stress Promotes Tumor Growth and Angeiogenesis in a Mouse Model of Ovarian Carcinoma." Nature Medicine, vol. 12, E-Publication Jul. 2006, Abstract, 3 pages.
Campbell, J. et al., "Stimulation of Host Bone Marrow Stromal Cells by Sympathetic Nerves Promotes Breast Cancer Bone Metastasis in Mice." PloS Biology, Jul. 2012, vol. 10, Issue 7, 12 pages.

(56) References Cited

OTHER PUBLICATIONS

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison AwardsTM" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Curtis, J.J., et al., "Surgical therapy for persistent hypertension after renal transplantation." Transplantation, 1981, 31: 125-128.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dibona, G.F., et al. "Neural control of renal function." Physiol Rev, 77:75-197 (1997).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*, 174: 1592-1594 (2000).

Han, Y.-M, et al., "Renal artery embolization with diluted hot contrast medium: An experimental study." J Vasc Intery Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

(56) References Cited

OTHER PUBLICATIONS

Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:11-17-11-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter Ablation of Cardiac Autonomic Nerves for Prevention of Vagal Atrial Fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversable renal denervation on haemodynamic and excretory functions on the ipsilateral and contralateral kidney in the cat." Hypertension, 4: 181-188 (1986).

Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Levin et al. Reexamination Application 95/002,209 U.S. Pat. No. 8,150,518 filed Sep. 13, 2012.
Levin et al., Reexamination Application 95/002,233 U.S. Pat. No. 8,131,372 filed Sep. 13, 2012.
Levin et al., Reexamination Application 95/002,243 U.S. Pat. No. 7,162,303 filed Sep. 13, 2012.
Demarais et al., Reexamination Application 95/002,253 U.S. Pat. No. 8,131,371 filed Sep. 13, 2012.
Demarais et al., Reexamination Application 95/002,255 U.S. Pat. No. 7,617,005 filed Sep. 13, 2012.
Demarais et al., Reexamination Application 95/002,292 U.S. Pat. No. 8,175,711 filed Sep. 14, 2012.
Demarias et al., Reexamination Application 95/002,327 U.S. Pat. No. 8,145,317 filed Sep. 14, 2012.
Demarais et al., Reexamination Application 95/002,335 U.S. Pat. No. 8,150,520 filed Sep. 14, 2012.
Levin et al., Reexamination Application 95/002,336 U.S. Pat. No. 7,647,115 filed Sep. 14, 2012.
Demarais et al., Reexamination Application 95/002,356 U.S. Pat. No. 8,150,519 filed Sep. 14, 2012.

* cited by examiner

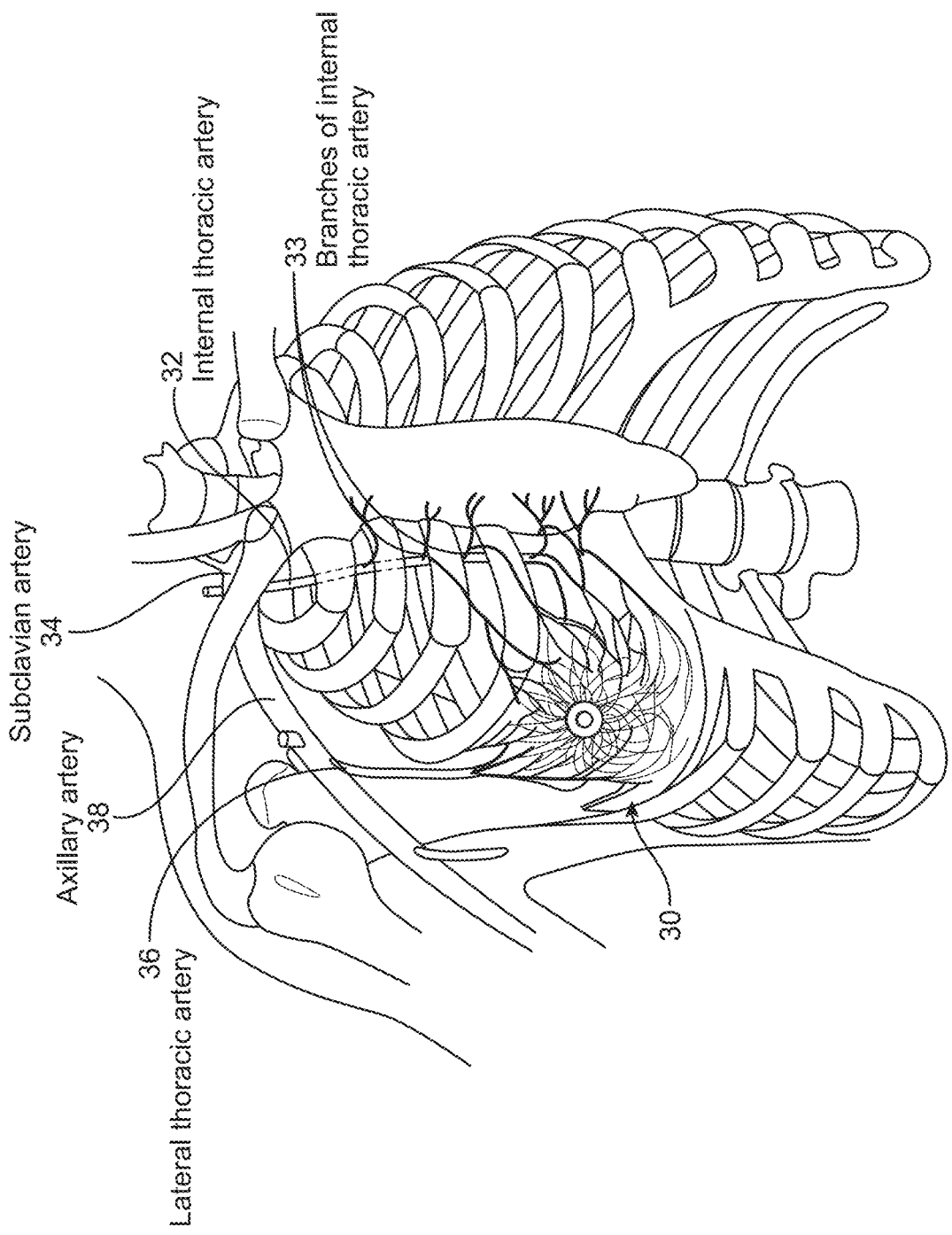

Renal Denervation Preclinical Efficacy:
Review of 66 Treated and 64 Naïve Swine

| Group N=Arteries or kidneys | % Non-functional Area | Cortical Axon Area per $mm^2$ | Mean NE (pg/mg) |
|---|---|---|---|
| Naïve 7 day N=64 | 14.6 ± 8.0 | 207.2 ± 134.6 | 264.8 ± 82.9 |
| Symplicity 7 day N=54 | 56.9 ± 28.3 | 66.8 ± 84.6 (68% Decrease) | 92.7 ± 92.7 (65% Decrease) |
| Spyral 7 Day N=12 | 47.3 ± 26.5 | 97.4 ± 73.1 (54% Decrease) | 88 ± 75 (68% Decrease) |

FIG. 16A

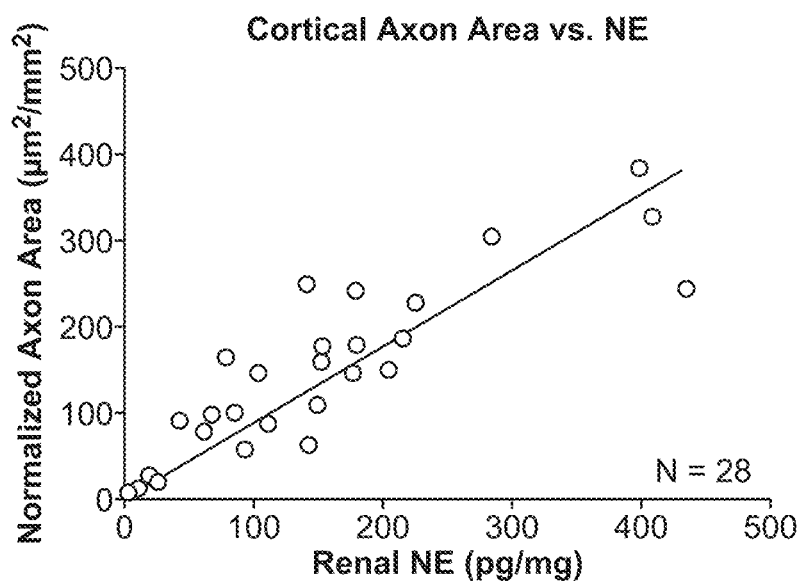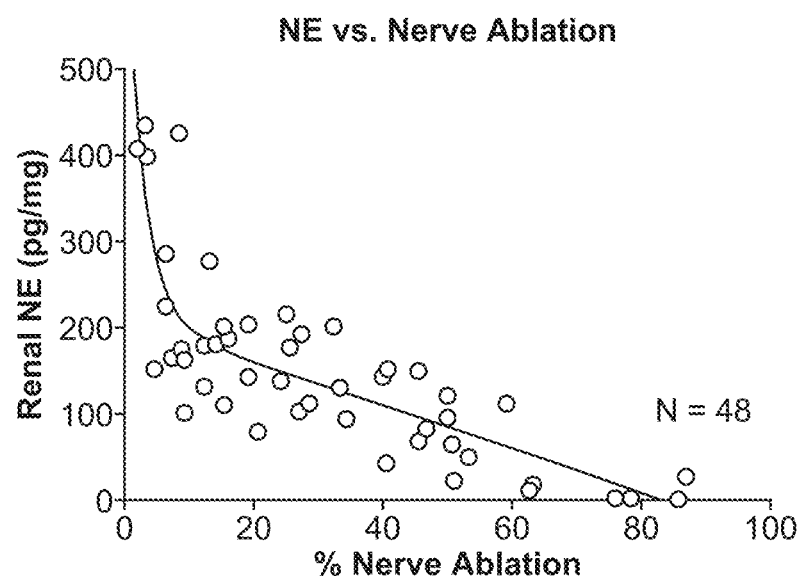
FIG. 16B

NEUROMODULATION AND ASSOCIATED SYSTEMS AND METHODS FOR THE TREATMENT OF CANCER

RELATED APPLICATIONS

This application claims the benefit of U.S. Provisional Patent Application No. 62/329,017, filed Apr. 28, 2016, the disclosure of which is herein incorporated by reference in its entirety.

TECHNICAL FIELD

The present technology relates generally to methods and systems for catheter-based neuromodulation. In particular, several embodiments are directed to treatment of cancer and/or improving one or more measurable physiological parameters corresponding to the progression of cancer using neuromodulation and associated systems and methods.

BACKGROUND

Globally, cancer and cancer-related complications affect millions of patients every year, making cancer one of the leading international health concerns. In fact, the World Health Organization reports that among economically-developed nations, cancer is ranked second behind cardiovascular disease as the leading cause of death. Cancer, which is the abnormal growth of cells in a patient's body, may have the potential to invade or spread to other parts of the body via local spread or through blood or lymphatic systems to secondary tissue sites. Such metastatic tumors or cancer that has spread from the primary malignancy site are often the cause of cancer-related death. Typically, patient prognosis depends on a variety of aspects, including the type of cancer and location of the primary malignancy, the stage of the cancer (e.g., size of primary malignant tumor, degree of spread from primary cancer origin, etc.) at the time of diagnosis, the grade of the cancer (e.g., the degree of cellular abnormality or other characteristics of the cancer cells, etc.), genetic traits/mutations and/or heterogeneity of the cancer, patient's age and/or health condition prior to diagnosis, and a patient's particular response to treatment. Additionally, it has been demonstrated that increased stress experienced by the patient, either following diagnosis or chronic stress experienced by the patient prior to diagnosis, has a negative impact on cancer progression and outcome.

Treatment following diagnosis is dependent on many of the above-described factors, but generally includes surgical removal of detected cancerous tissue, chemotherapy regimens and other anti-cancer agents, and/or radiation therapy of affected tissue. While these conventional treatments and therapies address removal and/or killing of cancerous cells and tissues, they can be ineffective at removing all cancerous cells from the body and in a manner that prevents metastasis and/or reoccurrence, especially in highly invasive cancers. Additionally, these primary treatments as well as long-term maintenance therapies (e.g., hormone therapy for breast cancer patients) can cause undesirable side effects and loss of quality of life. Accordingly, there is a need for alternative and/or adjunctive treatments that effectively reduce or inhibit the progression of cancer (e.g., inhibit metastasis, suspend or slow tumor growth, etc.) as well as provide better prognosis and outcomes for cancer patients with limited or no side effects.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 5 is a partially anatomical view illustrating the arterial supply to breast tissue.

FIG. 16A is a display table illustrating results from a study to determine the effects of renal denervation on cortical axon density and mean norepinephrine concentration in animal subjects.

FIG. 16B is a series of graphs illustrating the response correlation between normalized cortical axon area vs. norepinephrine concentration and norepinephrine concentration vs. extent of nerve ablation along the artery of the animal subjects of FIG. 16A.

DETAILED DESCRIPTION

The present technology is directed to apparatuses, systems, and methods for treating cancer and/or improving one or more measurable physiological parameters corresponding to the progression of cancer using neuromodulation. For example, some embodiments include performing therapeutically-effective renal neuromodulation on a patient diagnosed with cancer. In a particular embodiment, for example, the patient is diagnosed with a primary malignant tumor. Other embodiments include performing neuromodulation of a target sympathetic nerve innervating tissue proximate the primary malignant tumor in the patient and/or that control a function of an organ comprising the primary malignant tumor. Such organs can include the abdominal organs (e.g., pancreas, liver, kidney, stomach, gallbladder, colon, bladder, etc.) reproductive organs (e.g., testes, penis, prostate, uterus, ovaries, cervix, vulva, vagina, etc.) or other organs/location with incidences of cancer (e.g., lung, breast, etc.)

Still other embodiments include neuromodulating a target sympathetic nerve innervating a secondary tissue site in a manner that decreases a rate of colonization of circulating tumor cells at the secondary tissue site. Such secondary tissue sites may include, for example, the liver or lung. As discussed in greater detail below, neuromodulation can include rendering neural fibers inert, inactive, or otherwise completely or partially reduced in function. This result can be electrically-induced, thermally-induced, or induced by another mechanism during a neuromodulation procedure, e.g., a procedure including percutaneous transluminal intravascular access.

Specific details of several embodiments of the technology are described below with reference to FIGS. 1-16B. Although many of the embodiments are described herein with respect to electrically-induced, thermally-induced, and chemically-induced approaches, other treatment modalities in addition to those described herein are within the scope of the present technology. Additionally, several other embodiments of the technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-16B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Cancer

A. Initiation and Progression

Figure 1:
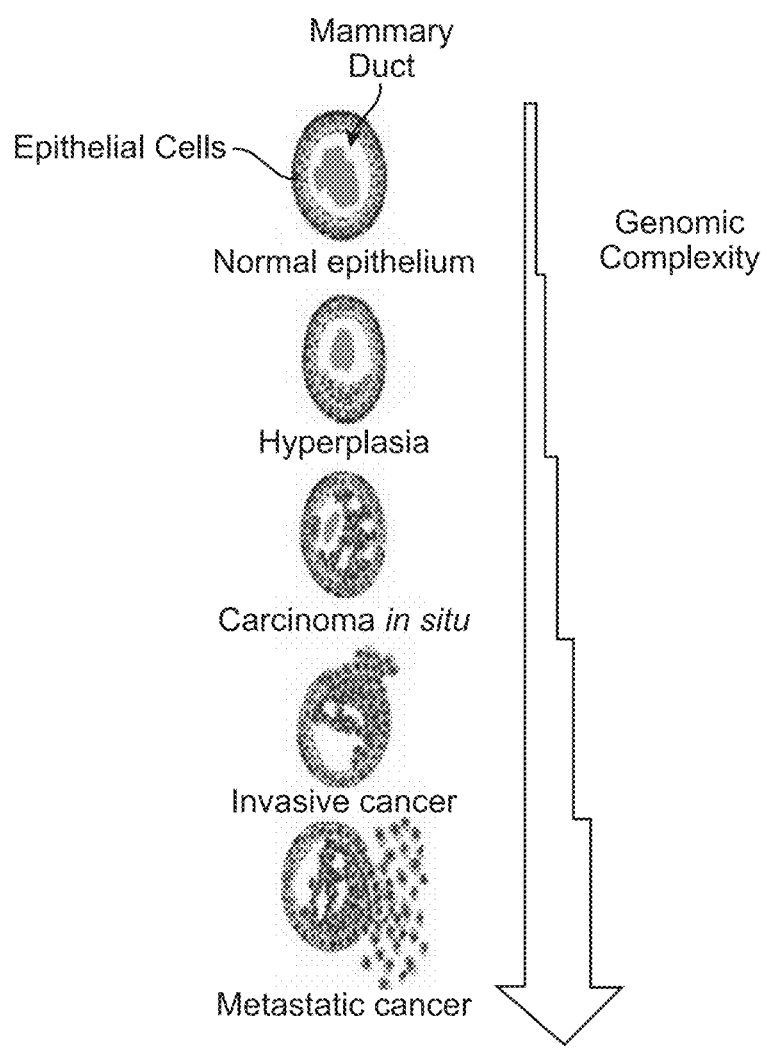
FIG. 1 schematically illustrates the increase in genomic complexity as normal epithelium of a mammary duct progresses through stages of ductal hyperplasia, ductal carcinoma in situ and ultimately to invasive/metastatic breast cancer.

Generally, abnormal tissue growth, known as neoplastic tissue growth, can be benign (i.e., non-cancerous) or malignant (i.e., cancerous) which designates that the neoplastic cells have the ability to invade neighboring tissue (e.g., locally invasive) or to metastasize to a secondary location in the body (e.g., via the lymphatic system or blood vasculature). The terms "cancer" or "cancerous" can refer to the physiological condition in which cells have lost their ability to divide in a controlled or regulated fashion. For example, cancer can include a population of rapidly dividing and growing cells that progressively accrues mutations in their genetic code that perturbs or evades the body's normal mechanisms of regulation or cell death and well as allows the cells to invade other tissues. FIG. 1 schematically illustrates the increase in genomic complexity as normal epithelium of a mammary duct progresses through stages of ductal hyperplasia, ductal carcinoma in situ and ultimately to invasive/metastatic breast cancer. As cancer is attributed to the accumulation of genetic alterations in the cells, the molecular mechanisms and characterizations of these alterations have been a source of persistent investigation. Without being bound by theory, studies strongly suggest that such genetic alterations accumulate in the cells in a stepwise manner during tumor progression (shown schematically in FIG. 1) and these transitions may, at least in part, rely on recruitment of other cells, components, and structures to the tumor microenvironment (Spill, F. et al., *Current Opinion in Biotechnology*, 2016; 40: 41-48).

Progression of human cancer from pre-malignant lesions, such as dysplasia and hyperplasia to primary malignant tumors and eventually to metastatic tumorigenesis has been clinically well recognized. The pre-malignant lesions are caused either by genetic alterations (e.g., initiated by mutagens) which induce monoclonal expansion of the cells, or by environmental factors, such as viral infection, which induce polyclonal expansion of the cells. This process in which normal cells are altered and/or become neoplastic is referred to as "tumor initiation". The term "tumor", as used herein, refers to any neoplastic cell growth or proliferation, whether malignant or benign, as well as to all pre-cancerous and cancerous cells and tissues. Several types of pre-malignant lesions can be detected in diverse organs prior to the appearance of fully malignant invasive tumors.

In the next phase of carcinogenesis, "tumor promotion" is assisted by further accumulation of genetic alterations occurring in one (or a few) of the pre-malignant cells, causing the cells to convert into a malignant genotype of clonal origin and to expand in number to produce a primary tumor or mass. Typically, at this early stage of primary tumor expansion, the cells are not invasive and metastatic; however further accumulation of genetic alterations in a fraction of cells (forming new clones within the tumor) provide such cells with invasiveness and metastatic potential. Accordingly, a primary malignant tumor is recognized to be biologically heterogeneous with some cells being invasive and malignant.

Figure 2:
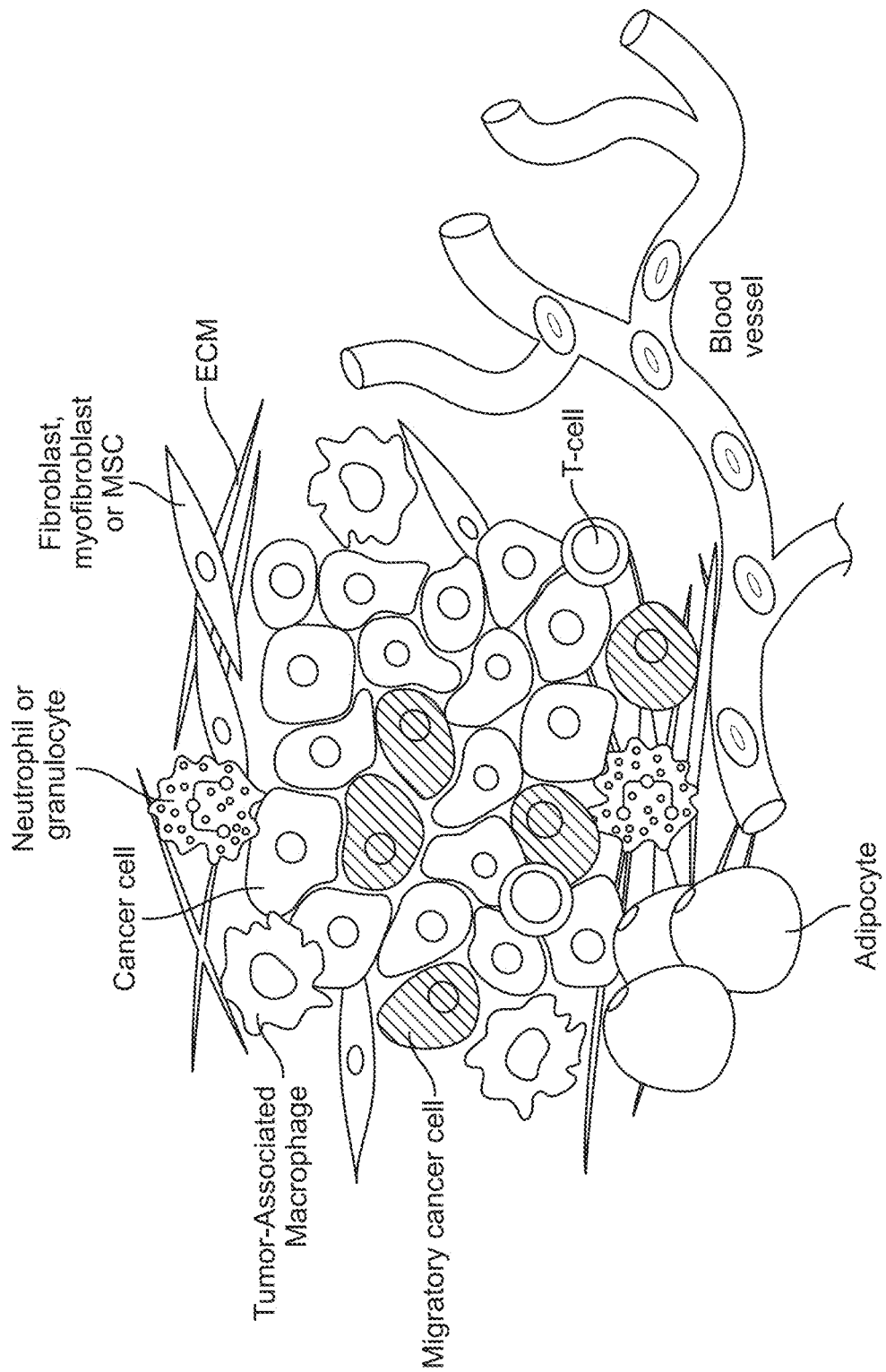
FIG. 2 is a schematic of a tumor microenvironment illustrating the complexity of the tumor stroma.

During tumor initiation and promotion, cancer cells create an environment for their proliferation by recruiting stromal cell components required for survival and growth, including fibroblasts, immune cells, pericytes, endothelial cells, nerve cells, blood vessels, and inflammatory cells (FIG. 2). "Tumor progression" then is characterized by increased growth speed and invasiveness of the tumor cells which is aided by these changes in the local tissue microenvironment. The tumor and the tumor microenvironment can become hypoxic, which can cause further genomic instability of cancer cells within. Partial relief from oxygen deprivation is provided by angiogenesis. For example, tumors as well as the tumor stroma induce angiogenesis or blood vessel growth by secreting various growth factors (e.g., vascular endothelial growth factor (VEGF), basic fibroblast growth factor (bFGF), secretoneurin, substance P, neuropeptide Y, etc.) to encourage capillary growth into the tumor for supplying oxygen and nutrients that allow for tumor expansion. Without being bound by theory, angiogenesis of the tumor tissue and surrounding microenvironment also aides in removal of tumor by-products and waste as well as providing hematogenous transport for metastatically competent cancer cells throughout the body.

FIG. 2 is a schematic of a tumor microenvironment illustrating the complexity of the tumor stroma. For example, the tumor microenvironment comprises a mixture of carcinoma cells (e.g., migratory and non-migratory), cells derived from hematopoietic stem cells (e.g., macrophages, T-cells, etc.), cells derived from mesenchymal cells (e.g., fibroblasts, myofibroblasts, mesenchymal stem cells (MSC), endothelial cells, adipocytes, etc.) and the non-cellular components of the extracellular matrix (ECM). Each of these components of the tumor microenvironment has a role in affecting tumor progression. For example, endothelial progenitor cells (EPCs), which are recruited from the bone marrow to the tumor stroma, are likely important in tumor progression and are proposed to be involved in angiogenesis (e.g., incorporated in the tumor vasculature) and in hematogenous spread of cancer cells (Gao, D., et al., Science, 2008; 319: 195-198; Nolan, D J., et al., Genes & Development, 2007; 21: 1546-1558). Secretion of VEGF recruits EPCs to the tumor microenvironment where they in turn recruit pericytes via secretion of platelet derived growth factor (PDGF). Together, they form new, but leaky (e.g., having enhanced permeability) blood vessels both in and around the growing tumor.

Referring back to FIG. 2, immune cells also populate the tumor microenvironment. In particular, the tumor cells recruit hematopoietic monocytes to the tumor stroma where they differentiate under the influence of the tumor microenvironment as tumor associated macrophages (TAMs). Once in the tumor microenvironment, these macrophages become tumor protective and facilitate metastasis. For example, TAMs secrete growth factors (e.g., epidermal growth factor (EGF), fibroblast growth factor (FGF)) as well as cytokines (e.g., IL-6, tumor necrosis factor (TNF)) that promote tumor growth. TAMs also promote the growth of new blood vessels via secretion of VEGF and PDGF into the tumor microenvironment. Additionally, TAMs secrete matrix metalloproteases that are known to degrade and compromise the ECM, thereby permitting further routes of tumor cell spread. Further, TAMs produce immunosuppressive molecules that thwart the adaptive immune system while further recruiting additional TAMs to the tumor microenvironment (Noy, R., and Pollard, J. W., Immunity, 2014; 41: 49-61).

Human tissues are primarily made up of epithelial cells tethered to each other (e.g., by immunoglobulins and cadherins) and to the ECM (e.g., by integrins), and mesenchymal cells, which are loosely associated, pro-migratory cells. Referring back to FIG. 1, normal epithelial cells adhere to one another to form cell layers, which act as barriers to protect our bodies and organs from the exterior environment, while the ECM (not shown) comprises a mixture of carbohydrate and protein molecules that provides both mechanical and biochemical support to the epithelial layers. In epithelial cancers (e.g., carcinomas), at least a subset of the malignant cancer cells can undergo an epithelial-to-mesenchymal transition (EMT), consisting of physical and genetic changes that alter the cell's attachment structures, polarity and migratory abilities. Such migratory abilities allow these cells to break down or break through the ECM, endothelial structures and/or invade nearby tissue structures. For example, once cancer cells acquire the necessary genetic alterations to become metastatic, many have the ability to penetrate the walls of lymphatic and/or blood vessels which allows them to circulate (i.e., circulating tumor cells) to other sites and tissues in the body. In these secondary locations, the circulating tumor cells are able to re-penetrate the walls of the lymphatic and/or blood vessels where they can revert to epithelial cells again through a mesenchymal-to-epithelial transition program and continue to multiply to form a secondary (e.g., metastatic) tumor.

B. Role of Sympathetic Nervous System

Correlative links between activation of physiological stress pathways and cancer progression and metastasis have been established. For example, chronic emotional stress, depression and/or lack of social support are all associated with poorer prognosis and mortality in cancer patients due to primary malignant tumor progression and metastasis to secondary tissue locations (Szpunar, M. J., et al., Cancer Prev. Res. 2013; 6:1262-1272). Chronic stress and/or social isolation can be as predictive of poorer disease outcome as other standard risk factors (e.g., smoking, blood pressure, and obesity) (Lutendorf, S. K., et al., Brain Behav Immun., 2011; 25: 250-255). In some studies, these biobehavioral factors are understood not to just have a role in disease progression, but also to have influence on cancer onset (Lutendorf, S. K., et al., Brain Behav Immun., 2009; 23: 176-183). The potential clinical links between stress and cancer progression have motivated investigations of the influence of the SNS on cancer biology.

Figure 3:
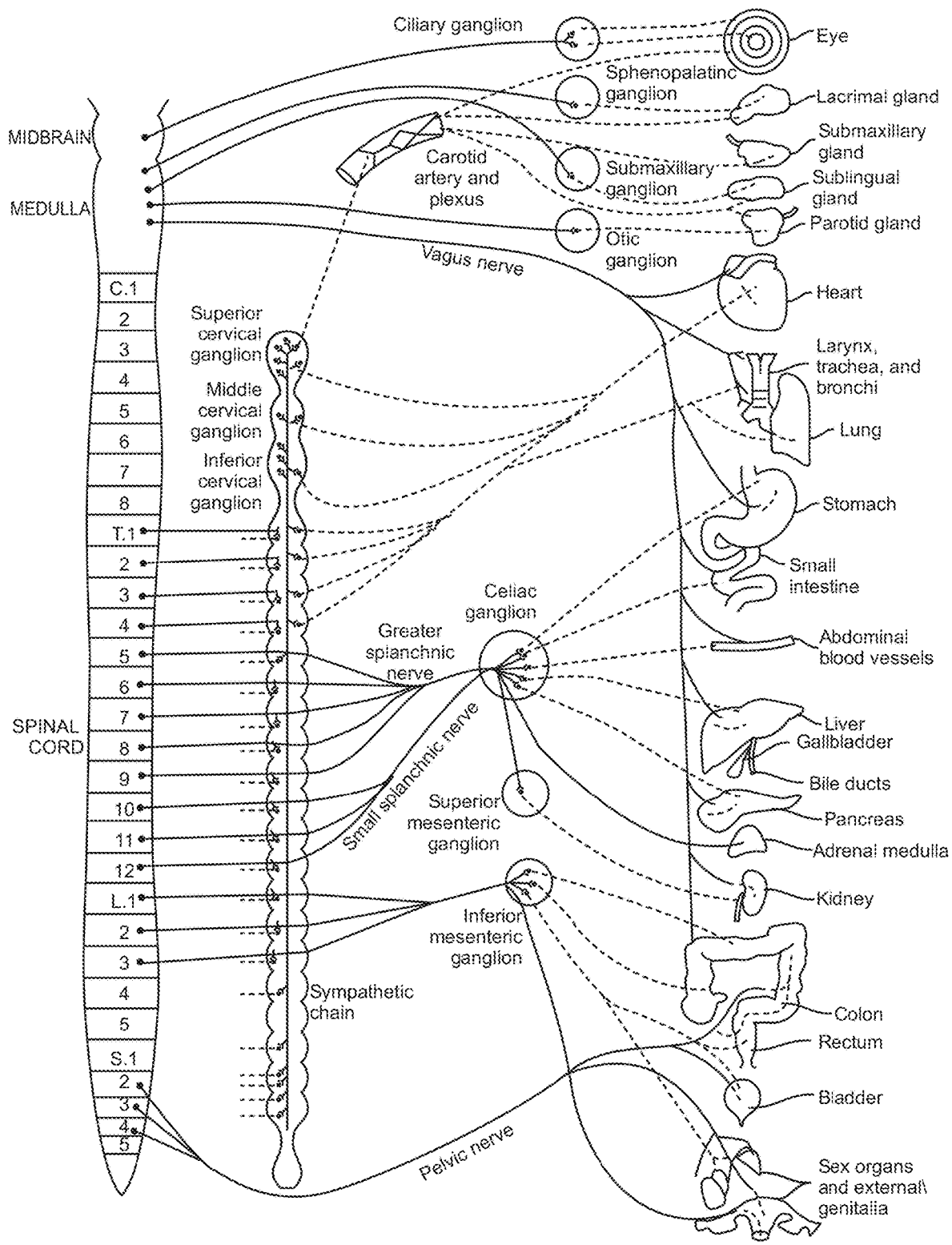
FIG. 3 is a conceptual illustration of the sympathetic nervous system (SNS) and how the brain communicates with the body via the SNS.

In response to chronic stress, cognitive and emotional information is processed by the central nervous system and transmitted via the peripheral nervous system to the rest of the body. The body's stress response involves activation of the SNS and concomitant production of signal mediators, such as the catecholamines norepinephrine and epinephrine, which arise both from post-ganglionic SNS terminal nerve fibers and the adrenal medulla (Cole, S. W., et al., Nature Reviews, 2015, 15: 563-572). As shown in FIG. 3, the SNS is a branch of the autonomic nervous system along with the enteric nervous system and parasympathetic nervous system. The SNS is a primarily involuntary bodily control system typically associated with stress responses. It is always active at a basal level (called sympathetic tone) and becomes more active during times of stress. The SNS regulates the function of virtually all human organ systems by localized release of catecholamines (e.g., norepinephrine) from sympathetic nerve terminals innervating these tissue and organ systems, spillover of norepinephrine from vascular neuro-muscular junctions (the primary source of norepinephrine in plasma), and by systemic circulation of catecholamines (e.g., epinephrine, norepinephrine) released from the adrenal gland in response to acute, transient stress or threats. Long-term variations in basal levels as well as spikes of circulating catecholamines from hyperactivity of the SNS responding to life circumstances can also exert more enduring regulatory effects on gene expression by altering constitutive gene expression profiles in a wide variety of tissues and organ systems.

SNS activation can release micro-molar concentrations of norepinephrine to specific and localized tissue locations when threats to homeostasis are detected (e.g., mobility of resources for microbial defense, wound healing, etc.), and spikes in systemic catecholamine levels due to the fight-or-flight response to acute stress can transiently enhance muscle strength, accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Individuals with chronic, low-level stress due to long-term exposure to adverse social circumstances (e.g., social isolation, poverty, demanding jobs, etc.) clinically present with greater levels of tissue and plasma norepinephrine levels than hormonal epinephrine levels (Cole, S. W., et al., *Nature Reviews*, 2015, 15: 563-572). Gene expression modifications and resultant physiological changes are mediated by activation of α-adrenergic and β-adrenergic receptors that are differentially expressed across various tissue types throughout the body. Activation of adrenergic receptors by norepinephrine, for example, initiate distinct molecular pathways and cellular changes in tissue genetic expression profiles that lend to the detection and abilities to deal with challenges and threats from their environments; however, these SNS-induced changes are also important in tumor progression and metastasis as shown in experiments linking β-adrenergic antagonists to reduced progression of primary tumors. For example, the distribution of catecholamines as well as changes in relative concentration levels paralleled alterations in activity in tumor tissue via β-adrenergically linked transcription control pathways mediating processes such as inflammation, metastatic capacity, and cell proliferation (Cole, S. W., et al., *Nature Reviews*, 2015, 15: 563-572; Lutgendorf, S. K., et al., *Brain Behav Immun.*, 2009, 23: 176-183).

Elevated catecholamine levels have been observed in both human cancer patients as well as animal models. Many of these studies demonstrate that low social support, chronic stress, and/or depression leads to β-adrenergic signaling and resultant activation of signaling transduction pathways that promote biological processes involved in cancer progression such as, for example, tumor cell proliferation, ECM alterations, angiogenesis, matrix metalloprotease activation, inflammatory responses and measurable increases in tumor cell invasion and metastasis (Sloan, E. K., et al., *Cancer Res*, 2010, 70: 7042-7052; Cole, S. W., et al., *Nature Reviews*, 2015, 15: 563-572). Experimental analysis in animal model systems and in human epidemiological studies have shown that behavioral stress can accelerate and/or enhance progression of breast cancer, prostate cancer, ovarian cancer, lung cancer, stomach cancer, colorectal cancer, neuroblastomas, malignant melanomas, pancreatic carcinoma and some hematopoietic cancers such as leukemia, among others (Cole, S. W., et al., *Nature Reviews*, 2015, 15: 563-572; Cole, S. W. and Sood, A. K., *Clin Cancer Res*, 2012, 18: 1201-1206; Sloan, E. K., et al., *Cancer Res*, 2010, 70: 7042-7052; Thaker, P. H., et al., Nature Medicine, 2006, 12: 939-944; Lutgendorf, S. K., et al., Brain Behav Immun., 2009, 23: 176-183; Lutgendorf, L. K., et al., Brain Behav Immun., 2011, 25:250-255; Lin, Q., et al., PLoS ONE 8:e61435; Al-Wadei, H. A. N., et al., Cancer Prev Res, 2012, 5: 189-196).

Without being bound by theory, chronic or repetitive low-grade SNS-activation increases norepinephrine levels within localized tissue areas as well as in systemic plasma levels and is believed to contribute to SNS-mediated regulation of cancer progression through many of the molecular and clinical changes described above. For example, the SNS may be involved in elements of tumor initiation, tumor growth, development of a pro-tumor microenvironment, and cancer cell metastasis.

Experimental challenges to tumorigenesis milestones have demonstrated the importance of β-adrenergic activation of signaling transduction pathways and, without being bound by theory, it is believed that many of the effects of chronic SNS activation on cancer progression involve β-adrenergic receptor activation on cancer cells as well as several other non-cancer cell types within the tumor microenvironment. In pre-cancerous or cancerous cells, experimental use of β-adrenergic antagonists have shown that catecholamine activation of β-adrenergic receptors activates known oncogenes as well as inhibits DNA repair and apoptosis in affected cells, thereby contributing to early steps in cancer cell formation such as chromosomal instability and chromosomal aberrations (Cole, S. W., et al., *Nature Reviews*, 2015, 15: 563-572). Other studies have demonstrated the role of β-adrenergic activation in promoting a localized inflammatory response via multiple routes. For example, β-adrenergic signal transduction results in transcriptional induction of pro-inflammatory cytokines (e.g., IL-6 and IL-8) in tumor cells as well as stimulation of tumor cells' chemotactic recruitment of macrophages to the tumor microenvironment. Further, norepinephrine activation of β-adrenergic receptors on precursor monocytes stimulates development of these immature cells in the bone marrow and spleen such that they can then be recruited into the tumor microenvironment, thereby significantly increasing the density of tumor-associated macrophages (TAMs) in the tumor stroma. As stated above, TAMs promote cancer through multiple pathways including increased angiogenesis, ECM remodeling, chemoattraction of pro-tumor immune cells, generating a pro-inflammatory environment and evasion of anti-tumor immune responses. Further involvement of the SNS in the body's immune response to tumor development is the β-adrenergic-mediated inhibition of T lymphocytes and natural killer cells as well as inhibition of the transcription of type I and type II interferons that all play roles in cell-mediated immune responses against cancers.

β-adrenergic signaling is also implicated in angiogenesis within the tumor and its associated microenvironment and may be, at least in part, dependent on macrophage recruitment to the tumor. In patients with ovarian cancer, poor social support has also been linked to higher levels of norepinephrine-induced, angiogenic cytokines including VEGF and IL-6, both in peripheral blood and in the tumor microenvironment (Lutgendorf, S. K., et al., *Cancer*, 2002, 95: 808-815; Thaker, P. H., et al., *Nature Medicine*, 2006, 12: 939-944). Studies using β-adrenergic antagonists demonstrated that β-adrenergic activation was required for stress-induced increases in blood vessel density in primary malignant mammary and ovarian tumors (Thaker, P. H., et al., *Nature Medicine*, 2006, 12: 939-944; Sloan, E. K., et al., *Cancer Res*, 2010, 70: 7042-7052).

In addition to release of norepinephrine at or near the tumor microenvironment, afferent (e.g., sensory) neurons may also play a role in inducing angiogenetic progression at the tumor site. For example, release of neuropeptides, such as secretoneurin, substance P and/or neuropeptide Y, by stimulated sensory nerves are commonly associated with increased inflammation and pain transmission to the CNS. These factors have additionally been demonstrated to have antigenic activity (Kirchmair, R., et al, *Circulation*, 2004, 109:777-783).

SNS influences on tumor progression also include induction of the EMT program in tumor cells that allow these cells to become invasive and metastatic (Cole, S. W., et al., *Nature Reviews*, 2015, 15: 563-572). Further influences of the SNS on cancer cell viability include β-adrenergic receptor mediated resistance of programmed cell death (e.g., via anoikis and/or apoptosis). In particular, SNS activation mediates inhibition of apoptotic responses to chemotherapy-mediated cell death, thereby attenuating the response of tumors to chemotherapy, while further employing β-adrenergic signaling pathways to upregulate expression of growth and survival factors (e.g., VEGF, IL-6, IL-8) (Wu, W., et al., et al., Biol. Pharm. Bull., 2001, 24: 772-776; Cole, S. W., et al., Nature Reviews, 2015, 15: 563-572).

Chronic stress may also increase SNS nerve density in and around a tumor and the surrounding microenvironment. For example, chronic stress has been shown to increase transcription levels of sympathetic neurotrophin nerve growth factor (NGF), which is required for the development and maintenance of SNS nerve fibers (Sloan, E. K., et al., J Neurosci., 2007, 27: 8857-8865). Experimental studies in animal models have shown that chronic social stress promotes growth and branching of SNS nerve fibers into peripheral, tumor and lymph node tissues (Id.). Additionally, SNS nerve innervation of particular tissues and organs may make those tissues more susceptible host environments for circulating tumor cells to form secondary metastatic tumors in chronically stressed individuals (Campbell, J. P., et al., PLoS Biology, 2012, 10 (e1001363): 1-11; Wu, W., et al., Biol. Pharm. Bull., 2001, 24: 772-776). For example, stress-induced SNS activation, and resultant catecholamine release to bone marrow stroma, has been shown to promote breast cancer cell colonization in bone marrow in animal models, and this effect was blocked in vivo with the β-blocker propranolol (Campbell, J. P., et al., PLoS Biology, 2012, 10 (e1001363): 1-11). In some instances, SNS activation may upregulate expression of trophic factors and chemokines (e.g., CXCL12) that attract tumor cells to activated neural fibers (Cole, S. W., et al., Nature Reviews, 2015, 15: 563-572).

Human epidemiological and in vivo animal model studies have suggested a potential therapeutic benefit to treating cancer patients with a β-adrenergic antagonist (i.e., β-blocker) to mitigate or assuage SNS effects on cancer progression. However, studies have shown inconsistent results depending on genetic profile of the tumor cells, location of the tumor, stage of tumor, and other mechanistic factors not yet identified (Cole, S. W., et al., Nature Reviews, 2015, 15: 563-572). While adjuvant therapy using a β-blocker in certain cancer patients may be potentially beneficial, this therapy is limited in its ability to address all effects of SNS activation on cancer and in all regions of the body. Particular limitations may relate to effects of SNS on cancer progression through non-β-adrenergic receptor routes. For example, some studies have shown that SNS activation of the $\alpha_2$-adrenergic receptor in stromal cells can promote breast tumor progression (Szpunar, M. J., et al., Cancer Prev Res, 2013, 6: 1262-1272). Additional limitations to β-blocker therapy regimes include obstructed or limited access of a systemically circulating pharmaceutical agent to tumor cells, and especially in more progressed tumor environments. As discussed earlier, vasculature of malignant tumors can have enhanced permeability resulting in a leaking effect in and around the tumor which can preclude drug access to cellular targets in the tumor microenvironment. Furthermore, TAMs and other inflammatory cells and byproducts can create a tissue protective response within and around the tumor, making penetration of pharmaceutical agents more challenging and less efficient. Interestingly, conventional cancer therapies, such as surgery, chemotherapy and radiation, can induce local or systemic inflammation triggered by tissue injury and cancer cell death (Grivennikov, S. I., et al., Cell, 2010, 140:883-899), which in turn triggers an inflammatory reaction analogous to a wound-healing response further heightening the challenges associated with effective drug delivery. Additional drawbacks to use of β-adrenergic antagonists for treating a patient with cancer is the possibility of adverse reactions associated with β-adrenoreceptor blockade (e.g., heart failure, hypotension, bradycardia, depression, insomnia, sexual dysfunction, etc.), risks associated with β-blocker intoxication (e.g., death), and management of contraindications (e.g., concomitant use with al-adrenergic antagonists, calcium channel blockers, and other pharmaceutical cardiovascular interventions) on a patient-by-patient basis. Various aspects of the present technology address SNS effects on cancer progression while overcoming these challenges.

II. Neuromodulation for Treatment of Cancer

While sympathetic drive regulation can have adaptive utility in maintaining homeostasis or in preparing many organs in the body for a rapid response to environmental factors, chronic activation of the SNS (e.g., due to chronic stress) can drive the progression of cancer including, for example, tumor progression and/or metastasis. Several embodiments of the present technology utilize intravascular devices that reduce sympathetic nerve activity by applying, for example, radiofrequency (RF) energy to target nerve(s) or target site(s) in patients presently diagnosed with cancer, such as a primary malignant tumor or a hematological cancer. In other embodiments, neuromodulation is used to reduce sympathetic nerve activity of an organ or other tissue structure in patients having a high cancer risk (e.g., a predisposition or increased likelihood of developing cancer), a pre-cancerous lesion, or, in further embodiments, in patients having completed treatment for cancer and/or in remission from a previously treated cancerous condition.

Neuromodulation is the partial or complete incapacitation or other effective disruption of nerves innervating the body's tissues and viscera. In particular, neuromodulation can include inhibiting, reducing, and/or blocking neural communication along target neural fibers (i.e., efferent and/or afferent nerve fibers). Such incapacitation can be long-term (e.g., permanent or for periods of months, years, or decades) or short-term (e.g., for periods of minutes, hours, days, or weeks). While long-term disruption of the target nerves can be desirable for treating cancer patients and other sequelae associated with chronic stress over longer periods of time, short-term modulation of the target nerves may also be desirable. For example, some patients may benefit from short-term modulation to address the effects of cancer progression, such as adjuvant therapy to increase effectiveness of co-administered chemotherapy drugs.

As discussed in greater detail below, neuromodulation of one or more nerve structures associated with tissue proximate a primary malignant tumor and/or that control a function of an organ comprising the primary malignant tumor can include rendering neural fibers inert, inactive, or otherwise completely or partially reduced in function. This result can be electrically-induced, thermally-induced, or induced by another mechanism (e.g., chemically-induced) during a neuromodulation procedure, e.g., a procedure including percutaneous transluminal intravascular access.

In accordance with several aspects of the present technology, neuromodulation is used for the treatment of several forms of cancer. Non-limiting examples of forms of cancers that may be treated using neuromodulation of targeted SNS neural fibers include carcinoma, lymphoma, blastoma, sarcoma, and leukemia. More particular examples of such cancers may include, but are not limited to, breast cancer, small-cell lung cancer, non-small cell lung cancer, abdominal cancers (e.g., stomach, gastrointestinal, liver, renal/kidney, adrenal, pancreatic, colorectal, cancer of the bile duct or gall bladder, etc.), cancers associated with female reproductive organs (e.g., ovarian, uterine, cervical, endometrial, vaginal, vulvar), cancers associated with male reproductive organs (e.g., prostate, scrotal, testicular, penile), skin cancers (e.g., squamous cell cancer, melanoma, etc.), other pelvic cancers (e.g., bladder, ureter, urethral, anal), brain cancers (e.g., glioblastoma, astrocytoma, etc.), thyroid cancer, esophageal cancer, various types of head and neck cancer (e.g., salivary gland carcinoma, oral cavity, sinus and nasal cavity, pharynx, larynx, etc.), bone cancers such as osteosarcoma, and hematopoietic and lymphoid malignancies (e.g., leukemia, lymphoma, multiple myeloma).

As used herein, "metastatic cancer" refers to a cancer that had the potential to, or has begun to, spread to other areas of the body. A variety of cancers can metastasize, however, common metastasizing cancers include breast, lung, melanoma, colon, pancreatic, liver, renal, cervical, multiple myeloma, thyroid and prostate cancers. For some cancer types (e.g., primary cancer), there are common sites of metastases. For example, breast cancer commonly metastasizes to bone tissue, the liver, lung or the brain. The liver is also a common site for ovarian, colorectal, pancreatic metastasis. In a further example, lung cancer commonly metastasizes to the adrenal glands, the brain and to bone tissue. In some embodiments, SNS nerve fibers innervating one or more of these common or likely secondary metastasis sites (e.g., tissues or organs) can also be targeted for neuromodulation to attenuate neural traffic along the sympathetic nerves, for example, to decrease a rate of colonization of circulating tumor cells at the secondary tissue site.

As at least some of the effects of SNS activation take place early in cancer progression, and in one embodiment, neuromodulation treatment can be used in patients having a high cancer risk to reduce a) systemic plasma levels of norepinephrine from, e.g., spillover from innervation of smooth muscle surrounding blood vessels and b) localized levels of norepinephrine in strategic locations (e.g., tissue regions or organs presenting high cancer risk to a patient). In one embodiment, a patient having a pre-cancerous lesion or having other factors presenting an increased risk of developing a precancerous or cancerous lesion in a tissue region or organ can be treated with renal neuromodulation to reduce a level of renal sympathetic drive and/or reduce a level of systemic norepinephrine spillover in circulating plasma (Schlaich, M. P., et al., *Frontiers in Physiology,* 2012, 3(10): 1-7). In some embodiments, a patient having a precancerous lesion or condition can have cells having a disordered morphology such as dysplasia or benign neoplasia. In other embodiments, pre-cancer can refer to patients having been diagnosed with carcinoma in situ (e.g., an early stage, non-invasive cancer). Non-limiting examples of pre-cancerous conditions include ductal carcinoma in situ, atrophic gastritis, cervical dysplasia, leukoplakia, erythroplakia, Barrett's esophagus, adenomatous polyps (without or without additional risk factors), A patient presenting a high or increased cancer risk can include patients having a family history of cancer, patients with history of smoking, patients exposed to high radiation levels (e.g., ionizing radiation, ultraviolet radiation), patients exposed to mutagenic compounds (e.g., asbestos), patients diagnosed with an oncovirus infection (e.g., hepatitis C, hepatitis B, human papilloma virus, Kaposi's sarcoma-associated herpesvirus, human T-lymphotropic virus, etc.) without or without other high risk factors. In other embodiments, a patient presenting a high cancer risk can have a genetic disorder or determined genetic pre-disposition to developing cancer. For example, a cancer syndrome is a genetic disorder in which family-inherited genetic mutations in one or more genes can predispose the affected individuals to the development of particular cancers. These genetic disorders may also cause the early onset of these cancers, and in some cases present a high risk of developing independent primary tumors. Non-limiting examples of inherited cancer-causing syndromes/genetic disorders include hereditary breast-ovarian cancer syndromes, Lynch syndrome (hereditary nonpolyposis colorectal cancer), Fanconi anemia, familial adenomatous polyposis, hereditary paraganglioma-pheochromocytoma syndrome, Li-Faumeni syndrome, MUTYH-associated polyposis, Von Hippel-Lindau disease, and Xeroderma pigmentosum.

Referring back to FIG. 3, the major plexuses of the SNS are aggregations of nerves and ganglia, situated in the thoracic, abdominal, and pelvic cavities, and referred to as the cardiac, celiac, and hypogastric plexuses, respectively. These nerve bundles consist not only of sympathetic fibers derived from the ganglia, but also of nerve fibers from the spinal cord, which are conveyed through the white rami communicantes. Sympathetic efferent nerve fibers consist of both shorter, cholinergic preganglionic fibers that synapses with longer, adrenergic postganglionic nerve fibers that travel from the ganglions to the thoracic, abdominal, and pelvic viscera where they release, in most tissues, the catecholamines norepinephrine and epinephrine. The general visceral afferent fibers also travel along the plexus branches originating in the viscera, glands and blood vessels and transmitting sensory signals (e.g., pain, reflex sensation) along the neurons towards the central nervous system. Such organ and/or tissue afferent activity can contribute to central sympathetic tone or drive.

Some aspects of the present technology are generally directed to modulation of one or more nerve structures associated with tissue proximate a primary malignant tumor in the patient and/or at least partially disrupting communication along neural fibers that control a function of an organ comprising a primary malignant tumor in the patient. Certain targeted nerve structures may reside in the thoracic cavity for at least partially inhibiting sympathetic neural activity associated with lung or breast tissues to provide a therapeutic beneficial reduction in one or more measurable physiological parameters corresponding to the progression and/or metastasis of lung and breast cancers, respectively. Other targeted nerve structures may be associated with the abdominal viscera (e.g., stomach, intestine, liver and biliary system, pancreas, spleen, kidneys, ureters, bladder and suprarenal glands) or reproductive organs to reduce or inhibit one or more physiological parameters associated with progression and/or metastasis of a primary malignant tumor associated with these physiological structures.

In many embodiments, modulation of targeted nerves and nerve structures can include modulation of the nerves in locations proximate (e.g., at or near) a percutaneously accessible artery (e.g., superior mesenteric artery, the celiac artery, pulmonary artery, renal artery, ovarian artery, internal thoracic artery, etc.) or vein (e.g., superior mesenteric vein) and/or other suitable structures. Transcatheter delivery systems can position suitable neuromodulation devices within targeted vascular regions percutaneously as described further herein.

Selection of one or more targeted nerve and/or nerve structures can be based on, for example, the physiological location of the primary cancer or primary malignant tumor, the genetic profile of the primary tumor (e.g., specific type of cancer or other distinguishing genetic features), the tumor stage or degree of progression of the primary cancer, and the overall health of the patient among other factors. In one embodiment, treatment can include neuromodulation of one or more nerve structures associated with tissue proximate a primary malignant tumor and/or that control a function of an organ comprising the primary malignant tumor. In other embodiments, treatment for a variety of cancers can include renal neuromodulation to reduce sympathetic renal activity and/or reduce central sympathetic drive (e.g., whole body norepinephrine spillover). In still further embodiments, treatment can include neuromodulation of one or more nerve structures associated with a likely secondary metastasis site, for example, to reduce a rate of colonization of circulating cancer cells at the secondary site. A desirable treatment protocol may include one or more of these neuromodulation treatments in variable combinations on a patient-by-patient basis. Several sympathetic nerve targets, treatment locations, and cancer types/tissue locations are listed below in TABLES 1-3.

A. Thoracic Cavity Nerves and Ganglia

In vertebrates, the thoracic cavity primarily houses the lungs and the major structures of the cardiovascular system (e.g., heart, aorta, pulmonary arteries, etc.). Examples of sympathetic nerve targets within the thoracic cavity are found listed in TABLE 1 and described further herein.

TABLE 1

THORACIC CAVITY NERVES AND GANGLIA

| Nerve Target | Intravascular/Intraluminal Treatment Location | Cancer Type/Location |
|---|---|---|
| Pulmonary plexuses | Pulmonary artery/vein, Esophagus | Decrease local sympathetic drive to treat lung cancer |
| Internal mammary plexus (derived from the subclavian plexus) | Internal thoracic artery (i.e., internal mammary artery) | Decrease local sympathetic drive to breast parenchyma to treat breast cancer |

1. Sympathetic Pulmonary Nerves

Figure 4:
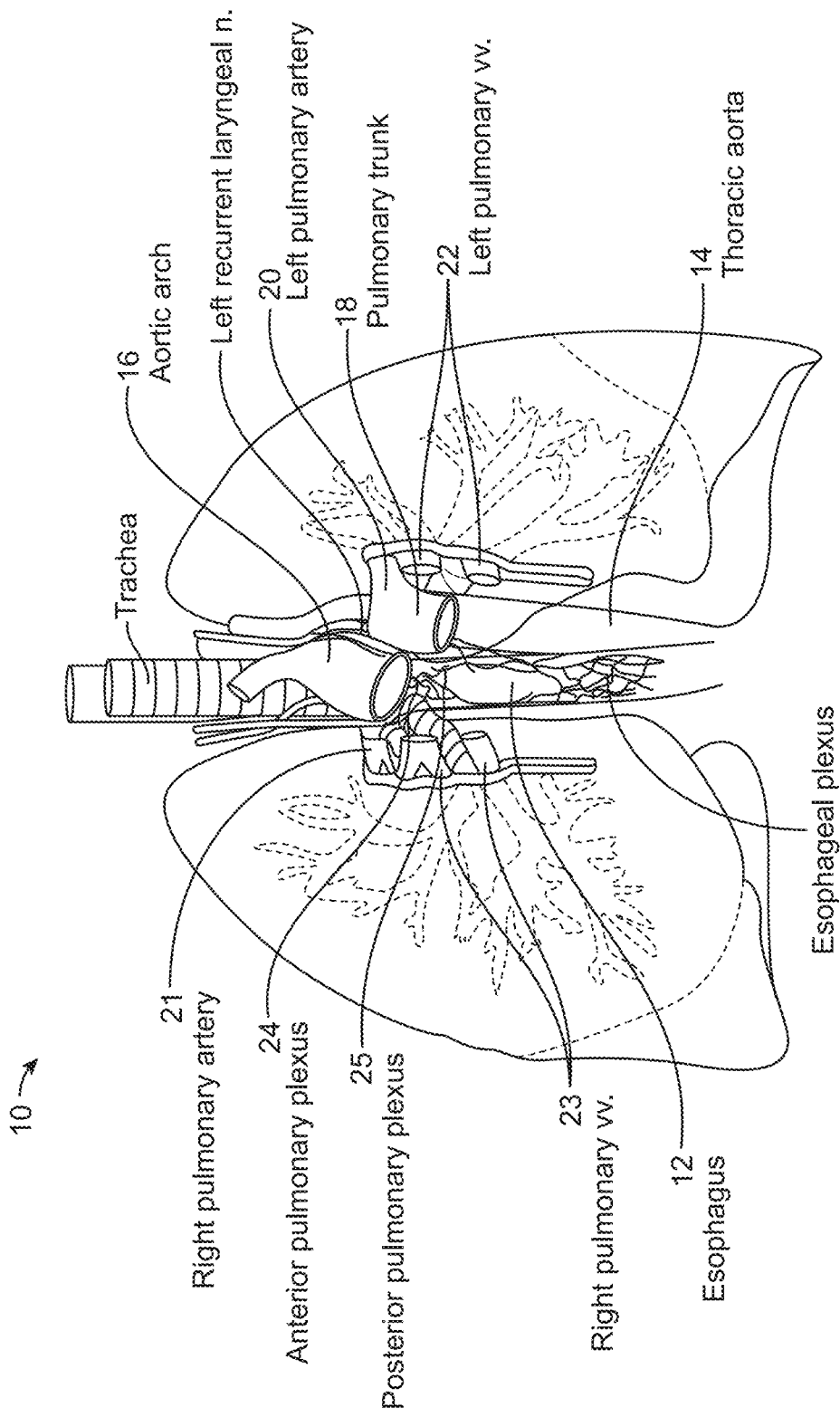
FIG. 4 is an enlarged anatomical view illustrating the lungs and SNS nerves associated with the anterior and posterior pulmonary plexus surrounding the pulmonary arteries.

In one embodiment, modulation of one or more SNS fibers associated with the pulmonary plexus is used to therapeutically reduce one or more physiological parameters associated with progression of lung cancer. The sympathetic nerves arising from primarily the thoracic spine (i.e., levels T1-T10) with potential contribution from the cervical spine, innervate the heart and the lung after branching out from the thoracic sympathetic chain ganglia. FIG. 4 is an anatomical view illustrating the lungs 10, esophagus 12 and the major arterial vessels including, for example, the thoracic aorta 14, the aortic arch 16, the pulmonary trunk 18, the left and right pulmonary arteries 20, 21, and the left and right pulmonary veins 22, 23. The anterior and posterior pulmonary plexuses 24, 25 (referred to together as pulmonary plexus) are the sites of convergence of autonomic fibers which supply the lung 10 and are in close proximity to the pulmonary arteries 20, 21.

In accordance with an embodiment of the present technology, neuromodulation (e.g., decreasing activity) of at least one sympathetic nerve innervating one or more of the pulmonary trunk 18, the left or right pulmonary arteries 20, 21, or branches thereof within a patient is anticipated to be therapeutically beneficial for treating lung cancer. In some instances, neuromodulation of the pulmonary plexus 24, 25 or one or more nerve fibers thereof can be achieved via application of a suitable treatment modality, e.g., cryotherapeutic, direct heat, electrode-based, transducer-based, chemical-based, or another suitable treatment modality within a target vessel as described above, or in another embodiment, within the esophagus 12.

In some embodiments, reducing sympathetic tone innervating the pulmonary vasculature may be useful for reducing at least one of a primary malignant tumor growth rate in the lung, a primary malignant tumor size in the lung, a degree of vascularization of a primary malignant tumor in the lung and/or a number circulating tumor cells. In other embodiments, reducing sympathetic neural activity in the pulmonary plexus can include improving an effectiveness of chemotherapy drugs on tumor cells in the patient. In yet a further embodiment, neuromodulation of the pulmonary plexus may be beneficial in decreasing a rate of colonization of circulating tumor cells in the lungs of patients having a primary cancer distal to the lungs (e.g., breast cancer, pancreatic cancer).

2. Sympathetic Breast Tissue Nerves

In another embodiment, neuromodulation of at least a portion of the internal mammary plexus, which is derived from the subclavian plexus, can decrease local sympathetic drive to breast parenchyma to reduce one or more physiological parameters associated with the progression and/or metastasis of breast cancer. FIG. 5 a partial anatomical view illustrating the arterial supply to the breast tissue 30. As illustrated, blood flow to the breast tissue is provided by the internal thoracic artery 32 and branches 33 thereof via the subclavian artery 34, and by the lateral thoracic artery 36 and branches thereof via the axillary artery 38. The internal mammary plexus (not shown) is intimately associated with the internal thoracic artery 32.

In accordance with an aspect of the present technology, neuromodulation of the internal mammary plexus can effectively reduce sympathetic tone to the breast tissue. A neuromodulation treatment device (not shown) can be used to apply a suitable treatment modality, e.g., cryotherapeutic, direct heat, electrode-based, transducer-based, chemical-based, or another suitable treatment modality within internal thoracic artery 32 for treating breast cancer. In some embodiments, reducing sympathetic tone of breast tissue may be useful for reducing at least one of a malignant breast tumor growth rate, a malignant breast tumor size, a degree of vascularization of a malignant breast tumor and/or a number of invasive or circulating breast tumor cells. In other embodiments, reducing sympathetic neural activity in the internal mammary plexus may include improving an effectiveness of chemotherapy agents on breast tumor cells in the patient.

B. Abdominal Cavity Nerves and Ganglia

The abdominal cavity is a large body cavity that contains many organs and abdominal viscera. Particular embodiments of the present technology are directed to neuromodulation of at least a portion of the superior mesenteric plexus, the celiac plexus, the renal plexus, and/or the hepatic plexus to therapeutically reduce one or more physiological parameters associated with progression of cancer associated with the pancreas, kidney, liver or other abdominal organ systems. Other aspects of the present technology are directed to renal neuromodulation to reduce/inhibit/decrease central sympathetic tone or drive in the body to provide a therapeutic reduction in one or more measurable physiological parameters corresponding the progression of cancer in the patient. In yet further embodiments, immune system neuromodulation is used to therapeutically reduce mechanisms of inflammation and/or modulate a tumor-related immune response. Examples of sympathetic nerve targets within the abdominal cavity are found listed in TABLE 2 and described further herein.

ganglia) and interconnecting fibers. The celiac plexus includes a number of smaller plexuses, such as the hepatic plexus, splenic plexus, gastric plexus, pancreatic plexus and suprarenal plexus. The celiac plexus is also known to transmit pain sensation originating from the pancreas as well as most of the abdominal viscera with the exception of the colon, rectum and pelvic organs to the thalamus and cortex of the brain (Levy et. al. *Gastrointestinal Endoscopy Clinics of North America*. 2012; 22: 231-47, viii). A ganglion is defined as a collection of nerve cell bodies and glial cells that are interconnected via a sense network of neural rami and septae of connective tissue. The celiac ganglia can be detected, for example, using endoscopic ultrasound or other techniques (e.g., CT, fluoroscopy). For example, visualized ganglia are typically located adjacent to the celiac artery, anterior to the aorta, and are predominantly oval or almond-shaped, ranging in size from 2 to 20 mm.

TABLE 2

ABDOMINAL CAVITY NERVES AND GANGLIA

| Nerve Target | Intravascular/Intraluminal Treatment Location | Cancer Type/Location |
|---|---|---|
| Celiac plexus | Celiac artery | Decrease local sympathetic drive to treat cancer in abdominal viscera (e.g., pancreatic cancer, liver cancer, bile duct cancer and gallbladder cancer, leukemia, lymphoma, stomach cancer, small intestine cancer, colorectal cancer, kidney cancer) |
| Renal plexus/Renal nerve | Renal artery/ostium/vein | 1) Decrease renal sympathetic drive to treat renal cancer (e.g., renal cell carcinoma, transitional cell cancer, renal sarcoma, Wilms tumor); 2) Decrease central sympathetic drive to treat all cancer types (e.g., primary malignant tumor located in any tissue, leukemia, lymphoma, etc.) |
| Afferent renal nerves | Renal pelvis, Renal calxy (e.g., through ureter) | Decrease central sympathetic drive to treat all cancer types |
| Efferent renal nerves | Renal artery and/or the renal branch arteries near the renal parenchyma | 1) Decrease renal sympathetic drive to treat renal cancer (e.g., renal cell carcinoma, transitional cell cancer, renal sarcoma, Wilms tumor); 2) Decrease central sympathetic drive to treat all cancer types (e.g., primary malignant tumor located in any tissue, leukemia, lymphoma, etc.) |
| Superior mesenteric plexus | Superior mesenteric artery/vein | Decrease local sympathetic drive to treat pancreatic cancer, small intestine cancer and colorectal cancer |
| Hepatic plexus | Hepatic artery | Decrease local sympathetic drive to treat liver cancer, bile duct cancer and gallbladder cancer |
| Splenic plexus | Splenic artery/vein, Splenic branch arteries | 1) Decrease local sympathetic drive to treat leukemia and lymphoma; 2) Decrease local sympathetic drive to spleen to treat primary malignant tumors in other tissues to minimize TAM recruitment to tumor microenvironment |
| Gastric plexus | Left gastric artery, Superior mesenteric artery/vein, Inferior mesenteric artery/vein | Decrease local sympathetic drive to treat gastrointestinal cancers (e.g., stomach cancer, small intestine cancer, colorectal cancer) |
| Pancreatic plexus | Splenic artery, Pancreatic arteries | Decrease pancreatic sympathetic drive to treat pancreatic cancer |

1. Sympathetic Nerves of the Abdominal Viscera

The celiac plexus is a complex network of nerves located in the abdomen, where the celiac artery, superior mesenteric artery, and renal arteries branch from the abdominal aorta. The celiac plexus is located caudal to the diaphragm (in an antecrural position), surrounds the origin of the celiac trunk, and comprises a dense network of ganglia (e.g., celiac Neuromodulation of the celiac plexus and/or the celiac ganglia is the partial or complete incapacitation or other effective disruption or regulation of nerves innervating the pancreas, e.g., nerves terminating in or originating from the pancreas or in structures closely associated with the pancreas) and/or nerves innervating the liver, gallbladder, stomach, spleen, kidney, small intestine, ascending and transverse colon and the ovarian theca, respectively. In particular, neuromodulation of the celiac plexus comprises inhibiting, reducing, blocking, pacing, up-regulating, and/or down-regulating neural communication along neural fibers (e.g., efferent and/or afferent neural fibers) innervating the pancreas, or in other embodiments, innervating the liver, gallbladder, and other abdominal organs. In other embodiments, the treatment procedure can target a subset of nerves of a smaller plexus within the celiac plexus, such as the hepatic plexus (e.g., along the hepatic artery), the splenic plexus (e.g., along the splenic artery), the gastric plexus (e.g., along the left gastric artery), and the pancreatic plexus (e.g., along the pancreatic artery). These targets can be intravenously accessed through femoral, brachial or radial approaches where a catheter could be navigated through the celiac trunk to the subsidiary arteries (e.g., hepatic, splenic, pancreatic, etc.). Such incapacitation, disruption, and/or regulation can be long-term (e.g., permanent or for periods of months, years, or decades) or short-term (e.g., for periods of minutes, hours, days, or weeks).

Neuromodulation of the celiac plexus and/or the celiac ganglia is expected to be useful in reducing various physiological parameters associated with the progression of these diseases. Methods and systems for neuromodulation of the celiac plexus and/or celiac ganglia for efficaciously treating and/or reducing one or more physiological parameters associated with cancer progression (e.g., tumor growth, tumor vascularization, metastasis, etc.) of the abdominal viscera are described herein.

Sympathetic neural activity via the nerve fibers of the celiac plexus and/or celiac ganglion, and particularly general visceral afferent nerves, are responsible for carrying pain signals as well as other sensory impulses such as reflex sensations from the abdominal viscera to the brain in patients e.g., patients with pancreatic cancer, stomach cancer, liver cancer, bile duct cancer and gallbladder cancer, small intestine cancer, colon cancer, kidney cancer, etc., which can in turn increase central sympathetic activity. As such, afferent sympathetic activity (e.g., pancreatic, hepatic, gastric, splenic, renal, colon, etc.) can contribute to central sympathetic tone or drive. Accordingly, neuromodulation of the celiac plexus and/or celiac ganglia is expected to be useful in treating cancer in a variety of viscera by lowering central sympathetic activity, particularly when central sympathetic activity is overactive or hyperactive (e.g., in conditions associated with central sympathetic overstimulation such as chronic stress). Accordingly, in some patients, reducing localized sympathetic drive via the celiac plexus and/or celiac ganglia, central sympathetic drive, and/or other benefits from neuromodulation can outweigh the complete or partial loss of nerve functionality in targeted organs.

The superior mesenteric plexus is a continuation of the lower part of the celiac plexus. The superior mesenteric plexus surrounds the superior mesenteric artery and divides into a number of secondary plexuses and/or gives rise to sympathetic nerve fibers innervating the pancreas, the small intestine, and colon in the abdomen. The superior mesenteric ganglion is the synapse point for one of the pre- and post-synaptic nerves of the sympathetic division of the autonomous nervous system. Specifically, contributions to the superior mesenteric ganglion arise from TV10 and TV11, and these nerve fibers go on to innervate the small intestine, the ascending colon and the transverse colon.

Neuromodulation of the superior mesenteric plexus and/or the superior mesenteric ganglia is the partial or complete incapacitation or other effective disruption or regulation of nerves innervating the pancreas, e.g., nerves terminating in or originating from the pancreas or in structures closely associated with the pancreas) and/or nerves innervating the small intestine, and ascending and transverse colon. In particular, neuromodulation of the superior mesenteric plexus comprises inhibiting, reducing, blocking, pacing, up-regulating, and/or down-regulating neural communication along neural fibers (e.g., efferent and/or afferent neural fibers) innervating the pancreas, or in other embodiments, innervating the small intestine, and ascending and transverse colon. Such incapacitation, disruption, and/or regulation can be long-term (e.g., permanent or for periods of months, years, or decades) or short-term (e.g., for periods of minutes, hours, days, or weeks).

Neuromodulation of the superior mesenteric plexus and/or the superior mesenteric ganglia is expected to be useful in treating cancer associated with the pancreas, small intestine, and ascending and transverse colon as well as pain associated with cancer. In particular, neuromodulation of the superior mesenteric plexus and/or the superior mesenteric ganglia is also expected to be useful in treating cancer in a variety of viscera by lowering central sympathetic activity (e.g., particularly in conditions associated with central sympathetic overstimulation such as chronic stress). Methods and systems for neuromodulation of the celiac plexus and/or celiac ganglia, the superior mesenteric plexus and/or the superior mesenteric ganglia for efficaciously treating cancer of the abdominal viscera, are further described herein.

Figure 6A:
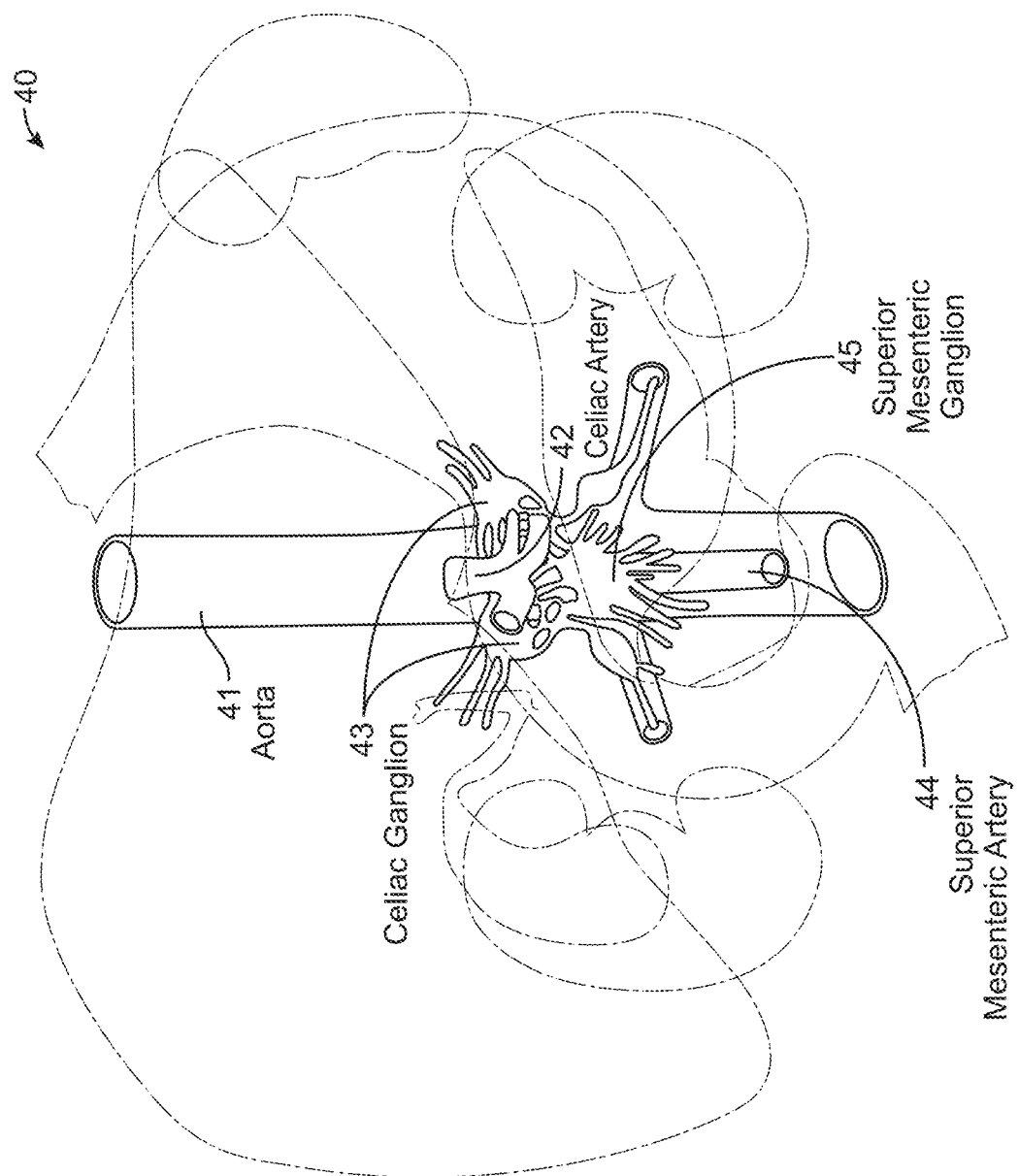
FIGS. 6A-6B are anatomical views illustrating the abdominal viscera and the nearby nerve structures and vessels.
Figure 6B:
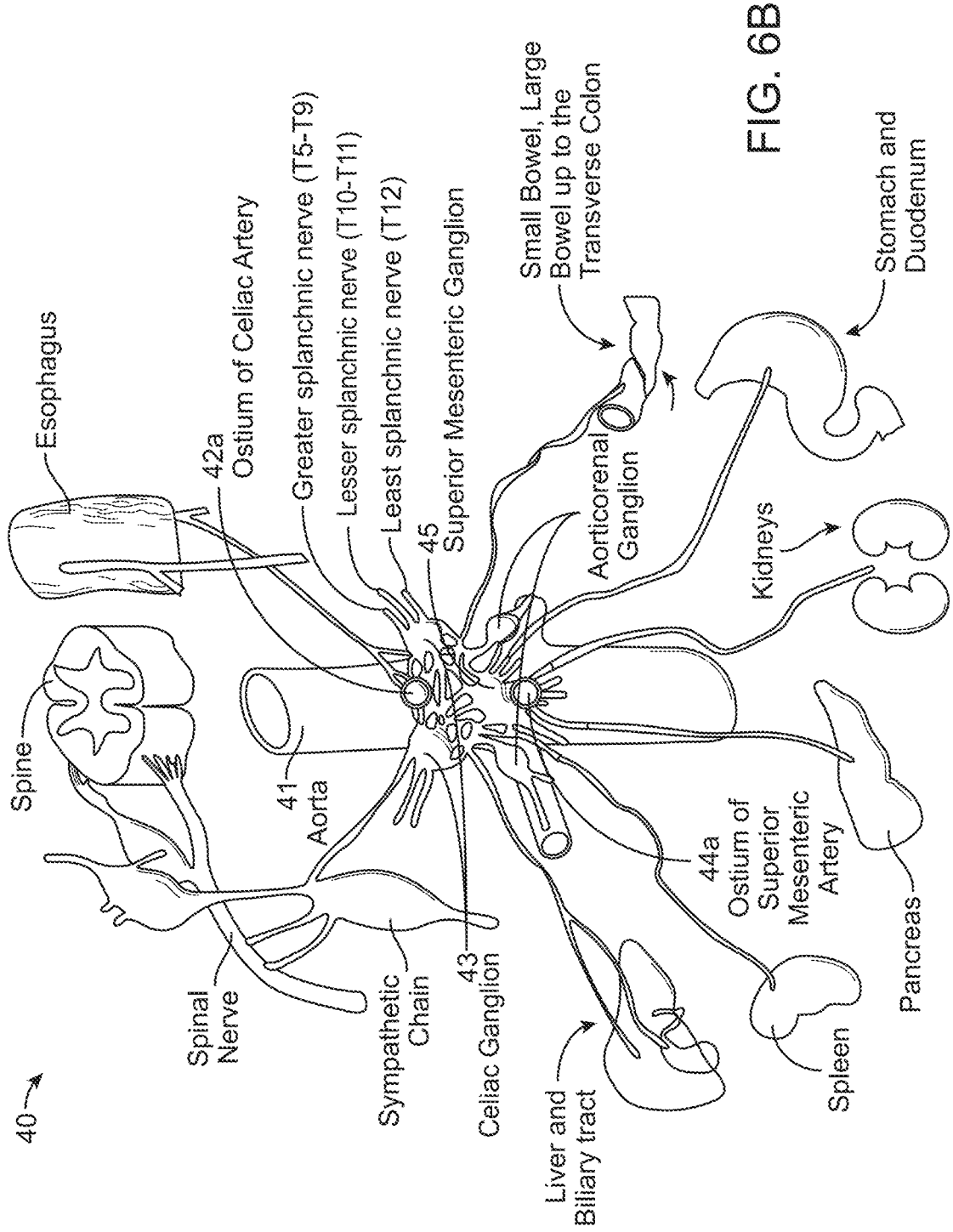

FIGS. 6A and 6B are anatomical views illustrating the abdominal viscera 40 and the major arterial vessels including, for example, the aorta 41, the celiac artery 42 and the superior mesenteric artery 44. FIGS. 6A and 6B also illustrate the sympathetic nerve structures that innervate the abdominal viscera 40, including the celiac plexus and/or celiac ganglion 43, and the superior mesenteric plexus and/or ganglion 45. Treatment procedures for neuromodulation in accordance with embodiments of the present technology can include applying a treatment modality at one or more treatment locations proximate a structure having a relatively high concentration of sympathetic nerves innervating a diseased (e.g., comprising a primary malignant tumor) or otherwise abnormal or targeted organ (e.g., an organ having a high cancer risk, a pre-cancerous lesion, or having been previously treated for cancer). In some embodiments, for example, at least one treatment location can be proximate a portion of the celiac artery 42, a branch of the celiac artery 42, an ostium of the celiac artery 42a, and/or another suitable structure (e.g., another suitable structure in close association the celiac plexus and/or celiac ganglion 43) in the vicinity of celiac sympathetic nerves. In other embodiments, at least one treatment location can be proximate a portion of the superior mesenteric artery 44, a branch of the superior mesenteric artery 44, an ostium of the superior mesenteric artery 44a, a superior mesenteric vein (not shown), and/or another suitable structure (e.g., another suitable structure in close association the superior mesenteric ganglion 45) in the vicinity of superior mesenteric sympathetic nerves.

Figure 6C:
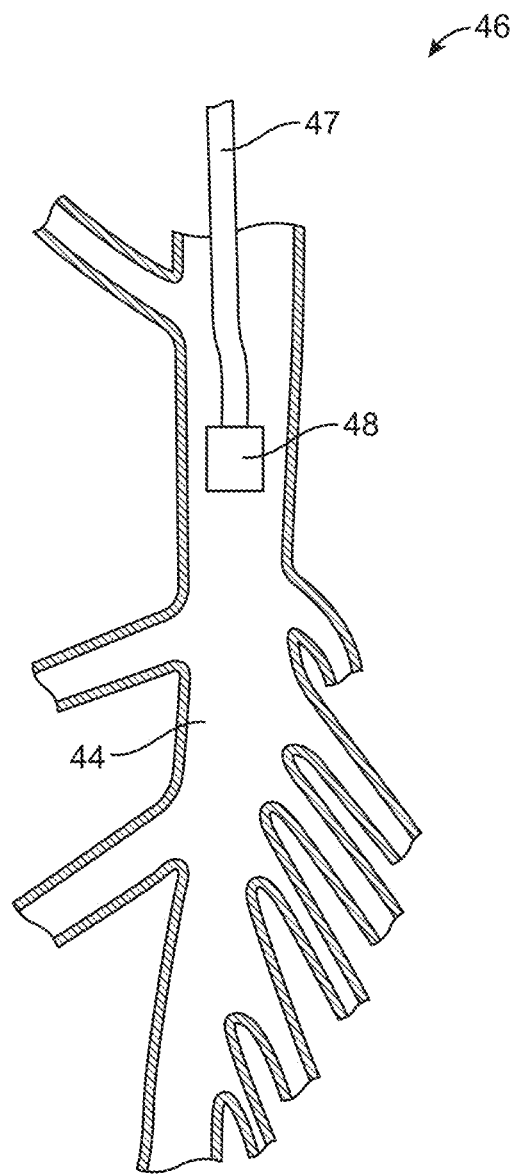
FIG. 6C is a partially cross-sectional view illustrating neuromodulation at a treatment location within the superior mesenteric artery in accordance with an embodiment of the present technology.

FIG. 6C, for example, is a cross-sectional view illustrating neuromodulation at a treatment location within the superior mesenteric artery 44. As shown in FIG. 6C, a treatment device 46 including a shaft 47 and a therapeutic element 48 can be extended toward the superior mesenteric artery 44 to locate the therapeutic element 48 at the treatment location within the superior mesenteric artery 44. The therapeutic element 48 can be configured for neuromodulation at the treatment location via a suitable treatment modality, e.g., cryotherapeutic, electrode-based, transducer-based, chemical-based, or another suitable treatment modality.

Likewise, the treatment device 46 can be located at a treatment location within the celiac artery 42 (FIG. 6A) for administering neuromodulation. In other embodiments, administering neuromodulation can include administering a suitable treatment modality at more than one site, e.g., the celiac artery 42 and the superior mesenteric artery 44, for example for modulating the sympathetic nerves innervating the pancreas or other abdominal organ.

Neuromodulation of the hepatic plexus, splenic plexus, gastric plexus and pancreatic plexus can be achieved via intravascular access to the hepatic artery, splenic artery, left gastric artery and pancreatic arteries, via access from the celiac trunk, if desired.

2. Sympathetic Renal Nerves

Figure 7:
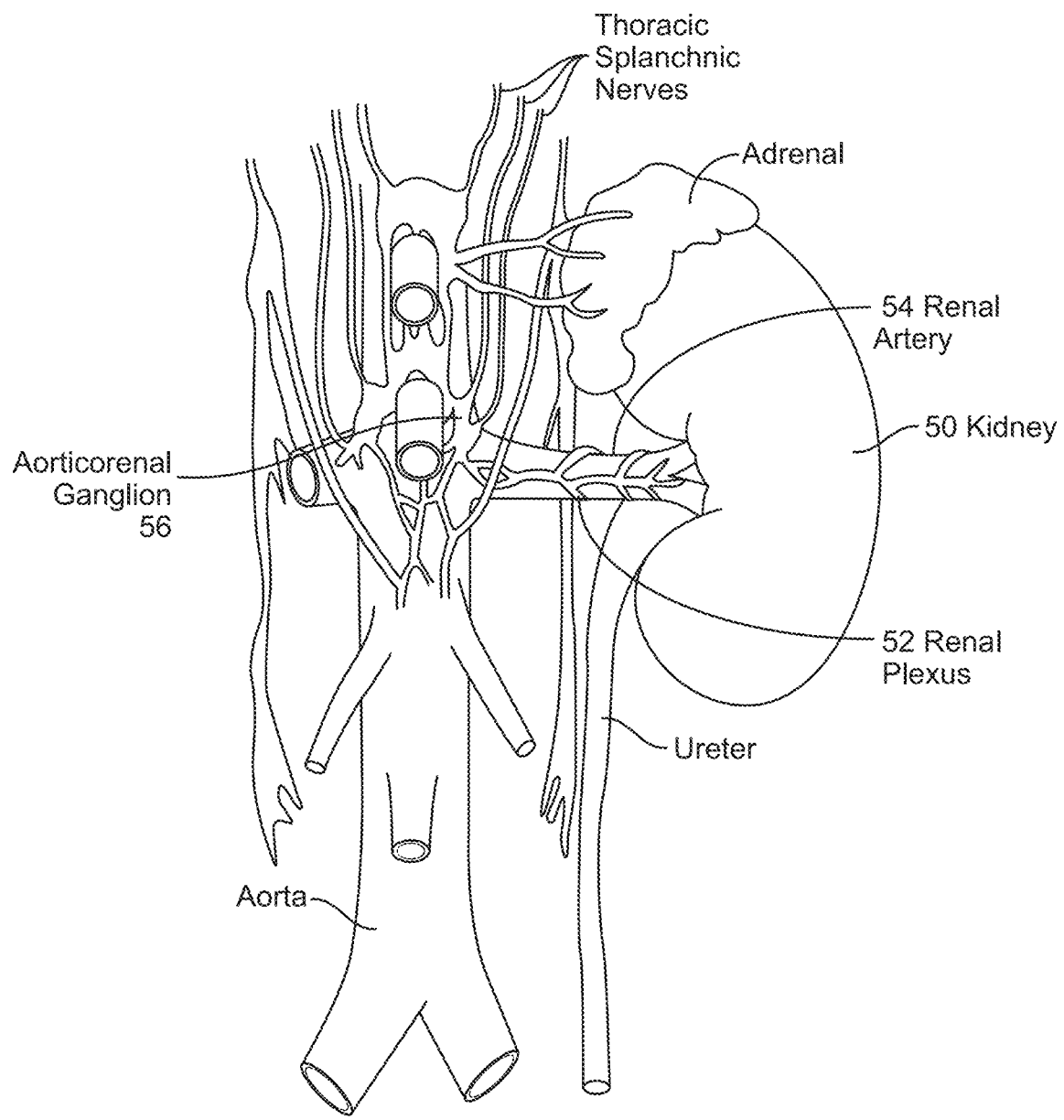
FIG. 7 is an enlarged anatomic view of nerves of a left kidney to form the renal plexus surrounding the left renal artery.

FIG. 7 is an enlarged anatomic view of nerves of innervating a left kidney 50 of a patient. As FIG. 7 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidneys while terminating in the blood vessels, the juxtaglomerular apparatus, and the renal tubules (not shown). Fibers contributing to the renal plexus 52 arise from the celiac ganglion 43 (FIGS. 6A and 6B), the superior mesenteric ganglion 45 (FIGS. 6A and 6B), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 3). Referring to FIGS. 3, 6A, 6B and 7 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion 43, the superior mesenteric ganglion 45, and the aorticorenal ganglion 56. Postganglionic neuronal cell bodies exit the celiac ganglion 43, the superior mesenteric ganglion 45, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. As provided herein, renal neuromodulation is likely to be valuable in the treatment of kidney cancer such as, for example, renal cell carcinoma, transitional cell cancer, renal sarcoma and Wilms tumor among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of kidney cancer progression. Renal neuromodulation is also likely to be particularly valuable in the treatment of cancer in patients having one or more clinical conditions characterized by increased overall and particularly renal sympathetic activity such as hypertension, metabolic syndrome, insulin resistance, diabetes, among others.

As the reduction of afferent neural signals contributes to the systemic reduction of sympathetic tone/drive, renal neuromodulation might also be useful in treating cancers found throughout the body. For example, a reduction in central sympathetic drive may reduce the incidence of metastasis and/or improve another measurable physiological parameter associated with the progression of cancer, such as reducing at least one of a primary malignant tumor growth rate, a primary malignant tumor size, a degree of vascularization of a primary malignant tumor and/or a number circulating tumor cells. In other embodiments, reducing sympathetic neural activity in the renal nerve and/or reducing central sympathetic drive can include improving an effectiveness of chemotherapy drug on tumor cells in the patient. In a particular example, a reduction in central sympathetic drive may reduce a level of TAMs present in the tumor stroma and/or an overall level of inflammation present in the microenvironment of the tumor, thereby allowing chemotherapeutic agents access to tumor cells that would otherwise be protected by various inflammatory cells (e.g., TAMs).

3. Sympathetic Nerves of the Immune System

Immune system neuromodulation is the partial or complete incapacitation or other effective disruption or regulation of immune system nerves, e.g., nerves terminating in or originating from one or more immune system organs (including, but not limited to, the spleen, lymph nodes, bone marrow, thymus, and other suitable organs) or in structures closely associated with the immune system organs. In particular, immune system neuromodulation comprises inhibiting, reducing, blocking, pacing, upregulating, and/or downregulating neural communication along neural fibers (e.g., efferent and/or afferent neural fibers) innervating one or more immune system organs. Such incapacitation, disruption, and/or regulation can be long-term (e.g., permanent or for periods of months, years, or decades) or short-term (e.g., for periods of minutes, hours, days, or weeks). While long-term disruption of the immune system nerves can be desirable for alleviating symptoms and other sequelae associated with hematopoietic cancers and other cancers throughout the body (e.g., to reduce a tumor-associated inflammatory response, etc.) over longer periods of time, short-term modulation of the immune system nerves may also be desirable, for example, to generate a temporary reduction in immune system function to treat a patient.

Furthermore, afferent sympathetic activity from immune system organs can contribute to central sympathetic tone or drive. Accordingly, immune system neuromodulation is expected to be useful in treating cancer in a manner that reduces central sympathetic activity, particularly in conditions with central sympathetic overstimulation such as chronic stress.

Potential targets for immune system neuromodulation include nerves innervating immune system organs such as the spleen, thymus, and lymph nodes. Among the immune system organs, the spleen can be a particularly well-suited target for neuromodulation when treating cancer, a precancerous condition, or in patients with a high risk of developing cancer. In addition to acting as a blood filter and blood reserve, the spleen contains in its blood reserves half of the body's monocytes, which can mature into macrophages via β-adrenergic signaling and be recruited to the tumor site as TAMs.

Figure 8A:
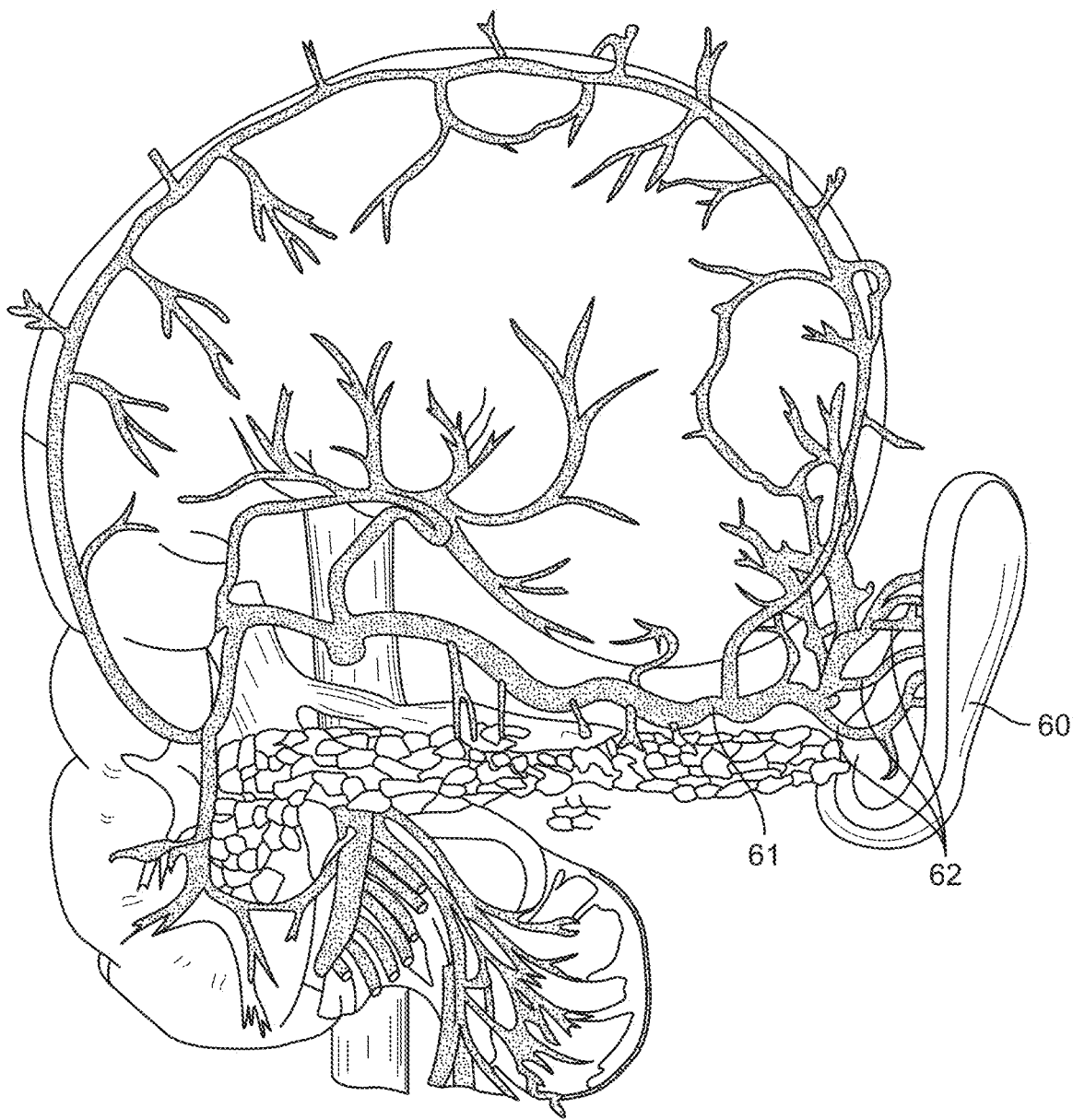
FIG. 8A is an anatomical view illustrating abdominal organs of a human patient, including a spleen, a splenic artery, and nearby organs and vessels.

FIG. 8A is an anatomical view illustrating the abdominal organs, including the spleen 60, splenic artery 61, and splenic branch arteries 62. Referring to FIG. 8A, treatment procedures in accordance with embodiments of the present technology can include applying a treatment modality at one or more treatment locations proximate a structure having a relatively high concentration of immune system nerves. In some embodiments, for example, the treatment locations can be proximate portions of the splenic artery 61, an ostium of the splenic artery 61, a splenic branch artery 62, an ostium of a splenic branch artery 62, the splenic vein, an ostium of the splenic vein, or a branch of the splenic vein, another portion of a vessel or duct of an immune system organ, and/or another suitable structure.

Figure 8B:
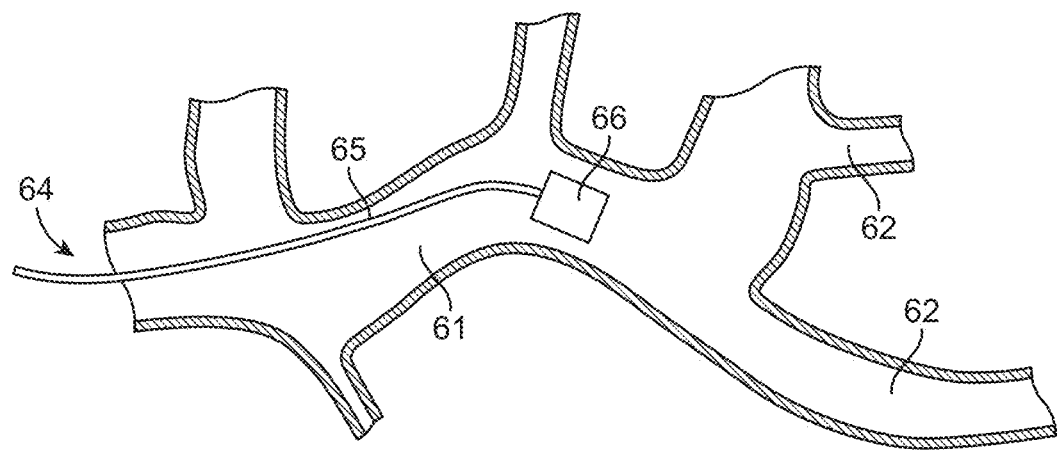
FIGS. 8B and 8C are partially cross-sectional views illustrating neuromodulation at a treatment location within a splenic artery and a splenic branch artery, respectively, and in accordance with an embodiment of the present technology.
Figure 8C:
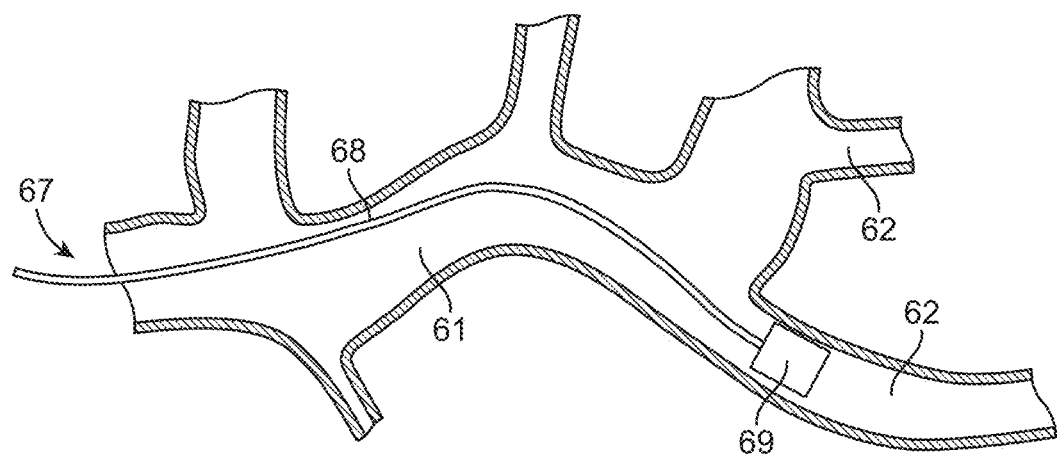

FIGS. 8B and 8C, for example, are cross-sectional views illustrating, respectively, neuromodulation at treatment locations within the splenic artery and a splenic branch artery. As shown in FIG. 8B, a treatment device 64 including a shaft 65 and a therapeutic element 66 can be extended toward the splenic artery 61 to locate the therapeutic element 66 at a treatment location within the splenic artery 61. Similarly, as shown in FIG. 8C, a treatment device 67 can be extended via a shaft 68 toward a splenic branch artery 62 to locate the therapeutic element 69 at a treatment location within the splenic branch artery 62. The therapeutic element 66 or 69 can be configured for neuromodulation at the treatment locations via a suitable treatment modality, e.g., cryotherapeutic, direct heat, electrode-based, transducer-based, chemical-based, or another suitable treatment modality.

C. Pelvic Cavity Nerves and Ganglia

The pelvic cavity is a lower body cavity bounded on the pelvic floor by the pelvic bones, and which contains reproductive organs, the urinary bladder as well as housing the lower portion of the colon and rectum and other interstitial tissues. Particular embodiments of the present technology are directed to modulation of sympathetic nerves innervating male and female reproductive/genital organs to therapeutically reduce one or more physiological parameters associated with progression of cancer associated with the male reproductive system (e.g., prostate, testes, penis) or the female reproductive system (e.g., ovaries, uterus, cervix, vulva, vagina). For example, some embodiments are directed to modulation of at least a portion of the testicular and/or penile sympathetic nerves (e.g., sympathetic nerves along the testicular vessels, pudendal vessels or other associated structures), and/or to modulation of at least a portion of the prostatic plexus, spermatic plexus, the lumbar plexus, the sacral plexus, the uterovaginal plexus, ovarian plexus and/or particular sympathetic nerves innervating the prostate, testes, penis, ovaries, uterus, cervix, vagina and/or vulva (e.g., perineal nerve, ilioinguinal nerve, genitofemoral nerve, pudendal nerve). Other embodiments are directed to modulation of sympathetic nerves (e.g., inferior mesenteric plexus, left colic plexus, sigmoid plexus, superior hemorrhoidal plexus, inferior hypogastric plexus, pelvic plexus, middle rectal plexus, etc.) innervating the urinary bladder, descending and/or sigmoid colon and/or rectum. Examples of sympathetic nerve targets within the pelvic cavity are found listed in TABLE 3 and described further herein.

TABLE 3

PELVIC CAVITY NERVES AND GANGLIA

| Nerve Target | Intravascular/Intraluminal Treatment Location | Cancer Type/Location |
|---|---|---|
| Ovarian plexus/Ovarian nerve | Ovarian artery/vein | Decrease ovarian sympathetic drive to treat ovarian cancer; decrease local sympathetic drive to treat cancer within or proximate the Fallopian tube (uterine tube). |
| Vaginal plexus (derived from inferior hypogastric plexus) | Branches of the internal iliac artery (e.g., vaginal arteries, vaginal venous plexus) | Decrease local sympathetic drive to treat vaginal cancer |
| Uterine plexus (derived from inferior hypogastric plexus) | Uterine artery | Decrease local sympathetic drive to treat uterine cancer or vaginal cancer |
| Prostatic plexus (derived from inferior hypogastric plexus) | Prostatic arteries (derived from the internal iliac artery, the internal pudendal artery and middle rectal arteries), Branches of the internal iliac artery, Rectum | Decrease local sympathetic drive to treat prostate cancer |
| Spermatic plexus | Testicular artery/vein | Decrease local sympathetic drive to treat testicular cancer |
| Genital branch of genitofemoral nerve (Lumbar plexus) | External iliac artery/vein, Testicular vessels | Decrease local sympathetic drive to treat testicular cancer, scrotal cancer, penile cancer, vulvar cancer and vaginal cancer |
| Ilioinguinal nerve (Lumbar plexus) | Deep circumflex iliac artery (or vein) which is a branch of the external iliac artery | Decrease local sympathetic drive to treat scrotal cancer and penile cancer |
| Sacral plexus | Internal iliac artery, Internal iliac vein | Decrease local sympathetic drive to treat male and female reproductive/genital cancers |
| Pudendal nerve (Sacral plexus) | Internal pudendal vessels (artery) | Decrease local sympathetic drive to treat male and female genital cancers |
| Perineal nerve (from pudendal nerve) | Internal pudendal artery | Decrease local sympathetic drive to treat male and female reproductive/genital cancers |

TABLE 3-continued

PELVIC CAVITY NERVES AND GANGLIA

| Nerve Target | Intravascular/Intraluminal Treatment Location | Cancer Type/Location |
|---|---|---|
| Inferior mesenteric plexus | Inferior mesenteric artery, Inferior mesenteric vein | Decrease local sympathetic drive to treat cancer associated with a primary malignant tumor in the pelvic region (urinary bladder cancer, reproductive and genital organ cancers, |
| Vesical plexus | Superior vesical artery, Inferior vesical artery | Decrease local sympathetic drive to treat urinary bladder cancer |
| Left colic plexus, Sigmoid plexus, Superior hemorrhoidal plexus | Branches of the inferior mesenteric artery (e.g., Left colic artery, Sigmoid artery, Superior hemorrhoidal artery) | Decrease local sympathetic drive to treat cancers of the descending and sigmoid colons, and rectal cancer |
| Hypogastric plexus | Internal iliac artery, Internal iliac vein | Decrease local sympathetic drive to treat bladder cancer, prostate cancer and other male and female reproductive/genital cancers |
| Lumbosacral plexus (anterior divisions of the lumbar nerves, sacral nerves, and coccygeal nerve) | Internal iliac artery, Internal iliac vein, the Ureter, Superior gluteal artery and vein | Decrease local sympathetic drive to treat cancer associated with a primary malignant tumor in the pelvic region |

1. Sympathetic Nerves of the Female Reproductive System

Figure 9:
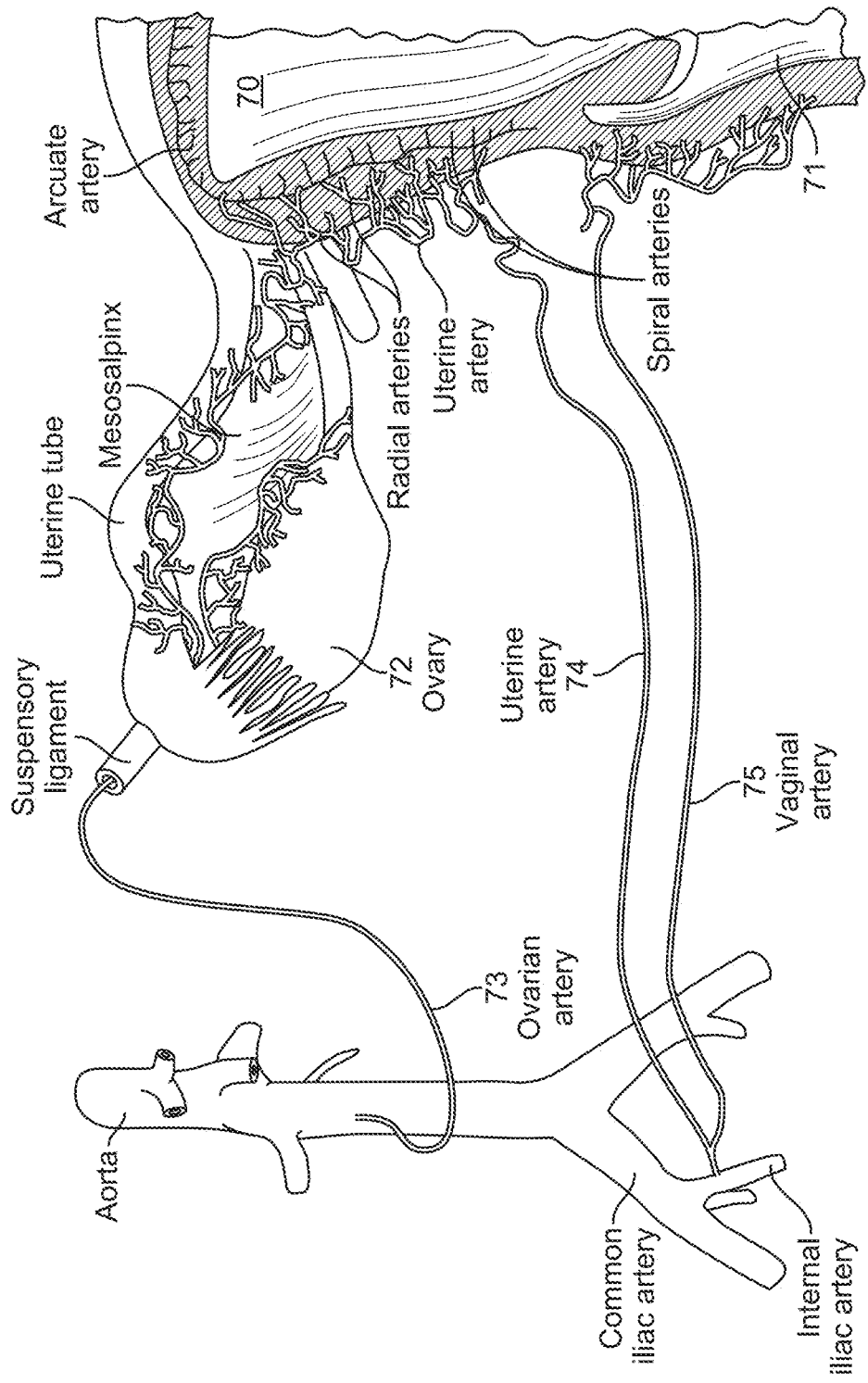
FIG. 9 is an anatomical view illustrating a portion of the uterus, vagina, an ovary and nearby organs and vessels.

FIG. 9 is an anatomical view illustrating a portion of the uterus 70, vagina 71, an ovary 72 and nearby organs and vessels, including an ovarian artery 73, a uterine artery 74 and a vaginal artery 75. Treatment procedures for ovarian, uterine or vaginal neuromodulation in accordance with embodiments of the present technology can include applying a treatment modality at one or more treatment locations proximate a structure having a relatively high concentration of ovarian, uterine, or vaginal sympathetic nerves, respectively. In some embodiments, for example, at least one treatment location can be proximate a portion/branch/ostium of the ovarian artery 73 (or vein) for neuromodulation of an ovarian plexus, a portion/branch/ostium of the uterine artery 74 (or vein) for neuromodulation of a uterine plexus or other uterine nerve, or the vaginal artery 75 (or vein) for neuromodulation of a vaginal plexus or other vaginal nerve and/or another suitable structure in the vicinity of sympathetic nerves innervating the ovaries, uterus and/or vagina.

As provided herein, neuromodulation is likely to be valuable in the treatment of ovarian cancer, uterine cancer, cervical cancer, vaginal cancer, cancer of the vulva and/or cancers associated with other female reproductive organs and tissues (e.g., endometrial cancer). In particular, renal neuromodulation along the ovarian artery 73, the uterine artery 74, the vaginal artery 75 and/or within other vessels associated with the female reproductive organs and tissues is expected to reduce sympathetic drive in these organs, thereby reducing the impact of SNS activation on aspects of cancer progression. As the reduction of afferent neural signals contributes to the systemic reduction of sympathetic tone/drive, neuromodulation of the sympathetic nerves innervating these structures might also be useful in treating cancers found throughout the body. For example, a reduction in central sympathetic drive may reduce the incidence of metastasis and/or improve another measurable physiological parameter associated with the progression of cancer.

Figure 10:
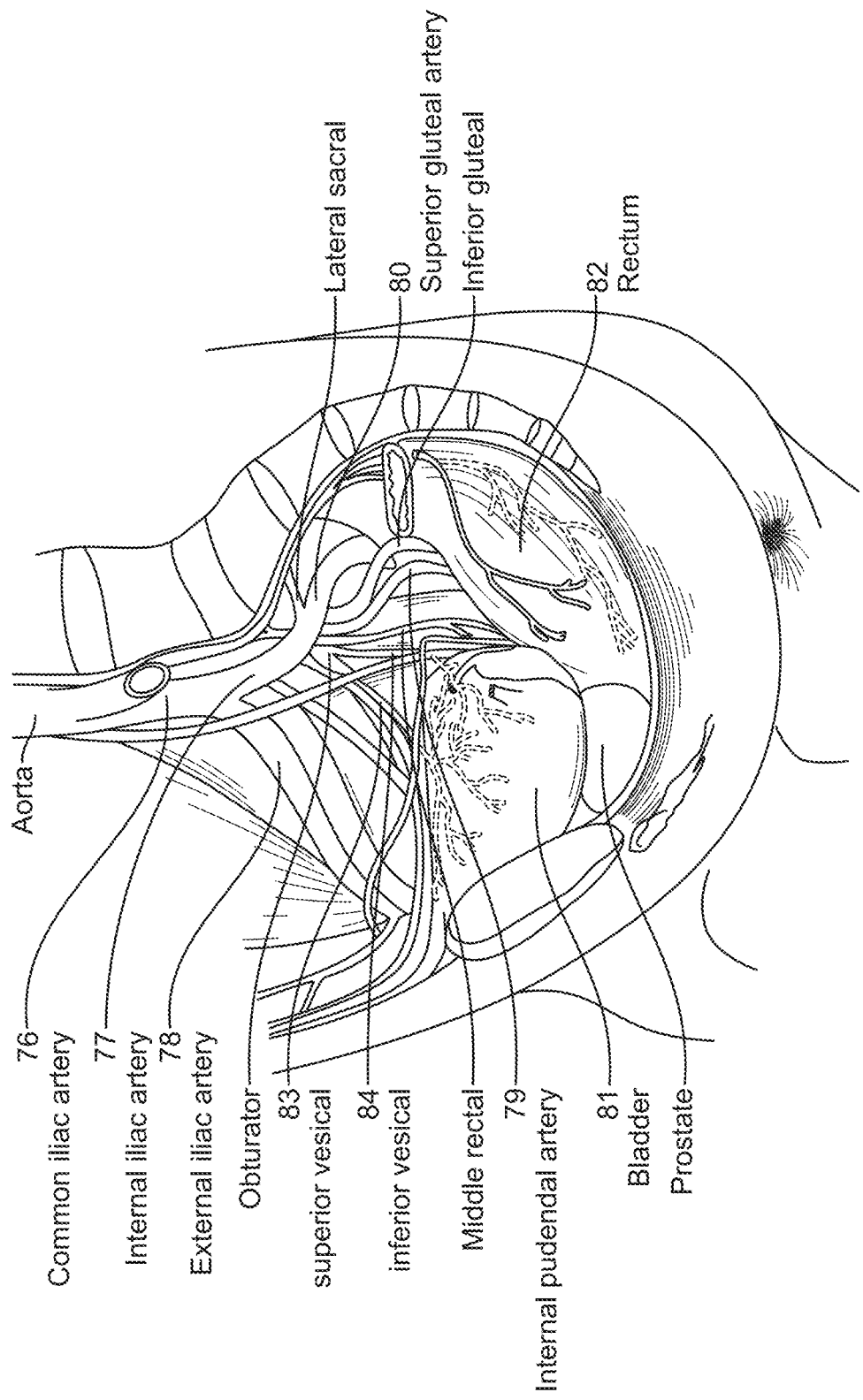
FIG. 10 is a cross-sectional anatomical view illustrating a common iliac artery, an internal iliac artery, an external iliac artery, an internal pudendal artery, a superior gluteal artery and other nearby structures and vessels.

FIG. 10 is a cross-sectional anatomical view illustrating a common iliac artery 76, an internal iliac artery 77, an external iliac artery 78, an internal pudendal artery 79, a superior gluteal artery 80 and other nearby structures and vessels. Treatment procedures for neuromodulation of the female (e.g., vulva, vagina, clitoris) or male (e.g., testes, penis, prostate, etc.; described further below) reproductive organs for the treatment of cancer can include, for example, applying a treatment modality at one or more treatment locations proximate a structure having a relatively high concentration of sympathetic nerves innervating these reproductive or genital structures. In some embodiments, for example, at least one treatment location can be proximate a portion/branch/ostium of the internal iliac artery 77 (or vein) for neuromodulation of a sacral plexus, a portion/branch/ostium of the external iliac artery 78 (or vein) for neuromodulation of a genital branch of a genitofemoral nerve, a portion/branch/ostium of the internal pudendal artery 79 (or vein) for neuromodulation of a pudendal nerve or perineal nerve, a portion/branch/ostium of the superior gluteal artery 80 (or vein) for neuromodulation of a lumbosacral plexus, a portion/branch/ostium of the deep circumflex iliac artery (or vein) which is a branch of the external iliac artery 78 for neuromodulation of a ilioinguinal nerve, and/or another suitable structure in the vicinity of nerves innervating the female (or male) reproductive organs.

Neuromodulation of sympathetic nerve fibers innervating female reproductive viscera, as described above, are expected to be useful to reduce at least one of a primary malignant tumor growth rate, a primary malignant tumor size, and/or a degree of vascularization of a primary malignant tumor associated with these organs and/or reduce a number circulating tumor cells. In other embodiments, reducing sympathetic neural activity in these sympathetic nerves and/or reducing central sympathetic drive may improve an effectiveness of chemotherapy agents on tumor cells in the patient.

2. Sympathetic Nerves of the Male Reproductive System

Referring back to FIG. 10, treatment procedures for neuromodulation of sympathetic nerves innervating the male reproductive organs (e.g., testes, penis, prostate, etc.) for the treatment of cancer are contemplated. In some embodiments, neuromodulation of a sacral plexus, a genital branch of a genitofemoral nerve, a pudendal nerve or perineal nerve, the lumbosacral plexus and/or the ilioinguinal nerve can be achieved via application of a suitable treatment modality, e.g., cryotherapeutic, direct heat, electrode-based, transducer-based, chemical-based, or another suitable treatment modality within a target vessel as described above. In a particular example, the pudendal nerve, which is derived from the sacral plexus, accompanies the internal pudendal vessels (e.g., internal pudendal artery 79) to innervate male genitalia, such as the penis and the scrotum. Additional sympathetic nerves to the male reproductive organs and genitalia descend through the inferior mesenteric plexus and the inferior hypogastric plexus which accompany the branches of the inferior mesenteric artery (not shown) and the internal iliac artery 77, respectively. Additional treatment locations for neuromodulation of sympathetic nerves innervating male reproductive organs are further described below.

Figure 11A:
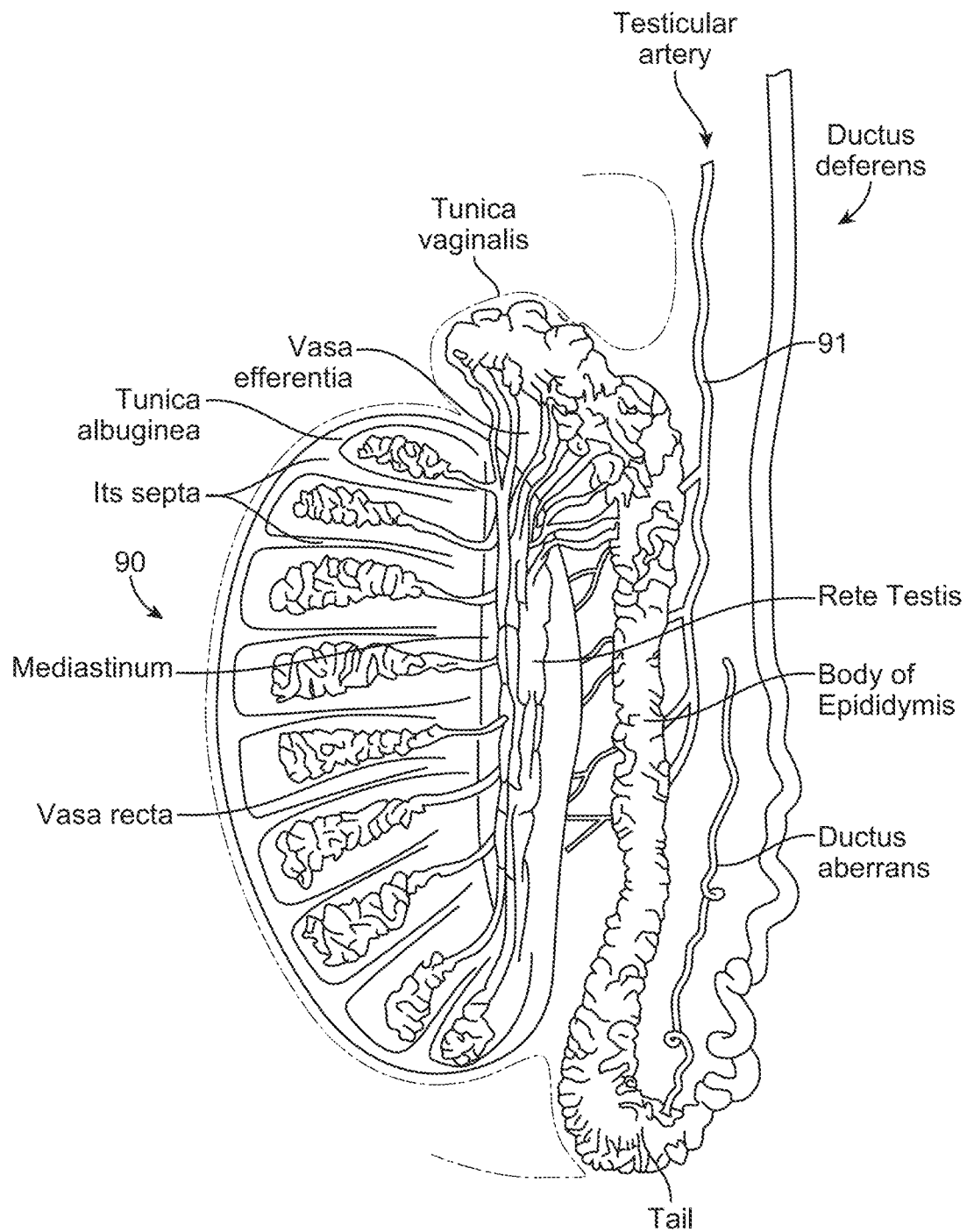
FIG. 11A is anatomical views illustrating the testicular artery and nearby organ structures and vessels.
Figure 11B:
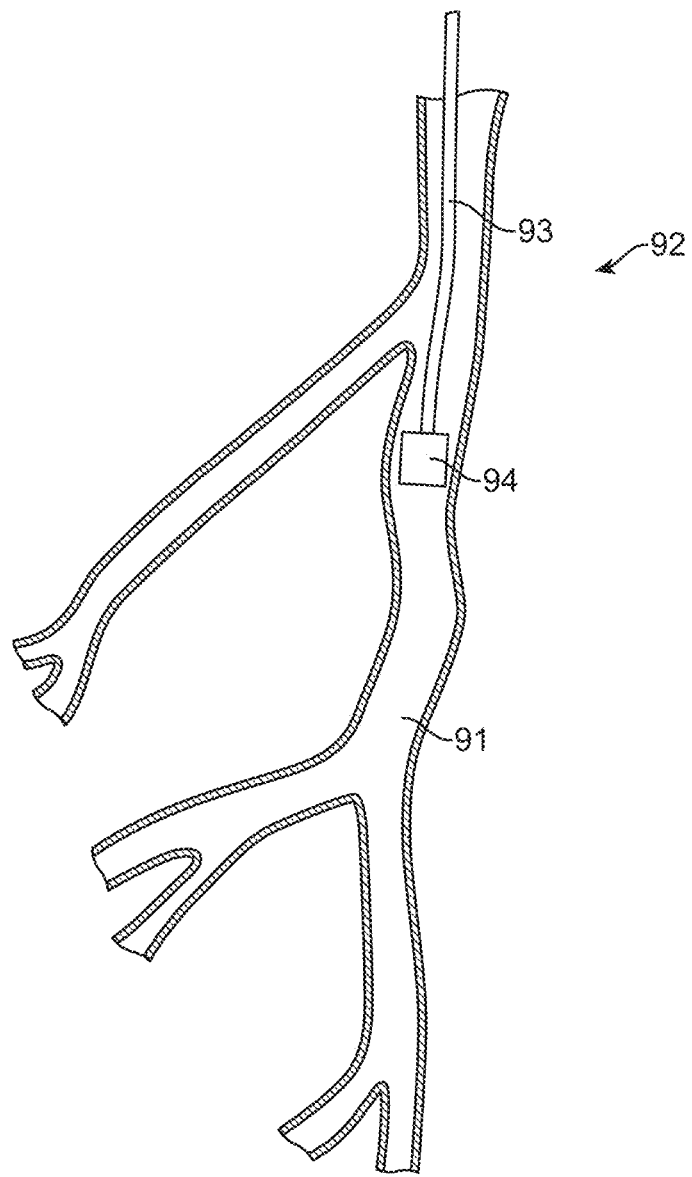
FIG. 11B is a partially cross-sectional view illustrating neuromodulation at a treatment location within the testicular artery in accordance with an embodiment of the present technology.

FIG. 11A is a cross-sectional anatomical view illustrating a testicle 90, a testicular artery 91, and nearby structures and vessels. Treatment procedures for testicular neuromodulation for the treatment of testicular cancer, for example, can include applying a treatment modality at one or more treatment locations proximate a structure having a relatively high concentration of sympathetic nerves innervating the testes. In some embodiments, for example, at least one treatment location can be proximate a portion of the testicular artery 91, a branch of the testicular artery 91, an ostium of the testicular artery 91, an testicular vein, a branch of an testicular vein, an ostium of an testicular vein, and/or another suitable structure in the vicinity of testicular nerves (e.g., nerves originating at the spermatic plexus, the genital branch of the genitofemoral nerve). FIG. 11B, for example, is a cross-sectional view illustrating neuromodulation at a treatment location within the testicular artery 91. As shown in FIG. 11B, a treatment device 92 including a shaft 93 and a therapeutic element 94 can be extended toward the testicular artery 91 to locate the therapeutic element 94 at the treatment location within the testicular artery 91. The therapeutic element 94 can be configured for neuromodulation at the treatment location via a suitable treatment modality, e.g., cryotherapeutic, electrode-based, transducer-based, chemical-based, or another suitable treatment modality.

Figure 12:
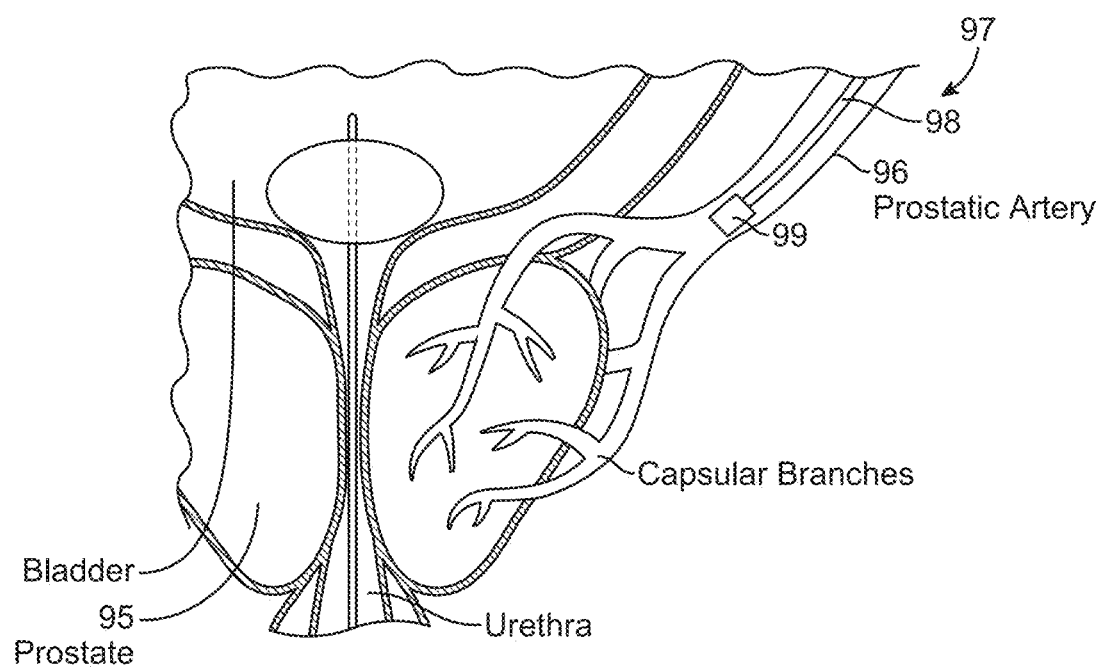
FIG. 12 is a cross-sectional anatomical view showing a prostate, a prostatic artery, and nearby structures and vessels and illustrating neuromodulation at a treatment location within the prostatic artery in accordance with an embodiment of the present technology.

FIG. 12 is a cross-sectional anatomical view illustrating a prostate 95, a prostatic artery 96, and nearby structures (e.g., urinary bladder, urethra) and vessels (e.g., capsular branches). Treatment procedures for prostatic neuromodulation for the treatment of prostate cancer, for example, can include applying a treatment modality at one or more treatment locations proximate a structure having a relatively high concentration of sympathetic nerves innervating the prostate. In some embodiments, neuromodulation of the prostatic plexus which is intimately associated with the prostatic arteries, which is derived from internal iliac artery 77 (FIG. 10), is expected to be useful in the treatment of prostate cancer. FIG. 12 also shows a treatment device 97 including a shaft 98 and a therapeutic element 99 can be positioned within the left or right prostatic artery 96 to locate the therapeutic element 99 at the treatment location. The therapeutic element 99 can be configured for neuromodulation at the treatment location via a suitable treatment modality, e.g., cryotherapeutic, electrode-based, transducer-based, chemical-based, or another suitable treatment modality.

While long-term disruption of the prostatic plexus or other sympathetic nerves (e.g., pudendal nerve) may be desirable for treating certain prostate, testicular and/or penile cancer patients over longer periods of time, short-term modulation of these nerves may also be desirable. For example, some patients may benefit from short-term modulation to address the effects of cancer progression; however, in certain instances, recovery of the function of these nerves may be desirable if side-effects such as erectile dysfunction, loss of sensation and/or incontinence are experienced.

3. Sympathetic Nerves of Non-Reproductive Pelvic Organs

Other embodiments are directed to modulation of sympathetic nerves (e.g., inferior mesenteric plexus, left colic plexus, sigmoid plexus, superior hemorrhoidal plexus, inferior hypogastric plexus, pelvic plexus, middle rectal plexus, etc.) innervating the urinary bladder, descending and/or sigmoid colon and/or rectum. Referring back to FIG. 10, treatment procedures for neuromodulation of sympathetic nerves innervating the urinary bladder 81, the descending and sigmoid colon (not shown), and the rectum 82 for the treatment of cancer in these organ structures are contemplated. In some embodiments, neuromodulation of a vesical plexus, which accompanies the superior vesical artery 83 and inferior vesical artery 84, can be can be used in a treatment of urinary bladder cancer. Other nerve structures (e.g., inferior mesenteric plexus, hypogastric plexus) can also be targeted in the treatment of urinary bladder cancer and accessed via the inferior mesenteric artery (not shown) or the internal iliac artery 77. Additional sympathetic nerves (e.g., left colic plexus, sigmoid plexus, and superior hemorrhoidal plexus) that innervate the lower colon structures (not shown) and rectum 82 can also be targeted. These nerve structures accompany the branches of the inferior mesenteric artery (not shown) and the internal iliac artery 77.

D. Neuromodulation of Target Sympathetic Nerve

Various techniques can be used to partially or completely incapacitate neural pathways, such as those innervating the tissues and organs discussed above. The purposeful application of energy (e.g., electrical energy, thermal energy) to tissue can induce one or more desired thermal heating and/or cooling effects on localized regions along all or a portion of the target vessel and adjacent regions of the SNS nerve targets, which often lay intimately within or adjacent to the adventitia of the target vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site. Suitable energy modalities can include, for example, RF energy (monopolar and/or bipolar), pulsed RF energy, microwave energy, ultrasound energy (e.g., intravascularly delivered ultrasound, extracorporeal ultrasound, high-intensity focused ultrasound (HIFU)), laser, optical energy, magnetic energy, direct heat, radiation (e.g., infrared, visible, gamma), or other suitable energy modalities alone or in combination. Where a system uses a monopolar configuration, a return electrode or ground patch fixed externally on the subject can be used. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies are described in U.S. patent application Ser. No. 13/279,330, filed Oct. 23, 2011, International Patent Application No. PCT/US2015/021835, filed Mar. 20, 2015, and U.S. Provisional Patent Application No. 61/932,213, filed Jan. 27, 2014. Additional thermal devices are described in U.S. patent application Ser. No. 13/279,205, filed Oct. 21, 2011. All of the foregoing patent references are incorporated herein by reference in their entireties.

By way of theory, targeting both general afferent and efferent sympathetic nerves (e.g., via a catheter-based approach, extracorporeal ultrasound) may cause beneficial effects extending well beyond affecting cancer progression in or near the target tissues and/or organs, such as reducing the number of viable circulating tumor cells and/or reducing a risk of forming a metastatic tumor at a secondary site via the circulating tumor cells. As discussed herein, a correlation between stress-induced sympathetic activation on cancer progression and metastasis has been established. There is now also evidence that sympathetic activation results in adverse consequences on cell proliferation, tumor growth rate, angiogenesis, timing and frequency of metastasis, as well as effectiveness of chemotherapy drugs on the primary malignant tumor. Additionally, chronic stress causes hyperactivity (e.g., overactivity) of the sympathetic nervous system throughout the body. When experiencing stress, including chronic stress, hormonal and neural information (e.g., sensory afferent input) is received by the CNS, which in turn further elevates sympathetic tone via efferent signaling throughout the body. Some aspects of methods of treating patients having cancer using sympathetic neuromodulation are at least in part derived from the recognition described herein that the kidneys may contribute to elevated central sympathetic drive.

Several aspects of the current technology are configured to reduce sympathetic nerve activity within or near tissues and/or organs comprising a primary malignant tumor. Beneficial effects of reducing targeted sympathetic neural activity can include reducing localized release of norepinephrine. Several properties of the target tissue vasculature may inform the design of treatment devices and associated methods for achieving target sympathetic neuromodulation, for example, via intravascular access, and impose specific design requirements for such devices. Specific design requirements may include percutaneously accessing the vasculature (e.g., pulmonary artery/vein, internal thoracic artery, celiac artery, superior mesenteric artery, hepatic artery splenic artery, gastric artery, inferior mesenteric artery, pancreatic artery, ovarian artery, internal iliac artery and branches thereof, uterine artery, testicular artery, external iliac artery and branches thereof, internal pudendal vessels, hypogastric artery and branches thereof, and superior vesical artery among others), facilitating stable contact between the energy delivery elements of such devices and a luminal surface or wall of the vasculature, and/or effectively modulating the target sympathetic nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation might be useful in treating multiple cancers wherein progression and/or metastasis is associated with systemic sympathetic hyperactivity. For example, as previously discussed, a reduction in central sympathetic drive may reduce a likelihood of metastasis among other physiological parameters associated with a primary malignant tumor.

Accordingly, renal neuromodulation is expected to be useful in treating cancer. The beneficial effect of renal neuromodulation with respect to cancer is expected to apply regardless of the baseline renal sympathetic neural activity or the baseline level of norepinephrine in plasma (e.g., whole body norepinephrine spillover). For example, renal neuromodulation in accordance with embodiments of the present technology can improve one or more measurable physiological parameters corresponding to the progression of cancer in the patient when baseline renal sympathetic neural activity is normal, below normal, or above normal (e.g., hyperactive or overactive). Likewise, renal neuromodulation in accordance with additional embodiments of the present technology can improve one or more measurable physiological parameters corresponding to the progression of cancer in the patient when baseline central sympathetic drive, baseline norepinephrine spillover in plasma, and/or whole body norepinephrine spillover is normal, below normal, or above normal (e.g., hyperactive or overactive).

As described above with respect to the design of treatment devices and associated methods for target sympathetic neuromodulation, several properties of the renal vasculature may inform the design of treatment devices and associated methods for achieving renal neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

III. Methods for Treatment of Cancer

Disclosed herein are several embodiments of methods directed to treatment of cancer and other conditions associated with an increased risk of developing cancer (e.g., pre-disposition to developing cancer, pre-cancerous lesions, etc.) using catheter-based neuromodulation. The methods disclosed herein are expected to represent various advantages over a number of conventional approaches and adjuvant therapies for reducing the effects of the SNS, and in particular overactivity or hyperactivity of the SNS, on the progression of cancer. For example, the present methods allow for the potential targeting of elevated sympathetic drive, which may be a key mediator of multiple physiological pathways promoting progression of the disease (e.g., abnormal cell proliferation, increased growth rate of tumors, ECM remodeling, angiogenesis, tumor-protective inflammatory responses, promotion of epithelial-to-mesenchymal transition (EMT), and other aspects related to cell invasiveness and metastasis (e.g., via lymphatic or hematogenous spread of tumor cells)). Accordingly, the methods disclosed herein are expected provide therapeutically beneficial improvement in one or more measurable physiological parameters corresponding to the progression of cancer in the patient, as well as provide for localized treatment and limited duration treatment regimens (e.g., one-time treatment).

In certain embodiments, the methods provided herein comprise performing targeted sympathetic neuromodulation, thereby decreasing target sympathetic nerve activity in tissues proximate to or organs comprising a primary malignant tumor for the purposes of being able to provide one or more of a reduction in tumor growth rate of the primary malignant tumor in the patient, a decrease in a frequency of metastasis of the primary malignant tumor, at least partial inhibition of vascularization of the primary malignant tumor, a decrease in a number of metastatic tumors derived from the primary malignant tumor in the patient, and an increase effectiveness of a chemotherapy agent on cancer cells derived from the primary malignant tumor. For example, targeted neuromodulation is expected to reduce a level of localized sympathetic activity, and concomitant release of norepinephrine, in the tissues and/or organs comprising the primary cancer. Reduction of regional or localized norepinephrine levels is expected to reduce adrenergic signaling activation within and near the tumor stroma.

Targeted sympathetic neuromodulation may be repeated one or more times at various intervals until a desired sympathetic nerve activity level or another therapeutic benchmark is reached. In one embodiment, for example, a decrease in regional or local sympathetic nerve activity may be observed via a marker of sympathetic nerve activity in cancer patients, such as decreased levels of plasma norepinephrine (noradrenaline) or decreased levels of localized norepinephrine assessed by tissue biopsy. Other measures or markers of sympathetic nerve activity can include muscle sympathetic nerve activity (MSNA), norepinephrine spillover, and/or heart rate variability. In another embodiment, other measurable physiological parameters or markers, such as a reduction in a growth rate of the primary malignant tumor, a reduction or percent shrinkage of the primary malignant tumor, a reduction in blood flow to the tumor stroma and/or maintenance or reduction in the formation of new blood vessels in the tumor stroma, a reduction in cytokine levels in the patient, a reduction in pain level perceived by the cancer patient, improved blood pressure control, improved blood glucose regulation, etc., can be used to assess efficacy of the neuromodulation treatment for cancer patients.

In certain embodiments of the methods provided herein, targeted sympathetic neuromodulation is expected to result in a change in sympathetic nerve activity over a specific timeframe. For example, in certain instances of these embodiments, sympathetic nerve activity levels are decreased over an extended timeframe, e.g., within 1 month, 2 months, 3 months, 6 months, 9 months or 12 months post-neuromodulation. In further embodiments, sympathetic nerve activity levels may remain at decreased levels over extended timeframes such as greater than 3 months, greater than 6 months, greater than 12 months or greater than 24 months post-neuromodulation.

In several embodiments, the methods disclosed herein may comprise an additional step of measuring sympathetic nerve activity levels, and in certain instances of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity levels may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In one embodiment, measured norepinephrine content (e.g., assessed via tissue and/or tumor biopsy, assessed in real-time via intravascular blood collection techniques, etc.) can be reduced (e.g., at least about 5%, 10%, 20% or by at least 40%) in the patient within about three months after at least partially inhibiting sympathetic neural activity in nerves proximate a target vessel and innervating an organ or tissue comprising the tumor.

In one embodiment, targeted sympathetic neuromodulation may be performed on a patient diagnosed with cancer to reduce one or more measurable physiological parameters corresponding to progression of the cancer. In some embodiments, for example, targeted sympathetic neuromodulation may prevent, maintain, or reduce a tumor growth rate of the primary malignant tumor. A reduction in the growth rate of the tumor can be, for example, at least about 5%, 10%, 25%, 50% or a greater amount as determined by qualitative or quantitative analysis (e.g., ultrasound, magnetic resonance imaging (MM), positron emission tomography (PET) scan, X-Ray, etc.) before and after (e.g., 1, 3, 6, or 12 months after) a targeted sympathetic neuromodulation procedure. In other embodiments, targeted sympathetic neuromodulation may prevent expansion of, maintain, or reduce a primary malignant tumor size in a patient. A reduction in tumor size can be, for example, at least about 5%, 10%, or a greater amount as determined by qualitative or quantitative analysis (e.g., ultrasound, MRI, PET scan, X-Ray, etc.) before and after (e.g., 1, 3, 6, or 12 months after) a targeted sympathetic neuromodulation procedure.

In addition to or instead of affecting the growth rate or size of a primary malignant tumor in a patient, targeted sympathetic neuromodulation may efficaciously treat other measurable physiological parameter(s) or sequela(e) corresponding to the progression of cancer in the patient. For example, in some embodiments, targeted sympathetic neuromodulation may decrease a frequency of metastasis of the primary malignant tumor and/or decrease a number of metastatic tumors derived from the primary malignant tumor in the patient. In a particular example, targeted sympathetic neuromodulation may reduce a number of circulating cancer cells via lymphatic or hematological systems in the patient. In one embodiment, evaluation of parameters associated with metastasis of the primary tumor may be based on comparisons to a baseline value derived from a standard or accepted epidemiological value established for patients having the same cancer form, stage and/or other medical factors. In particular embodiments, patients may be evaluated on metastasis-related parameters within about 6 months, a year, 2 years, up to 5 years, or a longer period following targeted sympathetic neuromodulation.

In yet other embodiments, targeted sympathetic neuromodulation may at least partially inhibit vascularization of the primary malignant tumor. In particular examples, a reduction in local sympathetic neural activity may prevent, maintain, or reduce formation of blood vessels and/or blood flow within or near the tumor. A reduction in blood flow perfusion of tumors can be, for example, at least about 5%, 10%, 25%, 50% or a greater amount as determined by qualitative or quantitative analysis (e.g., PET, direct contrast-enhanced MM, perfusion computed tomography, etc.) before and after (e.g., 1, 3, 6, or 12 months after) a targeted sympathetic neuromodulation procedure.

In some embodiments, targeted sympathetic neuromodulation may prevent an increase in, maintain, or reduce a level of tumor-associated inflammation in the patient. Targeted sympathetic neuromodulation may improve (e.g., reduce a level of) markers of inflammation (e.g., IL-6, IL-8) or may improve (e.g., prevent an increase in, maintain, or reduce) a number or density of TAMs within or proximal to the tumor in a patient. These and other results may occur at various times, e.g., directly following neuromodulation or within about 1 month, 3 months, 6 months, a year, or a longer period following neuromodulation. In further embodiments, targeted sympathetic neuromodulation can increase an effectiveness of one or more chemotherapy agents on cancer cells derived from the primary malignant tumor. Evaluation of effectiveness of chemotherapy agents post-neuromodulation may be assessed by comparison to a baseline value derived from a standard or accepted epidemiological value established for patients having the same cancer form, stage and/or other medical factors, or in other embodiments by assessing other markers of chemotherapy efficacy, such as, tumor shrinkage and biomarkers of increased cell death such as cellular proteases in plasma (Wiita, A. P., et al., *PNAS,* 2014, 111: 7594-7599). These and other results can occur at various times, e.g., directly following targeted sympathetic neuromodulation or within about 1 month, 3 months, 6 months, a year, or a longer period following targeted sympathetic neuromodulation.

In still further embodiments, targeted sympathetic neuromodulation may reduce the severity and/or frequency of pain associated with the cancer in the patient. Such pain reduction can be evaluated by assessing a pain level and/or level of function in the patient following the neuromodulation treatment procedure. For example, a patient can be assessed for pain level, quality, and/or level of function using one or more pain measurement scales, such as a standardized Visual Analog Scale (VAS), before and post-neuromodulation treatment. In a specific embodiment, a reported level of pain (e.g., as assessed on one or more pain measurement scales known in the art), can be decreased by about 5%, about 10%, about 15%, about 20%, about 30%, about 40%, about 50%, about 75%, or about 90%. In other embodiments, patients may report that no measurable pain is experienced following a neuromodulation procedure.

As discussed previously, the progression of cancer may be related to sympathetic overactivity and, correspondingly, the degree of sympathoexcitation in a patient may be related to the severity of the clinical presentation of the cancer, or in other embodiments, a level of psychological stress, social isolation, a duration of chronic stress, and other factors. The targeted tissues and organs comprising the malignant tumor may be positioned to be both a cause (via afferent nerve fibers) and a target (via efferent sympathetic nerves) of elevated central sympathetic drive. In some embodiments, targeted sympathetic neuromodulation can be used to reduce central sympathetic drive in a patient diagnosed with cancer in a manner that treats the patient for the cancer and/or improves one or more measurable physiological parameters associated with the progress of cancer in the patient.

In certain embodiments, renal neuromodulation is used to reduce central sympathetic drive in a patient diagnosed with cancer in a manner that treats the patient for the cancer and/or improves one or more measurable physiological parameters associated with the progress of cancer in the patient. In some embodiments, for example, MSNA can be reduced by at least about 10% in the patient within about three months after at least partially inhibiting sympathetic neural activity in nerves proximate a renal artery of the kidney. Similarly, in some instances whole body norepinephrine spillover can be reduced at least about 20%, about 30%, about 40%, about 45%, about 50% or a greater amount in the patient within about three months to about 12 months after at least partially inhibiting sympathetic neural activity in nerves proximate a renal artery of the kidney. Additionally, measured norepinephrine content (e.g., assessed via renal biopsy, assessed in real-time via intravascular blood collection techniques, etc.) can be reduced (e.g., at least about 5%, 10%, or by at least 20%) in the patient within about three months after at least partially inhibiting sympathetic neural activity in nerves proximate a renal artery innervating the kidney.

In one prophetic example, a patient diagnosed with cancer can be subjected to a baseline assessment indicating a first set of measurable parameters corresponding to characteristics of a primary malignant tumor and the tumor stroma (e.g., microenvironment). Such parameters can include, for example, levels of central sympathetic drive (e.g., MSNA, whole body norepinephrine spillover), measured norepinephrine content (e.g., assessed via tissue and/or tumor biopsy), tumor size, tumor growth rate, markers of angiogenesis (e.g., blood vessel formation, blood flow perfusion within tumor, levels of angiogenic biomarkers (VEGF, bFGF, secretoneurin, substance P, neuropeptide Y, etc.) in plasma or tissue biopsy), markers of tumor-associated inflammation (e.g., levels of IL-6 and/or IL-8, density of TAMs in tumor/tumor stroma), blood pressure and heart rate. Following baseline assessment, the patient can be subjected to a renal neuromodulation procedure and/or a targeted sympathetic neuromodulation procedure (e.g., targeting SNS nerves innervating tissue proximal tumor). Such procedures can, for example, include any of the treatment modalities described herein or another treatment modality in accordance with the present technology. For renal neuromodulation, the treatment can be performed on nerves proximate one or both kidneys of the patient. For targeted sympathetic neuromodulation, treatment can be performed on nerves proximate multiple organs, contralateral organ structures (e.g., lung, breast, testes, ovaries, etc.) or on multiple nerves innervating the same organ. Following the treatment (e.g., 1, 3, 6, or 12 months following the treatment), the patient can be subjected to a follow-up assessment. The follow-up assessment can indicate a measurable improvement in one or more physiological parameters corresponding to the progression of cancer.

The methods described herein address the sympathetic excess that is thought to be an underlying factor in cancer progression in patients. Currently, there are no therapies prescribed to address the effects of sympathetic excess on tumor progression and metastasis. Certain proposed therapies, such as administration of β-blockers, have significant limitations including limited efficacy, undesirable side effects and may be subject to adverse or undesirable drug interactions when used in combination. Moreover, use of β-adrenergic antagonists may require the patient to remain compliant with the treatment regimen over time. In contrast, neuromodulation can be a one-time or otherwise limited treatment that would be expected to have durable benefits to inhibit the long-term cancer progression and thereby achieve a favorable patient outcome.

In some embodiments, patients diagnosed with cancer can be treated with one or more conventional therapies (e.g., surgery, chemotherapy and/or radiation) and treated with one or more neuromodulation treatments. In some instances, patients may be treated with neuromodulation alone. However, in further embodiments, patients diagnosed with cancer can be treated with other combinations of adjuvant therapies for addressing the sympathetic excess that is thought to be an underlying factor in cancer progression in patients. For example, combinations of therapies can be tailored based on specific manifestations of the cancer in a particular patient. In a specific example, patients having cancer can be treated with both adrenergic antagonist drugs, such as β-blockers (e.g., Propranolol, Carvedilol, Labetalol, Nadolol, Timolol among others) and renal neuromodulation and/or targeted sympathetic neuromodulation (e.g., in a tissue region associated with primary malignant tumor).

Treatment of cancer or related conditions may refer to preventing the disease, slowing the onset or rate of development of the disease (e.g., primary malignant tumor), reducing the risk of developing cancer, preventing or delaying metastasis of the primary cancer, reducing or ending symptoms (e.g., pain) associated with the cancer, generating a complete or partial regression of the tumor(s), or some combination thereof.

IV. Selected Examples of Neuromodulation Modalities

As noted previously, complete or partial neuromodulation of a target sympathetic nerve in accordance with embodiments of the present technology can be electrically-induced, thermally-induced, chemically-induced, or induced in another suitable manner or combination of manners at one or more suitable locations during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, HIFU), direct heat energy, or cryotherapeutic energy, chemicals (e.g., drugs or other agents), or combinations thereof. In certain embodiments, neuromodulation may utilize one or more devices including, for example, catheter devices such as the Symplicity™ catheter (Medtronic, Inc.). Other suitable thermal devices are described in U.S. Pat. Nos. 7,653,438, 8,347,891, and U.S. patent application Ser. No. 13/279,205, filed Oct. 21, 2011, and examples of suitable multi-electrode devices are described in U.S. patent application Ser. No. 13/281,360, filed Oct. 25, 2011, and U.S. Pat. No. 8,888,773. Other examples of suitable direct heat devices are described in U.S. Provisional Patent Application No. 61/789,113 filed Mar. 15, 2013, and U.S. patent application Ser. No. 14/203,933, filed Mar. 11, 2014. The disclosures of these applications are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities.

In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a target sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion. Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys or other organs to pulse. Cryogenic adhesion also can facilitate intravascular or intraluminal positioning, particularly in relatively-small structures (e.g., relatively-short arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery. In examples where cancer cells reside in other organs or tissues, neuromodulation of target sympathetic nerves innervating those tissues may likewise be carried out at a location proximate (e.g., at or near) a vessel wall, wherein the target sympathetic nerves lay within or adjacent to the adventitia of the selected vessel.

In certain embodiments, monitoring, assessing and/or determining neuromodulation efficacy can be accomplished by detecting changes in the level of one or more surrogate biomarkers (e.g., a biomarker that directly or indirectly correlates with sympathetic nervous activity in the patient, a biomarker that directly or indirectly correlates with cancer progression, metastasis and/or a tumor-associated inflammatory response in the patient) in plasma or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

V. Selected Embodiments of Neuromodulation Systems and Devices

Figure 13:
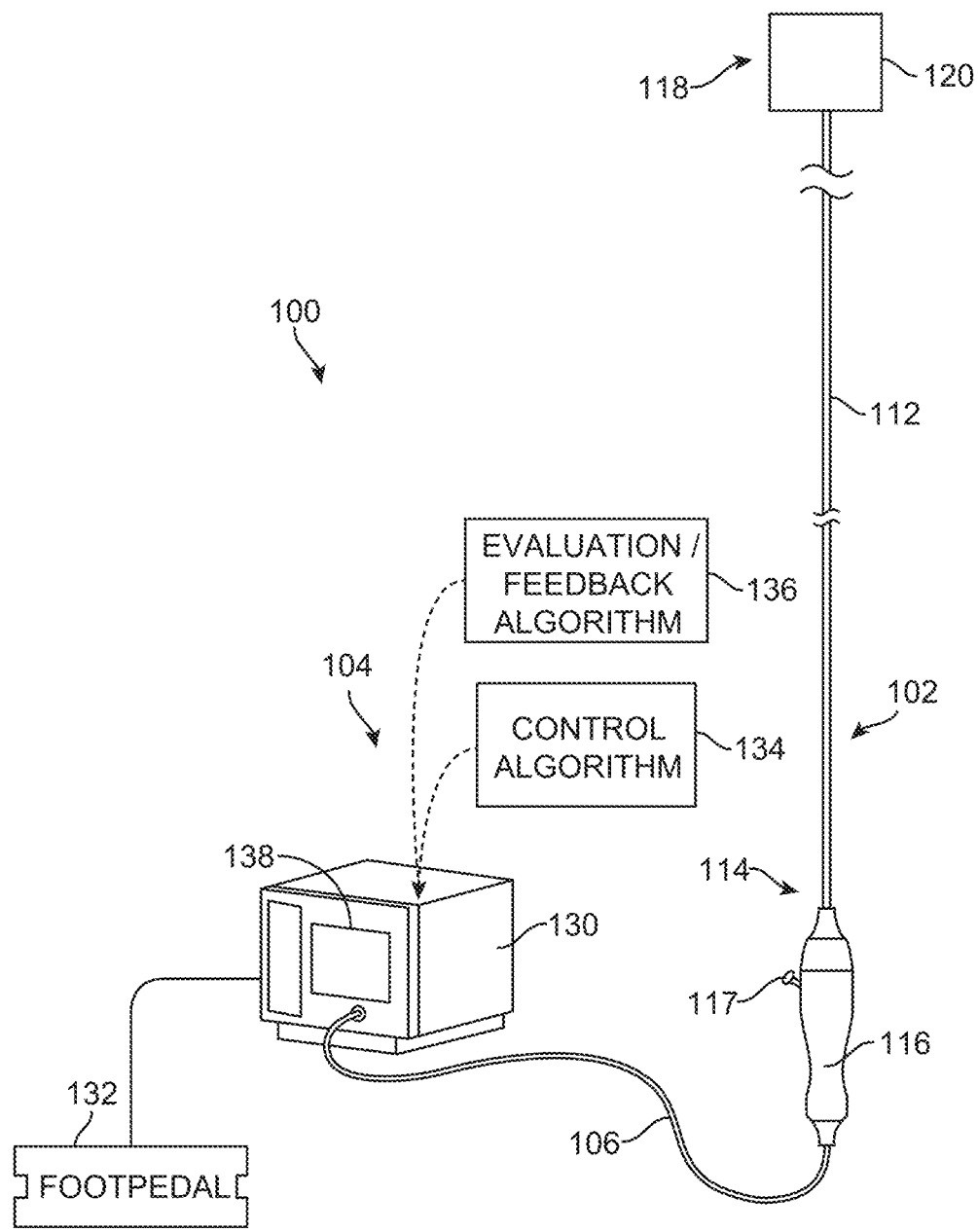
FIG. 13 illustrates an intravascular neuromodulation system configured in accordance with an embodiment of the present technology.

FIG. 13 illustrates a neuromodulation system 100 configured in accordance with an embodiment of the present technology. The system 100, for example, may be used to perform therapeutically-effective neuromodulation of one or more target sympathetic nerves of a patient diagnosed with cancer. The system 100 includes an intravascular treatment device 102 operably coupled to an energy source 104 and/or console 130 (e.g., RF energy generator, a cryotherapy console). In the embodiment shown in FIG. 13, the treatment device 102 (e.g., a catheter) includes an elongated shaft 112 having a proximal portion 114, a handle 116 at a proximal region of the proximal portion 114, and a distal portion 118 extending distally relative to the proximal portion 114. The treatment device 102 further includes a neuromodulation assembly or treatment section 120 at the distal portion 118 of the shaft 112. The neuromodulation assembly 120 can include one or more electrodes or energy-delivery elements, a cryotherapeutic cooling assembly and/or a nerve monitoring device configured to be delivered to a target blood vessel (e.g., a target artery) in a low-profile configuration.

In one embodiment, for example, the neuromodulation assembly 120 can include a single electrode. In other embodiments, the neuromodulation assembly 120 may comprise a basket and a plurality of electrodes carried by the basket. The electrodes on the basket may be spaced apart from each other such that each electrode is approximately 90° apart from a neighboring electrode. In yet another embodiment, the neuromodulation assembly 120 can include a balloon and a plurality of bipolar electrodes carried by the balloon. In still another embodiment, the neuromodulation assembly 120 has a plurality of electrodes arranged along an elongated member transformable between a low-profile, delivery configuration (e.g., contained in a delivery catheter) and an expanded, deployed configuration in which the elongated member has a helical/spiral shape. In any of the foregoing embodiments, the neuromodulation assembly 120 may comprise one or more irrigated electrodes.

Upon delivery to a target treatment site within a blood vessel, the neuromodulation assembly 120 can be further configured to be deployed into a treatment state or arrangement for delivering energy at the treatment site and providing therapeutically-effective electrically-induced and/or thermally-induced neuromodulation of target neural fibers. In some embodiments, the neuromodulation assembly 120 may be placed or transformed into the deployed state or arrangement via remote actuation, e.g., via an actuator 117, such as a knob, pin, or lever carried by the handle 116. In other embodiments, however, the neuromodulation assembly 120 may be transformed between the delivery and deployed states using other suitable mechanisms or techniques.

The proximal end of the neuromodulation assembly 120 can be carried by or affixed to the distal portion 118 of the elongated shaft 112. A distal end of the neuromodulation assembly 120 may terminate with, for example, an atraumatic rounded tip or cap. Alternatively, the distal end of the neuromodulation assembly 120 may be configured to engage another element of the system 100 or treatment device 102. For example, the distal end of the neuromodulation assembly 120 may define a passageway for engaging a guide wire (not shown) for delivery of the treatment device using over-the-wire ("OTW") or rapid exchange ("RX") techniques. The treatment device 120 can also be a steerable or non-steerable catheter device (e.g., a guide catheter) configured for use without a guide wire. Body lumens (e.g., ducts or internal chambers) can be treated, for example, by non-percutaneously passing the shaft 112 and neuromodulation assembly 120 through externally accessible passages of the body or other suitable methods.

The console 130 can be configured to generate a selected form and magnitude of energy for delivery to the target treatment site via the neuromodulation assembly 120. A control mechanism, such as a foot pedal 132, may be connected (e.g., pneumatically connected or electrically connected) to the console 130 to allow an operator to initiate, terminate and, optionally, adjust various operational characteristics of the console 130, including, but not limited to, power delivery. The system 100 may also include a remote control device (not shown) that can be positioned in a sterile field and operably coupled to the neuromodulation assembly 120. The remote control device can be configured to allow for selective activation of the neuromodulation assembly 120. In other embodiments, the remote control device may be built into the handle assembly 116. The energy source 104 can be configured to deliver the treatment energy via an automated control algorithm 134 and/or under the control of the clinician. In addition, the energy source 104 may include one or more evaluation or feedback algorithms 136 to provide feedback to the clinician before, during, and/or after therapy.

The energy source 104 can further include a device or monitor that may include processing circuitry, such as a microprocessor, and a display 138. The processing circuitry may be configured to execute stored instructions relating to the control algorithm 134. The energy source 104 may be configured to communicate with the treatment device 102 (e.g., via a cable 106) to control the neuromodulation assembly and/or to send signals to or receive signals from the nerve monitoring device. The display 138 may be configured to provide indications of power levels or sensor data, such as audio, visual or other indications, or may be configured to communicate information to another device. For example, the console 130 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VI. Selected Examples of Treatment Procedures for Neuromodulation

A. Achieving Intravascular Access to the Target Vessels

Figure 14A:
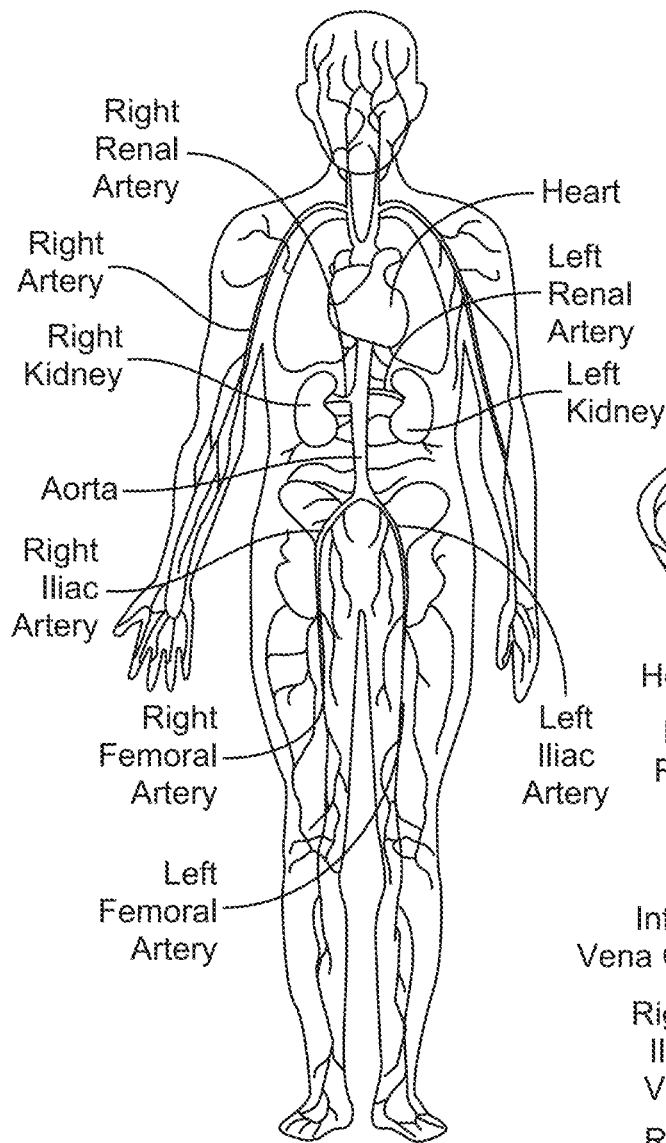
FIGS. 14A and 14B are anatomic views of the arterial vasculature and venous vasculature, respectively, of a human.

In accordance with the present technology, neuromodulation of a target sympathetic nerve, which is intimately associated with a target blood vessel (e.g., target artery), may be achieved through intravascular access. As FIG. 14A shows, blood moved by contractions of the heart is conveyed from the left ventricle of the heart by the aorta. The aorta descends through the thorax and bifurcates at the left and right iliac arteries. The left and right iliac arteries descend, respectively, through the left and right legs and join the left and right femoral arteries.

Figure 14B:
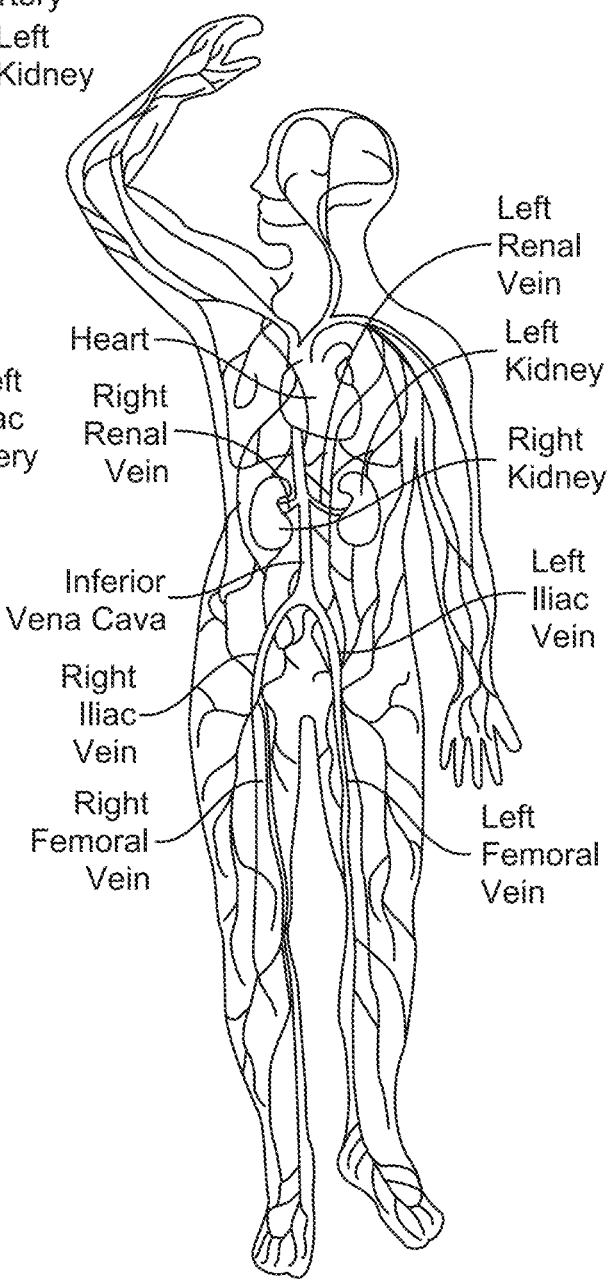

As FIG. 14B shows, the blood collects in veins and returns to the heart, through the femoral veins into the iliac veins and into the inferior vena cava. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, where the catheter may be placed into a target vessel (e.g., celiac artery 42, superior mesenteric artery 44, renal artery 54) for the management and/or treatment of cancer associated with the abdominal viscera 40 (FIGS. 6A-6B) and kidneys 50 (FIG. 7). This route comprises an intravascular path that offers minimally invasive access to a respective celiac artery, superior mesenteric artery, renal artery and/or other blood vessels (e.g., superior mesenteric vein, not shown) associated with the abdominal cavity and an intravascular pathway to some vessel targets associated with the pelvic cavity (e.g., inferior mesenteric artery) and the thoracic cavity (e.g., internal thoracic artery). Alternatively, the wrist, upper arm, and shoulder region provide other locations for introduction of catheters into the arterial system. For example, catheterization of either the radial, brachial, or axillary artery or vein may be utilized to provide an intravascular path to thoracic vessel targets (e.g., pulmonary artery, internal thoracic artery) as well as to the abdominal vessel targets. Catheters introduced via these access points may be passed through the subclavian artery on the left side (or via the subclavian and brachiocephalic arteries on the right side), through the aortic arch, down the descending aorta and into the celiac and/or superior mesenteric arteries using standard angiographic technique.

Catheters introduced via the femoral artery route can also access the arterial vasculature associated with the pelvic cavity (see, e.g., TABLE 3, treatment locations). Referring back to FIGS. 14A and 14B, a catheter may be inserted percutaneously into the femoral artery through this access site, passed through the iliac artery and aorta, and placed into either the left or right testicular artery 91 (FIG. 11A) for neuromodulation of the spermatic plexus such as for the management and/or treatment of cancer associated with the testes 90 (FIGS. 11A and 11B). For the management and/or treatment of cancer associated with the reproductive organs in males (e.g., testes, scrotum and penis) or in females (e.g., cervix, vagina and vulva), neuromodulation of a genital branch of genitofemoral nerve, which is intimately associated with an external iliac artery 78 (FIG. 10), may also be achieved through intravascular access by percutaneously inserting a catheter into either the left or right femoral artery (FIG. 14A), into the respective left or right common iliac artery 76 (FIGS. 10 and 14A) and down into the external iliac artery 78 (FIG. 10). Further, neuromodulation of the ilioinguinal nerve may also be achieved by accessing the deep circumflex iliac artery off of the external iliac artery 78 (FIG. 10). Additional targets for the management/treatment of cancer associated with male and female genitalia/reproductive organs include the sacral plexus and hypogastric plexus, which are intimately associated with a left and/or right internal iliac artery 77 (FIG. 10) or vein, and the pudendal and perineal nerves, both of which are intimately associated with left and/or right internal pudendal arteries 79 (FIG. 10) and veins. Percutaneous intravascular access to these nerve structures can include passing a catheter through the left or right femoral artery (FIG. 14A), into the respective left or right common iliac artery 76 (FIGS. 10 and 14A) and down into the internal iliac artery 77 (FIG. 10) and into the internal pudendal artery 79 (FIG. 10), if desired. Additional targets for the management/treatment of urinary bladder cancer include the vesical plexus, which is intimately associated with the superior vesical artery 83 and inferior vesical artery 84 (FIG. 10). Percutaneous intravascular access to the vesical plexus can include passing a catheter through the left or right femoral artery (FIG. 14A), into the respective left or right common iliac artery 76 (FIGS. 10 and 14A), down into the internal iliac artery 77 (FIG. 10) and into the superior vesical and inferior vesical arteries 83, 84 (FIG. 10).

In accordance with a further embodiment of the present technology, neuromodulation of a left or right vaginal plexus, which is intimately associated with a left or right vaginal artery 75 (FIG. 9), and neuromodulation of a left or right uterine plexus, which is intimately associated with a left or right uterine artery 74 (FIG. 9) may be achieved through intravascular access. Referring to FIGS. 9, 14A, and 14B together, a catheter (not shown) may be inserted percutaneously into the left or right femoral artery through this access site, passed through the left or right iliac artery and the internal iliac artery, respectively, and placed into either the left or right vaginal artery 75 or uterine artery 74 (FIG. 9) for the management and/or treatment of cancer associated with the vagina 71 or uterus 70, respectively (FIG. 9).

In accordance with yet a further embodiment of the present technology, neuromodulation of a left or right ovarian plexus or nerve, which is intimately associated with a left or right ovarian artery 73 (FIG. 9) may be achieved through intravascular access. Referring to FIGS. 9, 14A and 14B together, a catheter (not shown) may be inserted in the left or right femoral artery through this access site, passed through the left or right iliac artery and aorta, and placed into either the left or right ovarian artery 73 (FIG. 9). This route comprises an intravascular path that offers minimally invasive access to a respective ovarian artery 73 and/or other ovarian blood vessels. Another location for introduction of a catheter in the arterial system is through the femoral artery (as described above), passed through to the internal iliac artery, through the uterine artery 74, to the ovarian artery 73. Alternatively, the wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the ovarian arteries 73 using standard angiographic technique.

In another embodiment, neuromodulation of the prostatic plexus, which is intimately associated with prostatic arteries 96 (FIG. 12), may be achieved through intravascular access. Referring to FIGS. 12, 14A and 14B together, a treatment device 97 may be inserted in the left or right femoral artery through this access site, passed through the left or right iliac artery and the internal iliac artery, respectively, and placed into either the left or right prostatic artery 96 (FIG. 12) for the management and/or treatment of cancer associated with the prostate 95 (FIG. 12).

Additional targets for the management/treatment of cancer associated with pelvic organs (e.g., urinary bladder, reproductive organs) include the inferior mesenteric plexus (associated with the inferior mesenteric artery), and the left colic plexus, sigmoid plexus, and superior hemorrhoidal plexus (associated with branches of the inferior mesenteric artery). Percutaneous intravascular access to these nerve structures can include passing a catheter through the left or right femoral artery (FIG. 14A), into the respective left or right common iliac artery 76 (FIGS. 10 and 14A), into the abdominal aorta, and into the inferior mesenteric artery (not shown) and into the branches thereof, if desired.

In one embodiment, a breast cancer patient may be treated with neuromodulation of the internal mammary plexus, which is intimately associated with the left and right internal thoracic arteries 33 (FIG. 5), and which may be achieved through intravascular access. In a particular example, and referring to FIGS. 5, 14A and 14B together, a catheter (not shown) may be inserted into the radial, brachial, or axillary artery 38 and passed to the subclavian artery 33 and into the internal thoracic artery 33 (FIG. 5). Alternatively, a catheter (not shown) may be inserted into the left or right femoral artery, passed through the left or right iliac artery to the abdominal aorta. From the abdominal aorta, the catheter can ascend the aorta to the aortic arch where it can pass through the left or right subclavian arteries and into the left or right internal thoracic arteries, respectively.

In other embodiments, neuromodulation of the pulmonary plexus, which is intimately associated with left and right pulmonary arteries 20, 21 (FIG. 4) may be achieved through intravascular access. Referring to FIG. 4 and back to FIGS. 14A and 14B, a treatment device (not shown), such as a catheter, may be inserted using standard angiographic technique into either the internal jugular, subclavian or femoral veins, and following venous inflow through the right atrium, tricuspid valve, right ventricle, pulmonic valve, and into the main pulmonary artery and right and left pulmonary arteries thereafter to access a target treatment site in the pulmonary vasculature that is in close proximity to the sympathetic chain.

B. Properties and Characteristics of the Vasculature

Properties and characteristics of the thoracic, abdominal and pelvic cavity vasculature impose challenges to both access and treatment methods, and to system/device designs. Since neuromodulation of the various sympathetic nerve structures innervating the targeted thoracic organs (e.g., pulmonary plexus, internal mammary plexus), the abdominal viscera (e.g., celiac plexus, superior mesenteric plexus, renal plexus, hepatic plexus, splenic plexus, gastric plexus, pancreatic plexus, etc.) or the pelvic/reproductive viscera (e.g., ovarian plexus, prostatic plexus, spermatic plexus, vaginal plexus, uterine plexus, sacral plexus, genitofemoral nerve, ilioinguinal nerve, pudendal nerve, perineal nerve, vesical plexus, hypogastric plexus, left colic plexus, sigmoid plexus, superior hemorrhoidal plexus, etc.) may be achieved in accordance with embodiments of the present technology through intravascular access, various aspects of the design of apparatus, systems, and methods for achieving such neuromodulation are disclosed herein. Aspects of the technology disclosed herein address additional challenges associated with variation of physiological conditions and architecture across the patient population and/or within a specific patient across time, as well as in response to cancer types and stage at diagnosis and/or treatment. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the desired vasculature targets via a minimally invasive intravascular path. However, minimally invasive arterial or venous access may be challenging for some targeted treatment sites, for example, because as compared to some other larger arteries that are routinely accessed using catheters, some of the target arteries (e.g., internal thoracic arteries, testicular arteries, ovarian arteries, prostatic arteries, internal iliac artery, etc.) can be tortuous, may be of relatively small diameter, and/or may require adjustments to the length and flexibility of the catheters. Arterial anatomy also may vary significantly from patient to patient, which further complicates minimally invasive access. Significant inter-patient variation may be seen, for example, in relative tortuosity, diameter, and/or length. Apparatus, systems and methods for achieving neuromodulation via intravascular access can account for these and other aspects of arterial or venous anatomy and its variation across the patient population when minimally invasively accessing an artery or vein. For example, spiral or helical computed tomography (CT) technology can be used to produce 3D images of the vascular features for individual patients, and intravascular path choice as well as device size/diameter, length, flexibility, etc. can be selected based upon the patient's specific vascular features.

In addition to complicating arterial access, specifics of the thoracic, abdominal or pelvic anatomy also complicate establishment of stable contact between neuromodulatory apparatus and a luminal surface or wall of an artery or vein. When the neuromodulatory apparatus includes an energy delivery element, such as an electrode, transducer or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within an artery, as well as tortuosity of the artery. Furthermore, establishing consistent contact can be complicated by patient movement, respiration, and/or the cardiac cycle because these factors may cause significant movement of the artery relative to the aorta, for example, and the cardiac cycle may transiently distend the target artery (i.e., cause the wall of the artery to pulse). To address these challenges, the treatment device or applicator may be designed with relative sizing and flexibility considerations. For example, the artery may have an internal diameter less than approximately 1.7 mm and the treatment device can be delivered using a 3 French, or in some cases, a 4 French sized catheter. In a further example, the renal artery may have an internal diameter in a range of about 2-10 mm and the treatment device can be delivered using a 3, 4, 5, 6, 7 French, or in some cases, a 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a desired target artery and facilitating stable contact between neuromodulatory apparatus and a luminal surface of the artery, nerves in and around the adventitia of the artery can be modulated via the neuromodulatory apparatus. Effectively applying thermal treatment from within an artery is non-trivial given the potential clinical complications associated with such treatment. For example, the intima and media of the artery are highly vulnerable to thermal injury. As discussed in greater detail below, the intima-media thickness separating the vessel lumen from its adventitia means that target nerves may be multiple millimeters distant (e.g., 2-3 mm) from the luminal surface of the artery. Sufficient energy can be delivered to or heat removed from the target sympathetic nerve fibers to modulate the target nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 2-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause irreversible damage to the thoracic, abdominal or pelvic organ, thermal treatment from within the artery can be applied carefully. Accordingly, the complex fluid mechanics and thermodynamic conditions present in the artery during treatment, particularly those that may impact heat transfer dynamics at the treatment site, may be important in applying energy (e.g., heating thermal energy) and/or removing heat from the tissue (e.g., cooling thermal conditions) from within the artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of a thermal energy delivery element (e.g., electrode, transducer, cryotherapeutic element or device, etc.) within the artery since location of treatment may also impact clinical efficacy. For example, full-circle lesion(s) likely resulting from a continuous circumferential treatment may be potentially related to artery stenosis. Therefore, the formation of more complex lesions along a longitudinal dimension of the artery via the cryotherapeutic devices or other energy delivery elements (e.g., electrodes, transducers, etc.) and/or repositioning of the neuromodulatory apparatus to multiple treatment locations may be desirable. Additionally, variable positioning and repositioning of the neuromodulatory apparatus may prove to be useful in circumstances where the artery is particularly tortuous or where there are proximal branch vessels off the artery main vessel, making treatment in certain locations challenging.

Blood flow through an artery may be temporarily occluded for a short time with minimal or no complications. However, occlusion for a significant amount of time can be avoided in some cases to prevent injury to the organ such as ischemia. It can be beneficial to avoid occlusion altogether or, if occlusion is beneficial, to limit the duration of occlusion (e.g., 2-5 minutes).

C. Neuromodulation of Target Sympathetic Nerve at Treatment Site

Referring back to FIGS. 4-12, in some embodiments the shaft(s) 47, 65, 66, 93 or 98, and the therapeutic element(s) 48, 68, 69, 94 or 99 can be portions of a treatment device at least partially corresponding to the treatment device 102 shown in FIG. 13. Referring to FIGS. 4-13 together, the therapeutic element(s) 48, 68, 69, 94 99 or 120 (collectively referred to as therapeutic element 120), for example, can be configured to radially expand into a deployed state at the treatment location and to contact an inner wall of a vessel of the target vasculature for, e.g., causing a suitable lesion or pattern of lesions. During treatment, the therapeutic element 120 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the therapeutic element 120 can be configured to cause therapeutically-effective neuromodulation (e.g., using ultrasound energy) without contacting a vessel wall.

A variety of other suitable treatment locations are also possible in and around the target artery, the target vein, and/or other suitable structures. In a specific example, since the testicular artery 91 (FIG. 11A) becomes narrower and more tortuous further from the aorta, it can be more convenient in some cases to treat the testicular artery 91 at its trunk. Furthermore, a treatment procedure can include treatment at any suitable number of treatment locations, e.g., a single treatment location, two treatment locations, or more than two treatment locations. In some embodiments, different treatment locations can correspond to different portions of the target artery, the target vein, and/or other suitable structures proximate tissue having relatively high concentrations of targeted sympathetic nerves (e.g., efferent sympathetic nerve fibers associated with organ comprising a malignant tumor, afferent nerve fibers associated with a diseased or damaged organ). The shaft(s) 47, 65, 66, 93, 98 or 112 (collectively referred to as shaft 112) can be steerable (e.g., via one or more pull wires) and can be configured to move the therapeutic element 120 between treatment locations. At each treatment location, the therapeutic element 120 can be activated to cause modulation of nerves proximate the treatment location. Activating the therapeutic element 120 can include, for example, heating, cooling, stimulating, or applying another suitable treatment modality at the treatment location. Activating the therapeutic element 120 can further include applying various energy modalities at varying power levels, intensities and for various durations for achieving modulation of nerves proximate the treatment location. In some embodiments, power levels, intensities and treatment duration can be determined and employed using various algorithms for ensuring modulation of nerves at select distances (e.g., depths) away from the treatment location. Furthermore, as noted previously, in some embodiments, the therapeutic element 120 can be configured to introduce (e.g., inject) a chemical (e.g., a drug or other agent) into target tissue at the treatment location. Such chemicals or agents can be applied at various concentrations depending on treatment location and the relative depth of the target nerves.

The therapeutic element 120 can be positioned at a treatment location within the target artery, for example, via a catheterization path including the femoral artery and the aorta (FIG. 14A), a catheterization path including the internal iliac artery, the external iliac artery or any vascular branches from these arteries, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The therapeutic element 120 can be configured to accommodate the anatomy of the target artery, the target vein, and/or another suitable structure. For example, the therapeutic element 120 can include a balloon (not shown) configured to inflate to a size generally corresponding to the internal size of the target artery, the target vein, and/or another suitable structure. Other treatment procedures for modulation of sympathetic nerves in accordance with embodiments of the present technology are also possible.

Figure 15:
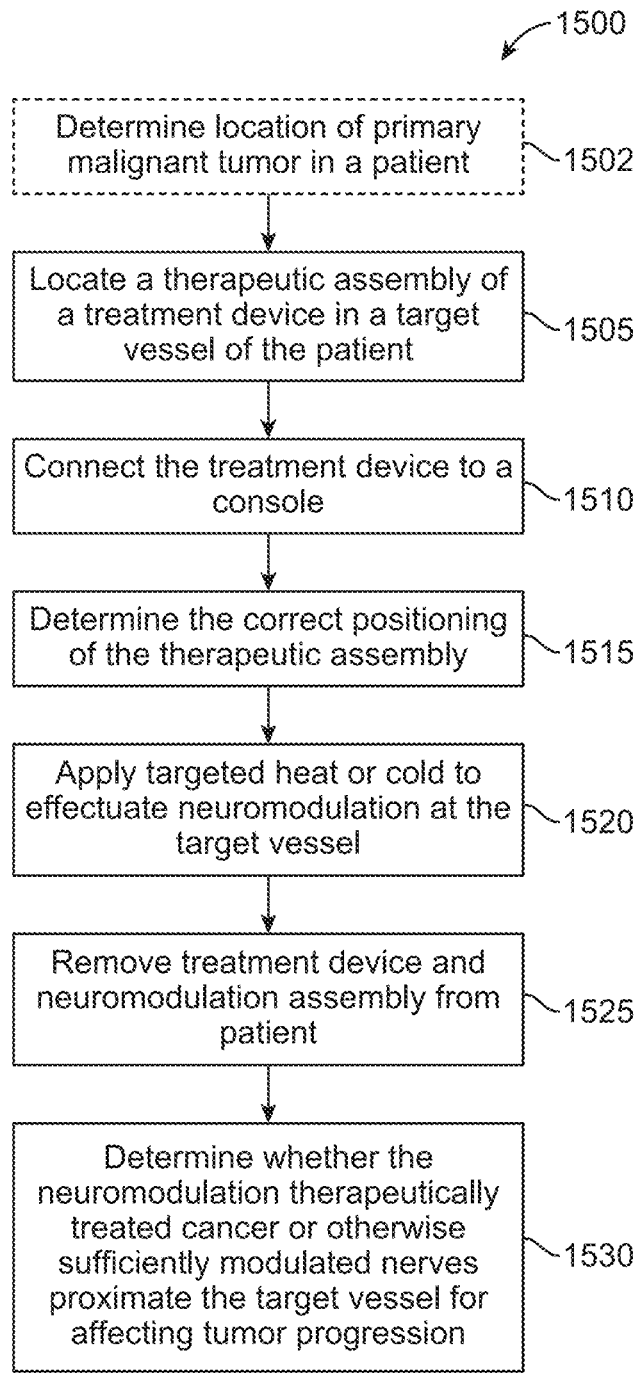
FIG. 15 is a block diagram illustrating a method of modulating target sympathetic nerves in accordance with an embodiment of the present technology.

FIG. 15 is a block diagram illustrating a method 1500 of modulating sympathetic nerves using the system 100 described above with reference to FIG. 13 or other suitable neuromodulation devices/systems. With reference to FIGS. 4-13, and 15 together, the method 1500 can optionally include determining the location of a primary malignant tumor in a patient (if not yet determined) and/or selecting a suitable patient for performing neuromodulation (block 1502). For example, a suitable patient can include a patient having cancer (e.g., a primary malignant tumor, a hematopoietic cancer), a patient at higher risk for developing cancer, a patient diagnosed with a pre-cancerous lesion and/or a patient previously treated for cancer. The method 1500 can include intravascularly locating the neuromodulation assembly 120 in a delivery state (e.g., low-profile configuration) at a first target site in or near a target blood vessel such as those listed in TABLES 1-3 and/or those having close proximity to a target SNS nerve fiber in the body (e.g., a pulmonary artery or vein, an internal thoracic artery, a celiac artery, superior mesenteric artery or vein, a renal artery or vein, a hepatic artery, a splenic artery or vein, a gastric artery, an inferior mesenteric artery or vein, a pancreatic artery, an ovarian artery or vein, a vaginal artery or vein, a uterine artery or vein, a testicular artery or vein, a prostatic artery, a common iliac artery or vein, an internal iliac artery or vein, an external iliac artery or vein, an internal pudendal artery or vein, a superior gluteal artery or vein, deep circumflex iliac artery or vein and/or another suitable structure) (block 1505).

In accordance with aspects of the present technology, a patient can be treated at one or more than one target sites. In certain embodiments, for example, a target site is adjacent to a target sympathetic nerve innervating tissue proximate the primary malignant tumor in the patient. Targeting SNS nerves innervating tissue or organs comprising cancer cells is expected to result in reduced or lower SNS nerve activity in such tissues, thereby inhibiting, preventing, slowing, disrupting or reversing tumor progression and/or metastasis of the primary cancer in the patient. In another embodiment, the target site is adjacent a renal nerve of the patient.

Targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing tumor progression and/or metastasis of the primary cancer in the patient. In a further embodiment, the target site is adjacent a target sympathetic nerve innervating a secondary tissue location, wherein the secondary tissue location has an increased likelihood of developing a metastatic tumor (e.g., based on the type/location of the primary malignant tumor). Without being bound by theory, targeting secondary tissue location(s) is anticipated to decrease a rate of colonization of circulating tumor cells at the secondary tissue site by, for example, altering a microenvironment at the secondary tissue location to be less habitable to colonization by the circulating tumor cells.

When intravascularly locating the neuromodulation assembly 120, the treatment device 102 and/or portions thereof (e.g., the neuromodulation assembly 120) can be inserted into a guide catheter or sheath to facilitate intravascular delivery of the neuromodulation assembly 120. In certain embodiments, for example, the treatment device 102 can be configured to fit within an 8 Fr guide catheter or smaller (e.g., 7 Fr, 6 Fr, 5 Fr, 4 Fr, 3 Fr, etc.) to access small peripheral vessels. A guide wire (not shown), if present, can be used to manipulate and enhance control of the shaft 112 and the neuromodulation assembly 120 (e.g., in an over-the-wire or a rapid-exchange configuration). In some embodiments, radiopaque markers and/or markings on the treatment device 102 and/or the guide wire can facilitate placement of the neuromodulation assembly 120 at the target site (e.g., a target vessel of a patient with cancer). In some embodiments, a contrast material can be delivered distally beyond the neuromodulation assembly 120, and fluoroscopy and/or other suitable imaging techniques can be used to aid in placement of the neuromodulation assembly 120 at the target site.

The method 1500 can further include connecting the treatment device 102 to the console 130 (block 1510), and determining whether the neuromodulation assembly 120 is in the correct position at the target site and/or whether the neuromodulation assembly (e.g., electrodes or cryotherapy balloon) is functioning properly (block 1515). After the neuromodulation assembly 120 is adequately positioned in the target vessel, it can be radially expanded or otherwise deployed using the handle 116 or other suitable control mechanism until the neuromodulation assembly 120 is positioned at its target site and in stable contact with the inner wall of the target vessel.

Once the neuromodulation assembly 120 is properly located at the target site and no malfunctions are detected, the console 130 can be manipulated to initiate application of an energy field provided by the energy source 104 to the target site to cause electrically-induced and/or thermally-induced modulation of target sympathetic nerves near the target vessel (e.g., using electrodes or cryotherapeutic devices) (block 1520). The purposeful application of energy from the neuromodulation assembly 120 is applied to tissue to induce one or more desired neuromodulating effects on localized regions of the target vessel and adjacent regions of the target sympathetic nerve fibers, which lay intimately within, adjacent to, or in close proximity to the adventitia of the target vessel. The neuromodulating effects may include denervation, thermal ablation, and non-ablative thermal alteration or damage (e.g., via sustained heating and/or resistive heating). The purposeful application of the energy may achieve neuromodulation along all or at least a portion of the target sympathetic nerve fibers.

In the deployed state, the neuromodulation assembly 120 can, in one embodiment, be configured to contact an inner wall of a target vessel to form a suitable lesion or pattern of lesions without the need for repositioning. For example, the neuromodulation assembly 120 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 120 can be configured to form a partially-circumferential lesion or a fully-circumferential lesion at a single longitudinal segment or zone of the vessel.

Accordingly, heating and/or cooling of the neuromodulation assembly 120 causes modulation of sympathetic nerves (e.g., efferent SNS fibers releasing catecholamines at innervated tissue sites, afferent nerve fibers transmitting sensory and pain signals that increase central sympathetic drive) at the target site to attenuate neural traffic along the target sympathetic nerves to provide a therapeutic beneficial reduction in one or more physiological parameters corresponding to the progression of the cancer in the patient.

In one example, the treatment device 102 can be an RF energy emitting device and RF energy can be delivered through energy delivery elements or electrodes to one or more locations along the inner wall of the target vessel for predetermined periods of time (e.g., 120 seconds). In some embodiments, multiple treatments (e.g., 4-6) may be administered in multiple target vessel locations as discussed above to achieve a desired coverage and/or desired inhibition of sympathetic neural activity in the body. For example, the target vessel can be a first target vessel (e.g., a first testicular artery) and the treatment procedure can include modulating nerves associated with a second target vessel (e.g., a second testicular artery) for the treatment of cancer associated with the testes. In another example, treatment for a patient diagnosed with pancreatic cancer can include modulating nerves (e.g., celiac plexus) associated with a first target vessel (e.g., a celiac artery) and can include modulating nerves (e.g., superior mesenteric plexus) associated with a second target vessel (e.g., a superior mesenteric artery). In yet another example, treatment for a patient diagnosed with a primary malignant tumor can include modulating nerves innervating tissue proximate the primary malignant tumor and associated with a first target vessel, and can include modulating nerves (e.g., renal plexus) associated a second target vessel (e.g., renal artery) for reducing, e.g., a level of whole body norepinephrine spillover. In a further embodiment, the treatment for a patient diagnosed with the primary malignant tumor can also include modulating nerves innervating a likely metastatic tissue location (e.g., liver, lung, etc.) and associated with a third target vessel for decreasing, e.g., a rate of colonization of circulating tumor cells at the likely metastatic tissue location.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would ablate nerve tissue (e.g., about 65° C.). A clinical objective of the procedure typically is to neuromodulate (e.g., lesion) a sufficient number of sympathetic nerves (either efferent or afferent nerves) to cause a reduction in sympathetic tone or drive to the organ(s). If the technical objective of a treatment is met (e.g., tissue is heated to about 65° C. to a depth of about 3 mm) the probability of forming a lesion in nerve tissue is high. The greater the number of technically successful treatments, the greater the probability of modulating a sufficient proportion of nerves, and thus the greater the probability of clinical success.

In a specific example of using RF energy for sympathetic nerve modulation, a clinician can commence treatment, which causes the control algorithm 134 (FIG. 13) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 102 can be a cryogenic device and cryogenic cooling can be applied for one or more cycles (e.g., for 30 second increments, 60 second increments, 90 second increments, etc.) in one or more locations along the circumference and/or length of the target vessel. The cooling cycles can be, for example, fixed periods or can be fully or partially dependent on detected temperatures (e.g., temperatures detected by a thermocouple (not shown) of the neuromodulation assembly 120). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

After providing the therapeutically-effective neuromodulation energy (e.g., cryogenic cooling, RF energy, ultrasound energy, etc.), the method 1500 may also include removing the treatment device 102 (e.g., catheter) and the neuromodulation assembly 120 from the patient (block 1525). In some embodiments, the neuromodulation assembly 120 can be an implantable device and a treatment procedure can include locating the neuromodulation assembly 120 at the treatment location using the shaft 112, fixing the neuromodulation assembly 120 at the treatment location, separating the neuromodulation assembly 120 from the shaft 112, and withdrawing the shaft 112. Other treatment procedures for modulation of target sympathetic nerves in accordance with embodiments of the present technology are also possible.

The method 1500 may further include determining whether the neuromodulation therapeutically treated the cancer patient or otherwise sufficiently modulated nerves or other neural structures proximate the target site(s) for inhibiting, preventing, slowing, disrupting or reversing tumor progression and/or metastasis of the primary cancer in the patient (block 1530). For example, the process of determining whether the neuromodulation therapeutically treated the nerves can include determining whether nerves were sufficiently modulated or otherwise disrupted to reduce, suppress, inhibit, block or otherwise affect the afferent and/or efferent signals, such as norepinephrine release by terminal nerve fibers (e.g., by evaluation of suitable biomarkers, stimulation and recording of nerve signals, etc.). In a further embodiment, patient assessment could be performed at time intervals (e.g., 1 month, 3 months, 6 months, 12 months, etc.) following neuromodulation treatment. For example, the patient can be assessed for measures of sympathetic activity (e.g., MSNA, and/or norepinephrine spillover to plasma, whole body norepinephrine spillover, and heart rate variability), measures of localized inflammation (e.g., IL-6, IL-8, etc.), and measures of cancer progression (e.g., tumor growth, cancer spread, etc.).

In other embodiments, various steps in the method 1500 can be modified, omitted, and/or additional steps may be added. In further embodiments, the method 1500 can have a delay between applying therapeutically-effective neuromodulation energy to a first target site at or near a first target vessel and applying therapeutically-effective neuromodulation energy to a second target site at or near a second target vessel. For example, neuromodulation treatment of nerves innervating tissue proximate the primary malignant tumor and associated with a first target vessel can take place at a first treatment session, and neuromodulation at the renal artery can take place a second treatment session at a later time.

As discussed previously, treatment procedures for modulation of sympathetic nerves in accordance with embodiments of the present technology are expected to improve one or more parameters associated with cancer progression (e.g., tumor growth, tumor vascularization, tumor metastasis, etc.). These and other clinical effects are expected to be detectable immediately after a treatment procedure or after a delay, e.g., of 1, 2, or 3 months. In some cases, sympathetic nerves can regenerate to a greater degree than other nerves. Accordingly, it may be useful to repeat neuromodulation at the same treatment location or a different treatment location after a suitable delay, e.g., 1, 2, or 3 years. In still other embodiments, however, other suitable treatment regimens or techniques may be used.

VII. Experimental Examples

Example 1

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter commercially available from Medtronic, Inc., of 710 Medtronic Parkway, Minneapolis, Minn. 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 2

Example 2 describes the outcome of catheter-based renal neuromodulation on animal subjects in an additional experiment. In this example (and referring to FIGS. 16A and 16B), studies using the pig model were performed using a multi-electrode Symplicity Spyral™ catheter or a single-electrode Symplicity Flex™ catheter along with a Symplicity G3™ generator. The catheters and generator are commercially available from Medtronic, Inc., of 710 Medtronic Parkway, Minneapolis, Minn. 55432-5604. The catheters were used in these cohorts of animals (n=66) to create multiple RF ablations in the renal vasculature. Cortical axon density in the renal cortex (FIG. 16A) and renal cortical norepinephrine (NE) concentration (FIG. 16B) were used as markers to measure procedural efficacy.

As shown in FIG. 16A, cortical axon area (per $mm^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

FIG. 16B includes (a) a graph of normalized cortical axon area vs. renal NE concentration, and (b) a graph of renal NE concentration vs. extent (%) of nerve ablation. Referring to the table of FIG. 16A and the two graphs of FIG. 16B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 16B, which demonstrates that a decrease in cortical axon area correlates with a decrease in NE levels. Referring to the second graph of FIG. 16B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 3

Example 3 describes a method for treating human patients with renal neuromodulation and anticipated outcomes of such treatment. In this example, human patients diagnosed with cancer will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming up to about six lesions at the distal segment of the renal artery and within a distance of approximately 6 mm proximal to the branch point within the renal artery using the Symplicity Flex™ catheter. The longitudinal spacing between the lesions may be approximately 2 mm, with a lesion footprint of approximately 2 mm each. For example, a first lesion can be formed about 5-6 mm from the bifurcation. The catheter can then be proximally retracted 1-2 mm and rotated 90 degrees followed by formation of a second lesion. Further lesions can be formed by sequential movement of the catheter proximally 1-2 mm, rotation of 90 degrees followed by lesion formation. As such, a longitudinal separation of lesions can occur approximately 1-2 mm apart along the longitudinal length of the distal segment of the main renal artery. For patients undergoing main artery treatment at a central segment of the main renal artery, a Symplicity Flex™ catheter can be used to form between 4 and 6 ablations in a spiral/helical pattern along the central segment of the main renal artery. For example, the first lesion can be placed approximately 5 mm proximal to the bifurcation, with each subsequent lesion placed 5 mm proximally with 90 degree rotation to form a spiral/helical pattern.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can be performed using a single-electrode Symplicity Flex™ catheter or a multi-electrode Symplicity Spyral™ catheter, both commercially available from Medtronic, Inc. Other multi-electrode, spiral/helical-shaped catheters having a tighter spiral/helix (e.g., smaller pitch) for forming multiple lesions close in proximity along the length of the vessel are contemplated for these methods. In a particular example, a method for efficaciously neuromodulating renal nerve tissue in a human patient can include advancing a single-electrode Symplicity Flex™ catheter to a first renal artery branch vessel approximately 6 mm distal to the bifurcation. A first lesion can be formed about 5-6 mm distal to the bifurcation. The catheter can then be proximally retracted 1-2 mm (e.g., maximum of 2 mm) and rotated 90 degrees followed by formation of a second lesion. Further lesions can be formed by sequential movement of the catheter proximally 1-2 mm, rotation of 90 degrees followed by lesion formation. As such, a longitudinal separation of lesions can occur approximately 1-2 mm apart along the longitudinal length of the first renal artery branch vessel (e.g., first branch trunk). In other examples, the catheter can be rotated (e.g., 90 degrees) following formation of the first lesion such that discrete lesions (e.g., non-continuous) are formed in the same longitudinal plane. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment location (e.g., locations along the main renal vessel, locations at or near the bifurcation, etc.). Other methods can include advancing a single-electrode Symplicity Flex™ catheter to a first renal artery branch vessel approximately 10 mm distal to the bifurcation. The first lesion can be formed about 9-10 mm distal to the bifurcation, and the catheter can then be proximally retracted and rotated for forming subsequent lesions as discussed above.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with cancer (e.g., primary malignant tumor at various locations in the body, hematopoietic cancer, etc.), pre-cancer, or a higher risk of cancer, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20%, about 30%, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial reduction in one or more measurable physiological parameters corresponding to the progression, initiation, and/or reoccurrence of cancer in the patient.

Example 4

Example 4 describes a method for treating human patients diagnosed with breast cancer with targeted sympathetic neuromodulation of SNS neural fibers innervating breast parenchyma and anticipated outcomes of such treatment. In this example, human patients diagnosed with a primary malignant tumor in the breast will be treated with neuromodulation of the internal mammary plexus which includes modulating SNS nerve tissue surrounding the internal thoracic artery.

For patients diagnosed with breast cancer, treatment can include targeting SNS neural fibers innervating the affected breast tissue (e.g., left or right breast), or in other embodiments, the method can include treating breast tissue associated with both breasts. Modulating nerve tissue can include forming up to about six lesions along a segment of the left and/or right internal thoracic arteries (e.g., after branching from the left and/or right subclavian arteries, respectively) using the single-electrode Symplicity Flex™ catheter or the multi-electrode Symplicity Spyral™ catheter, both commercially available from Medtronic, Inc. The longitudinal spacing between the lesions may be approximately 2 mm-5 mm, with a lesion footprint of approximately 2 mm each. When using the Symplicity Flex™ catheter, for example, following formation of a first lesion at a distalmost portion of the targeted internal thoracic artery, the catheter can then be proximally retracted 1-2 mm or 2-5 mm and rotated 90 degrees followed by formation of a second lesion. Further lesions can be formed by sequential movement of the catheter proximally 1-2 mm or 2-5 mm, rotation of 90 degrees followed by lesion formation. As such, a longitudinal separation of lesions can occur approximately 1-2 mm apart along the longitudinal length of the targeted segment of the internal thoracic artery. Following treatment at the first internal thoracic artery, the catheter can be withdrawn into the arch of the aorta and then advanced under fluoroscopy through the subclavian artery and into a second internal thoracic artery (e.g., on the contralateral side from the first selected treatment location) and the treatment procedure can be repeated.

Procedural efficacy may be measured using, for example, radiotracer dilution techniques that allow the estimation of regional sympathetic nervous activity from measurements of the organ-specific norepinephrine spillover rate. In an additional example, norepinephrine levels in breast tissue may be measured from biopsies taken at baseline (e.g., prior to breast SNS neuromodulation) and after treatment (e.g., about 1 month, 2 months, 3 months, 6 months, 12 months or more after treatment). Whole body physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with breast cancer (e.g., primary malignant tumor), a pre-cancer lesion or condition in the breast tissue, or a higher risk of developing breast cancer, with targeted neuromodulation of SNS nerve fibers associated with the internal thoracic artery will inhibit sympathetic neural activity in the internal mammary plexus in a manner that reduces a local sympathetic drive to the breast parenchyma by greater than about 10%, about 20%, about 30%, about 40%, about 50%, about 60%, about 70% or greater than about 80% in about 1 month, in about 3 months, in about 6 months or in about 12 months, or in another embodiment, in about 3 months to about 12 months, after neuromodulation treatment. Reduction in localized sympathetic drive to breast tissue in breast cancer patients is anticipated to result in a therapeutically beneficial reduction in one or more measurable physiological parameters corresponding to the progression, initiation, and/or reoccurrence of breast cancer in the patient.

It is further anticipated that neuromodulation treatments directed at target sympathetic nerves innervating organs and/or other tissues comprising or proximate to a primary source of cancer cells, including a primary malignant tumor, can be therapeutically beneficial for one or more of reducing a tumor growth rate and/or a rate of cancer cell division, decreasing a frequency of metastasis of the primary cancer, at least partially inhibiting vascularization of a primary malignant tumor at the targeted site, decreasing a number of metastatic tumors derived from the primary malignant tumor in the patient, and/or increasing effectiveness of chemotherapy drugs on the cancer cells within the primary malignant tumor. It is further anticipated that neuromodulation treatments directed at target sympathetic nerves innervating organs or tissue structures having a high likelihood of developing a metastatic tumor from circulating cancer cells can beneficially decrease a rate of colonization of circulating tumor cells at those targeted sites.

VIII. Further Examples

1. A method of treating a human patient diagnosed with a primary malignant tumor, the method comprising:
   intravascularly positioning a catheter carrying a neuromodulation assembly adjacent to a target sympathetic nerve innervating tissue proximate the primary malignant tumor in the patient;
   delivering energy to the target sympathetic nerve via the neuromodulation assembly to attenuate neural traffic along the target sympathetic nerve; and
   removing the catheter and neuromodulation assembly from the patient after treatment,
   wherein attenuating neural traffic along the target sympathetic nerve results in one or more of—
      a reduction in a tumor growth rate of the primary malignant tumor in the patient;
      a decrease in a frequency of metastasis of the primary malignant tumor;
      at least partial inhibition of vascularization of the primary malignant tumor;
      a decrease in a number of metastatic tumors derived from the primary malignant tumor in the patient; and
      increased effectiveness of a chemotherapy agent on cancer cells derived from the primary malignant tumor.

2. The method of example 1 wherein attenuating neural traffic along the target sympathetic nerve further decreases a number of circulating tumor cells in the patient.

3. The method of example 1 or example 2 wherein attenuating neural traffic along the target sympathetic nerve further inhibits at least one of lymphatic spread or hematogenous spread of tumor cells from the primary malignant tumor in the patient.

4. The method of any one of examples 1-3 wherein the primary malignant tumor is located in the breast, colon, kidney, pancreas, liver, prostate, cervix or ovary of the patient.

5. The method of example 1, further comprising:
   intravascularly positioning a second neuromodulation assembly adjacent to a renal nerve of the patient; and
   at least partially inhibiting sympathetic neural activity in the renal nerve of the patient via the second neuromodulation assembly,
   wherein inhibiting sympathetic neural activity in the renal nerve improves a measurable physiological parameter corresponding to the primary malignant tumor of the patient.

6. The method of example 5 wherein reducing sympathetic neural activity in the renal nerve in a manner that improves a measurable physiological parameter corresponding to the primary malignant tumor comprises reducing at least one of a primary malignant tumor growth rate, a primary malignant tumor size, a degree of vascularization of a primary malignant tumor and a number of circulating tumor cells.

7. The method of example 5 or example 6 wherein reducing sympathetic neural activity in the renal nerve in a manner that improves a measurable physiological parameter corresponding to the primary malignant tumor comprises improving an effectiveness of a chemotherapy agent on tumor cells in the patient.

8. The method of any one of examples 5-7 wherein reducing sympathetic neural activity in the renal nerve further reduces muscle sympathetic nerve activity (MSNA) in the patient.

9. The method of any one of examples 5-8 wherein reducing sympathetic neural activity in the renal nerve further reduces whole body norepinephrine spillover in the patient.

10. The method of example 9 wherein the whole body norepinephrine spillover is reduced by at least about 20% in about one month after reducing sympathetic neural activity in the renal nerve.

11. The method of example 9 or example 10 wherein the whole body norepinephrine spillover is reduced by greater than about 40% in about three months to about 12 months after reducing sympathetic neural activity in the renal nerve.

12. The method of any one of examples 9-11 wherein reducing whole body norepinephrine spillover in the patient decreases a level of vasoconstriction of vessels vascularizing tissue at or near the primary malignant tumor.

13. The method of any one of examples 9-12 wherein reducing whole body norepinephrine spillover in the patient decreases a number of colonies formed by circulating tumor cells at secondary tissue sites.

14. The method of any one of examples 9-13 wherein reducing whole body norepinephrine spillover in the patient decreases a rate of colonization of circulating tumor cells at secondary tissue sites.

15. The method of example 13 or example 14 wherein the secondary tissue sites are at least one of bone, lungs, liver and brain.

16. The method of example 1 or example 5, further comprising:
   intravascularly positioning a third neuromodulation assembly adjacent to a second target sympathetic nerve innervating a secondary tissue site; and
   delivering energy to the second target sympathetic nerve via the third neuromodulation assembly to attenuate neural traffic along the second target sympathetic nerve,
   wherein attenuating neural traffic along the second target sympathetic nerve decreases a rate of colonization of circulating tumor cells at the secondary tissue site.

17. The method of example 16 wherein the secondary tissue site is the liver, and wherein the third neuromodulation assembly is positioned within the celiac artery or the hepatic artery of the patient.

18. The method of example 16 wherein the secondary tissue site is the lung, and wherein the third neuromodulation assembly is positioned within a pulmonary artery of the patient.

19. The method of any one of examples 1-18 wherein attenuating neural traffic along the target sympathetic nerve comprises at least partially ablating the target sympathetic nerve.

20. The method of any one of examples 1-18 wherein attenuating neural traffic along the target sympathetic nerve comprises reducing sympathetic neural activity in the tissue proximate the primary malignant tumor in the patient.

21. The method of any one of examples 1-18 wherein attenuating neural traffic along the target sympathetic nerve comprises at least partially disrupting communication along sympathetic neural fibers.

22. The method of any one of examples 1-18 wherein attenuating neural traffic along the target sympathetic nerve comprises irreversibly disrupting communication along sympathetic neural fibers.

23. The method of any one of examples 1 and 19-22 wherein said attenuating neural traffic along the target sympathetic nerve is irreversible.

24. The method of any one of examples 1 and 19-22 wherein said attenuating neural traffic along the target sympathetic nerve is temporary.

25. The method of any one of examples 1-24 wherein attenuating neural traffic along the target sympathetic nerve comprises delivering an energy field to the target sympathetic nerve via the neuromodulation assembly.

26. The method of example 25 wherein delivering an energy field to the target sympathetic nerve comprises delivering at least one of radio frequency energy, ultrasound energy, high intensity ultrasound energy, laser energy, and microwave energy via the neuromodulation assembly.

27. A method of treating a human patient diagnosed with cancer, the method comprising:
    intravascularly positioning a neuromodulation assembly adjacent to a renal nerve of the patient; and
    at least partially inhibiting sympathetic neural activity in the renal nerve of the patient via the neuromodulation assembly,
    wherein at least partially inhibiting sympathetic neural activity results in a therapeutically beneficial reduction in one or more measurable physiological parameters corresponding to the progression of the cancer in the patient.

28. The method of example 27 wherein a measurable physiological parameter corresponding to the progression of the cancer is at least one of a primary malignant tumor growth rate, a primary malignant tumor size, a degree of vascularization of a primary malignant tumor and a number of circulating tumor cells.

29. The method of example 27 or example 28 wherein at least partially inhibiting sympathetic neural activity in the renal artery in a manner that results in a therapeutically beneficial reduction in one or more measurable physiological parameters comprises reducing at least one of an amount of lymphatic spread or hematogenous spread of tumor cells from a primary malignant tumor in the patient.

30. The method of any one of examples 27-29 wherein at least partially inhibiting sympathetic neural activity in the renal artery in a manner that results in a therapeutically beneficial reduction in one or more measurable physiological parameters comprises reducing a number of tumor-associated macrophages within or in proximity to a primary malignant tumor in the patient.

31. The method of any one of examples 27-30 wherein at least partially inhibiting sympathetic neural activity in the renal nerve further reduces whole body norepinephrine spillover in the patient.

32. The method of example 31 wherein the whole body norepinephrine spillover is reduced by at least about 20% in about one month after at least partially inhibiting sympathetic neural activity in the renal nerve.

33. The method of example 31 or example 32 wherein the whole body norepinephrine spillover is reduced by greater than about 40% in about three months to about 12 months after at least partially inhibiting sympathetic neural activity in the renal nerve.

34. The method of any one of examples 27-33 wherein the patient is diagnosed with a primary malignant tumor, and wherein at least partially inhibiting sympathetic neural activity further reduces whole body norepinephrine spillover in the patient in a manner that decreases a frequency of metastasis of the primary malignant tumor.

35. The method of example 34 wherein the primary malignant tumor is in one of the breast, pancreas, lung, prostate, ovary, colon, liver, kidney and skin.

36. The method of example 27 wherein the patient is diagnosed with lymphoma or leukemia.

37. The method of any one of examples 27-36 wherein the neuromodulation assembly is carried by a catheter, and wherein the method further comprises removing the catheter and the neuromodulation assembly from the patient after treatment.

38. The method of any one of examples 27-37 wherein at least partially inhibiting sympathetic neural activity in the renal nerve of the patient comprises at least partially ablating the renal nerve.

39. The method of any one of examples 27-38 wherein at least partially inhibiting sympathetic neural activity in the renal nerve of the patient comprises irreversibly disrupting communication along at least some sympathetic neural fibers.

40. The method of example 27, further comprising:
    percutaneously introducing an energy delivery element at a distal portion of a catheter proximate to neural fibers that control a function of an organ comprising a primary malignant tumor in the patient;
    at least partially disrupting communication along the neural fibers via the energy delivery element; and
    removing the energy delivery element and catheter from the patient after treatment,
    wherein at least partially disrupting communication along the neural fibers therapeutically reduces one or more of—
        a tumor growth rate of the primary malignant tumor in the patient;
        a frequency of metastasis of the primary malignant tumor;
        vascularization of the primary malignant tumor; and
        a number of metastatic tumors derived from the primary malignant tumor in the patient.

41. The method of example 40 wherein the organ comprising the primary malignant tumor is the breast, pancreas, liver, colon, prostate, ovary or kidney.

42. The method of example 1 or example 27, further comprising administering a β-blocker to the patient.

43. A method of treating a human patient having an increased risk of developing cancer, the method comprising:
    intravascularly positioning a neuromodulation assembly adjacent to a renal nerve of the patient; and at least partially inhibiting sympathetic neural activity in the renal nerve of the patient via the neuromodulation assembly, wherein at least partially inhibiting sympathetic neural activity results in a therapeutically beneficial reduction in one or more measurable physiological parameters corresponding to the initiation and/or promotion of cancer in the patient.

44. The method of example 43 wherein the human patient has a pre-cancerous lesion, has previously had a pre-cancerous lesion, has previously been diagnosed with cancer, is in remission from cancer, and/or has a genetic pre-disposition for developing cancer.

45. The method of example 43 or example 44 wherein at least partially inhibiting sympathetic neural activity in the renal nerve further reduces whole body norepinephrine spillover in the patient.

46. The method of any one of examples 43-45 wherein at least partially inhibiting sympathetic neural activity in a manner that results in a therapeutically beneficial reduction in one or more measurable physiological parameters corresponding to the initiation and/or promotion of cancer in the patient comprises at least one of reducing abnormal cell proliferation, reducing a level of inflammatory cytokines in the patient, and reducing a level of oncogene activation in cells in the patient.

IX. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of treating a human patient diagnosed with a primary malignant tumor, the method comprising:
   intravascularly positioning a catheter carrying a neuromodulation assembly adjacent to a target sympathetic nerve innervating a secondary tissue site that is different than a primary tissue site that includes the primary malignant tumor in the patient;
   delivering energy to the target sympathetic nerve via the neuromodulation assembly to attenuate neural traffic along the target sympathetic nerve;
   removing the catheter carrying the neuromodulation assembly from the patient after treatment;
   intravascularly positioning a second neuromodulation assembly adjacent to a second target sympathetic nerve innervating the primary tissue site; and
   delivering energy to the second target sympathetic nerve via the second neuromodulation assembly to attenuate neural traffic along the second traffic sympathetic nerve,
      wherein attenuating neural traffic along the target sympathetic nerve and the second target sympathetic nerve results in one or more of:
         a reduction in a tumor growth rate of the primary malignant tumor in the patient,
         a decrease in a frequency of metastasis of the primary malignant tumor,
         at least partial inhibition of vascularization of the primary malignant tumor,
         a decrease in a number of metastatic tumors derived from the primary malignant tumor in the patient,
         a decrease in a rate of colonization of circulating tumor cells at the secondary tissue site, or
         increased effectiveness of a chemotherapy agent on cancer cells derived from the primary malignant tumor.

2. The method of claim 1 wherein attenuating neural traffic along the target sympathetic nerve further decreases a number of circulating tumor cells in the patient.

3. The method of claim 1 wherein attenuating neural traffic along the target sympathetic nerve further inhibits at least one of lymphatic spread or hematogenous spread of tumor cells from the primary malignant tumor in the patient.

4. The method of claim 1 wherein the primary malignant tumor is located in the breast, colon, kidney, pancreas, liver, prostate, cervix or ovary of the patient.

5. The method of claim 1 wherein the secondary tissue site is the liver, and wherein the neuromodulation assembly is positioned within the celiac artery or the hepatic artery of the patient.

6. The method of claim 1 wherein the secondary tissue site is the lung, and wherein the neuromodulation assembly is positioned within a pulmonary artery of the patient.

7. The method of claim 1 wherein attenuating neural traffic along the target sympathetic nerve comprises at least partially ablating the target sympathetic nerve.

8. The method of claim 1 wherein attenuating neural traffic along the target sympathetic nerve comprises reducing sympathetic neural activity at or near the secondary tissue site in the patient.

9. The method of claim 1 wherein attenuating neural traffic along the target sympathetic nerve comprises at least partially disrupting communication along sympathetic neural fibers.

10. The method of claim 1 wherein attenuating neural traffic along the target sympathetic nerve comprises irreversibly disrupting communication along sympathetic neural fibers.

11. The method of claim 1 wherein attenuating neural traffic along the target sympathetic nerve is irreversible.

12. The method of claim 1 wherein attenuating neural traffic along the target sympathetic nerve is temporary.

13. The method of claim 1 wherein attenuating neural traffic along the target sympathetic nerve comprises delivering an energy field to the target sympathetic nerve via the neuromodulation assembly.

14. The method of claim 13 wherein delivering the energy field to the target sympathetic nerve comprises delivering at least one of radio frequency energy, ultrasound energy, high intensity ultrasound energy, laser energy, and microwave energy via the neuromodulation assembly.

15. The method of claim 1 wherein the secondary tissue site is a non-tumor site, and wherein attenuating neural traffic along the target sympathetic nerve decreases a rate of colonization of circulating tumor cells at the non-tumor site.

16. The method of claim 15, further comprising:
intravascularly positioning a third neuromodulation assembly adjacent to a renal nerve of the patient; and
at least partially inhibiting sympathetic neural activity in the renal nerve of the patient via the third neuromodulation assembly,
wherein inhibiting sympathetic neural activity in the renal nerve improves a measurable physiological parameter corresponding to the primary malignant tumor of the patient.

17. The method of claim 1 wherein the target sympathetic nerve is the renal nerve.

18. The method of claim 17 wherein attenuating neural traffic along the renal nerve results in reducing at least one of a primary malignant tumor growth rate, a primary malignant tumor size, a degree of vascularization of a primary malignant tumor and a number of circulating tumor cells.

19. The method of claim 7 wherein attenuating neural traffic along the renal nerve results in improving an effectiveness of a chemotherapy agent on tumor cells in the patient.

20. The method of claim 7 wherein attenuating neural traffic along the renal nerve further reduces muscle sympathetic nerve activity (MSNA) in the patient.

21. The method of claim 7 wherein attenuating neural traffic along the renal nerve further reduces whole body norepinephrine spillover in the patient.

22. The method of claim 21 wherein the whole body norepinephrine spillover is reduced by at least about 20% in about one month after attenuating neural traffic along the renal nerve.

23. The method of claim 21 wherein the whole body norepinephrine spillover is reduced by greater than about 40% in about three months to about 12 months after attenuating neural traffic along renal nerve.

24. The method of claim 21 wherein reducing whole body norepinephrine spillover in the patient decreases a level of vasoconstriction of vessels vascularizing tissue at or near the primary malignant tumor.

25. The method of claim 21 wherein reducing whole body norepinephrine spillover in the patient decreases a number of colonies formed by circulating tumor cells at one or more non-tumor sites.

26. The method of claim 21 wherein reducing whole body norepinephrine spillover in the patient decreases a rate of colonization of circulating tumor cells at one or more non-tumor sites.

27. The method of claim 25 wherein the one or more non-tumor sites are at least one of bone, lungs, liver and brain.

* * * * *